US012617749B2

(12) United States Patent
Abdur-Rashid et al.

(10) Patent No.: US 12,617,749 B2
(45) Date of Patent: May 5, 2026

(54) CANNABINOID DERIVATIVES AND PRECURSORS, AND ASYMMETRIC SYNTHESIS FOR SAME

(71) Applicant: KARE CHEMICAL TECHNOLOGIES INC., Mississauga (CA)

(72) Inventors: Kamaluddin Abdur-Rashid, Mississauga (CA); Wenli Jia, Toronto (CA); Kareem Abdur-Rashid, Mississauga (CA)

(73) Assignee: KARE CHEMICAL TECHNOLOGIES INC., Mississauga (CA)

( * ) Notice: Subject to any disclaimer, the term of this patent is extended or adjusted under 35 U.S.C. 154(b) by 1048 days.

(21) Appl. No.: 17/753,675

(22) PCT Filed: Sep. 9, 2020

(86) PCT No.: PCT/CA2020/051211
§ 371 (c)(1),
(2) Date: Mar. 10, 2022

(87) PCT Pub. No.: WO2021/046640
PCT Pub. Date: Mar. 18, 2021

(65) Prior Publication Data

US 2022/0340514 A1 Oct. 27, 2022

Related U.S. Application Data

(60) Provisional application No. 63/037,768, filed on Jun. 11, 2020, provisional application No. 62/898,221, filed on Sep. 10, 2019.

(51) Int. Cl.
*C07C 69/757* (2006.01)
*C07C 67/475* (2006.01)

(52) U.S. Cl.
CPC .......... *C07C 69/757* (2013.01); *C07C 67/475* (2013.01); *C07B 2200/05* (2013.01); *C07C 2601/16* (2017.05)

(58) Field of Classification Search
USPC .......................................................... 560/57
See application file for complete search history.

(56) References Cited

FOREIGN PATENT DOCUMENTS

| | | |
|---|---|---|
| WO | WO-2016138383 A1 | 9/2016 |
| WO | WO-2020117288 A1 | 6/2020 |
| WO | WO-2021046640 A1 | 3/2021 |

OTHER PUBLICATIONS

Trost et al. Organic Letters (2007), 9(5), 861-863.*
Haskins Biomedical Mass Spectrometry 1982, 9(7), 269-277.*
"International Application No. PCT/CA2020/051211, International Search Report and Written Opinion mailed Nov. 26, 2020", (Nov. 26, 2020), 18 pgs.
Driessen, Robert Andre, "Thesis: Deuterium Labeled Cannabinoids: Synthesis and Mass Spectrometry", Utrecht University, (May 12, 1951), 146 pgs.
Gong, Xudong, et al., "Synthesis of CBD and Its Derivatives Bearing Various C4'-Side Chains with a Late-Stage Diversification Method", J. Org. Chem. 2020, 85, (Dec. 30, 2019), 2704-2715.
Ohlsson, et al., "Single-Dose Kinetics of Deuterium-labelled Cannabidiol in Man After Smoking and Intravenous Administration", Biomedical and Environmental Mass Spectrometry, 13 (2), (Feb. 1986), 77-83.

* cited by examiner

*Primary Examiner* — Ana Z Muresan
(74) *Attorney, Agent, or Firm* — Schwegman Lundberg & Woessner, P.A.

(57) ABSTRACT

The present disclosure relates to new cannabinoid derivatives and precursors and catalytic asymmetric processes for their preparation. The disclosure also relates to pharmaceutical compositions and pharmaceutical and analytical uses of the new cannabinoid derivatives. The disclosure also relates to the deuterium, carbon-13 and carbon-14 containing derivatives of the compounds that can be prepared and purified prior to transformation to the desired individual deuterated cannabinoid products.

10 Claims, 2 Drawing Sheets

CANNABINOID DERIVATIVES AND PRECURSORS, AND ASYMMETRIC SYNTHESIS FOR SAME

CROSS-REFERENCE TO RELATED APPLICATIONS

This application is a U.S. national stage filing under 35 U.S.C. § 371 from International Application No. PCT/CA2020/051211, filed on Sep. 9, 2020, and published as WO2021/046640 on Mar. 18, 2021, which claims the benefit of priority to U.S. Provisional Application Nos. 62/898,221, filed Sep. 10, 2019, and 63/037,768, filed Jun. 11, 2020, the contents of which are incorporated herein by reference in their entirety.

FIELD OF THE DISCLOSURE

The present disclosure relates to new cannabinoid derivatives and precursors and catalytic asymmetric processes for their preparation. The disclosure also relates to pharmaceutical compositions and pharmaceutical and analytical uses of the new cannabinoid derivatives.

BACKGROUND OF THE DISCLOSURE

A cannabinoid is one of a class of diverse chemical compounds that acts on cannabinoid receptors that alter neurotransmitter release in the brain. Cannabinoids include the endocannabinoids produced naturally in the body by animals; phytocannabinoids found in cannabis and perrottetinenes found in liverworts. The most notable cannabinoids are tetrahydrocannabinol (THC), the primary psychoactive compound in cannabis, and Cannabidiol (CBD). There are more than 100 different cannabinoids isolated from cannabis, exhibiting varying effects.

Cannabidiol (CBD) is the non-psychoactive and primary medicinal component of the cannabis plant. As such, CBD has significant medicinal benefits. It has been shown to counteract the psychoactive effect of tetrahydrocannabinol (THC), the other main component of cannabis. Hence, over the years a variety of CBD-rich strains of cannabis has been developed and used medicinally for treating inflammation, AIDS, ALS, Alzheimer's disease, anorexia, anxiety, arthritis, asthma, cancer, depression, diabetes, epilepsy, glaucoma, migraine, nausea, neuropathic pain, Parkinson's disease, just to name a few. In addition, there are numerous clinical trials being conducted worldwide for pharmaceutical applications of CBD, THC, Cannabidivarin (CBDV), Tetrahydrocannabidivarin (THV) and other cannabinoids for these and numerous other illnesses.

Cannabinoids contain natural distribution of hydrogen isotopes. That is hydrogen accounts for 99.9844% and deuterium accounts for 0.0156%. Increased levels of deuterium incorporation may produce detectable deuterium kinetic isotope effects that could affect pharmacokinetic, pharmacological and therapeutic profiles in comparison with cannabinoids having naturally occurring levels of deuterium.

SUMMARY OF THE DISCLOSURE

The present disclosure, in some aspects, describes an approach to developing a method for the catalytic asymmetric synthesis of deuterated cannabinoids and their precursors. The processes focus on the use of commercially available chemicals and the use of these chemicals to prepare stable precursors that can be transformed into the desired deuterated cannabinoid products on demand. The approach can also be used to prepare cannabinoids containing other isotopes, such as carbon-13 and carbon-14.

In various aspects, the disclosure relates to the preparation of new precursors, and the use of such precursor compounds for the preparation of isotope labelled cannabinoid products using chiral and achiral catalysts and catalytic processes. The deuterium, carbon-13 and carbon-14 containing compounds can be prepared and purified prior to transformation to the desired individual deuterated cannabinoid products. The precursors are air-stable and shelf-stable compounds that can be stored, transported and converted into the desired isotope labelled cannabinoid products on demand.

In some embodiments, the deuterated cannabinoid compounds of the disclosure may expose a user to a maximum of about 0.000005% $D_2O$ or about 0.00001% DHO. These levels of deuterium are much lower than the minimum levels known to cause toxicity. Hence, the deuterium enriched compounds disclosed in the present disclosure should not cause any additional toxicity due to the formation of $D_2O$ and DHO upon drug metabolism.

In the embodiments of the disclosure, the deuterated cannabinoid compounds of the present disclosure maintain the beneficial aspects of the corresponding non-deuterated compounds while substantially increasing the maximum dose, decreasing toxicity, increasing the half-life, lowering the plasma concentration of the minimum efficacious dose, lowering the dose, and lowering the probability of drug-drug interactions.

In an embodiment of the disclosure, the deuterium, carbon-13 and carbon-14 enrichment is no less than about 1% at the specified position. In another embodiment, the deuterium, carbon-13 and carbon-14 enrichment is no less than about 5% at the specified position. In another embodiment, the deuterium, carbon-13 and carbon-14 enrichment is no less than about 10% at the specified position. In another embodiment, the deuterium, carbon-13 and carbon-14 enrichment is no less than about 20% at the specified position. In another embodiment, the deuterium, carbon-13 and carbon-14 enrichment is no less than about 50% at the specified position. In another embodiment, the deuterium, carbon-13 and carbon-14 enrichment is no less than about 70% at the specified position. In another embodiment, the deuterium, carbon-13 and carbon-14 enrichment is no less than about 80% at the specified position. In another embodiment, the deuterium, carbon-13 and carbon-14 enrichment is no less than about 90% at the specified position. In another embodiment, the deuterium, carbon-13 and carbon-14 enrichment is no less than about 98% at the specified position.

Other features and advantages of the present application will become apparent from the following detailed description. However, it should be understood that the detailed description and the specific examples, while indicating embodiments of the application, are given by way of illustration only and the scope of the claims should not be limited by these embodiments, but should be given the broadest interpretation consistent with the description as a whole.

BRIEF DESCRIPTION OF THE DRAWINGS

The disclosure will be described in greater detail with reference to the following drawings in which, which are meant to be illustrative by certain embodiments of the disclosure and are not meant to limit the scope of the disclosure.

DETAILED DESCRIPTION OF THE DISCLOSURE

(I) Definitions

Figure 1:
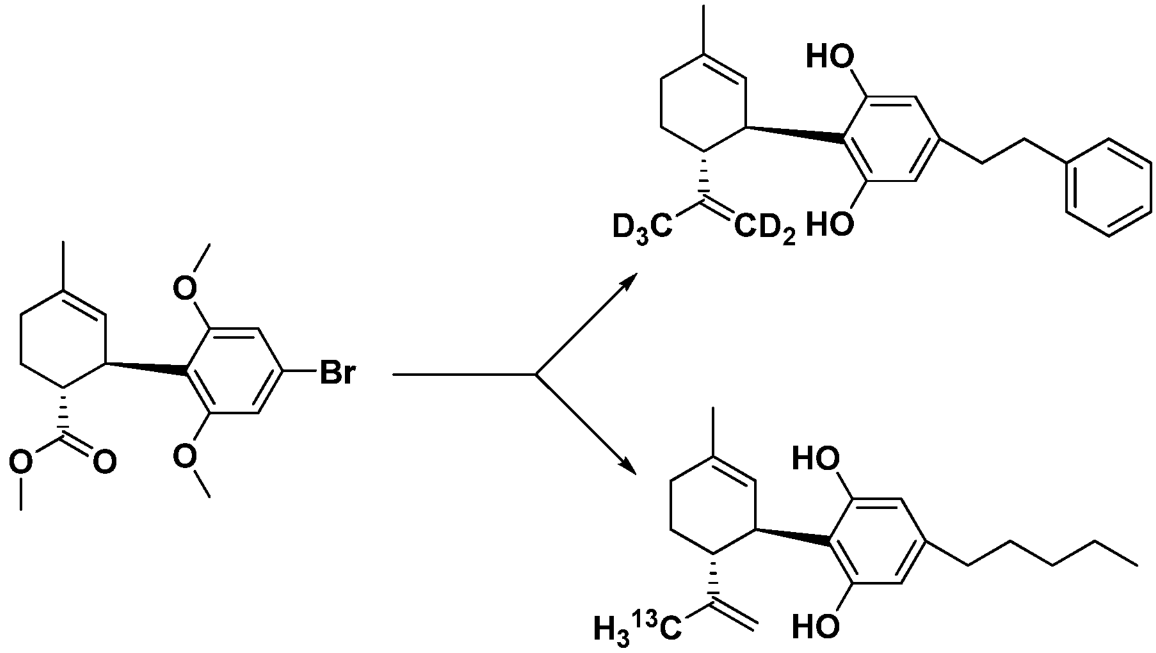
FIG. 1 shows the synthesis of compounds of the disclosure.

The term "alkyl" as used herein means straight and/or branched chain, saturated alkyl radicals containing one or more carbon atoms and includes (depending on the identity) methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like.

The term "alkenyl" as used herein means straight and/or branched chain, unsaturated alkyl radicals containing two or more carbon atoms and one to three double bonds, and includes (depending on the identity) vinyl, allyl, 2-methylprop-1-enyl, but-1-enyl, but-2-enyl, but-3-enyl, 2-methylbut-1-enyl, 2-methylpent-1-enyl, 4-methylpent-1-enyl, 4-methylpent-2-enyl, 2-methylpent-2-enyl, 4-methylpenta-1,3-dienyl, hexen-1-yl and the like.

The term "alkynyl" as used herein means straight and/or branched chain, unsaturated alkyl radicals containing two or more carbon atoms and one to three triple bonds, and includes (depending on the identity) acetylynyl, propynyl, but-1-ynyl, but-2-ynyl, but-3-ynyl, 3-methylbut-1-enyl, 3-methylpent-1-ynyl, 4-methylpent-1-ynyl, 4-methylpent-2-ynyl, penta-1,3-di-ynyl, hexyn-1-yl and the like.

The term "alkoxy" as used herein means straight and/or branched chain alkoxy group containing one or more carbon atoms and includes (depending on the identity) methoxy, ethoxy, propyloxy, isopropyloxy, t-butoxy, heptoxy, and the like.

The term "cycloalkyl" as used herein means a monocyclic, bicyclic or tricyclic saturated carbocylic group containing three or more carbon atoms and includes (depending on the identity) cyclopropyl, cyclobutyl, cyclopentyl, cyclodecyl and the like.

The term "aryl" as used herein means a monocyclic, bicyclic or tricyclic aromatic ring system containing at least one aromatic ring and 6 or more carbon atoms and includes phenyl, naphthyl, anthracenyl, 1,2-dihydronaphthyl, 1,2,3,4-tetrahydronaphthyl, fluorenyl, indanyl, indenyl and the like.

The term "heteroaryl" as used herein means a monocyclic, bicyclic or tricyclic ring system containing one or two aromatic rings and 5 or more atoms of which, unless otherwise specified, one, two, three, four or five are heteromoieties independently selected from N, NH, N(alkyl), O and S and includes thienyl, furyl, pyrrolyl, pyrididyl, indolyl, quinolyl, isoquinolyl, tetrahydroquinolyl, benzofuryl, benzothienyl and the like.

The term "halo" as used herein means halogen and includes chloro, fluoro, bromo or iodo.

The term "fluoro-substituted" as used herein means that at least one, including all, of the hydrogens on the referenced group is replaced with fluorine.

The suffix "ene" added on to any of the above groups means that the group is divalent, i.e. inserted between two other groups.

The term "ring system" as used herein refers to a carbon-containing ring system, that includes monocycles, fused bicyclic and polycyclic rings, bridged rings and metallocenes. Where specified, the carbons in the rings may be substituted or replaced with heteroatoms.

The term "deuterium enrichment" refers to the percentage of incorporation of deuterium at a given position in a molecule in the place of hydrogen. For example, deuterium enrichment of 1% at a given position means that 1% of molecules, in a given sample, contain deuterium at the specified position. Since the naturally occurring distribution of deuterium is about 0.0156%, deuterium enrichment at any position using non-enriched precursors is about 0.0156%.

The term "carbon-13 enrichment" or "carbon-14 enrichment" refers to the percentage of the incorporation at a given position in a molecule in the place of carbon-12. For example, carbon-13 enrichment at a given position means that 1% to 100% of molecules in a given sample contain carbon-13 at the specified position. Carbon-14 enrichment at a given position means that 0.00001% to 100% of molecules in a given sample contain carbon-14 at the specified position. The carbon-13 or carbon-14 enrichment occurs at any of the carbon atoms in the terpene unit of the compounds of the disclosure, including the carbon atoms in the cyclohexene ring and substituents.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. For instance, "including" also encompasses "including but not limited to". Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

(II) Compounds of the Disclosure

Accordingly, in some embodiments, the present disclosure relates to compounds of Formula (I):

(I)

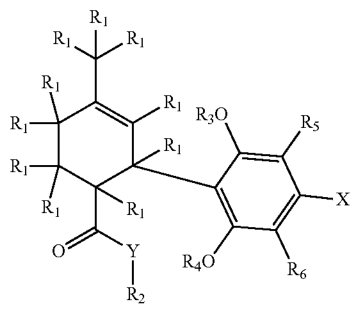

wherein, the $R_1$ groups are independently or simultaneously selected from the group consisting of hydrogen and deuterium;

$R_3$ to $R_4$ represents hydrogen, deuterium, a linear or branched alkyl group of any length, possibly substituted, an alkenyl group of any length, possibly substituted, an alkynyl group, possibly substituted, a cycloalkyl group, possibly substituted, an aryl group, possibly substituted, an heteroaryl group, possibly substituted, an acyl group, possibly substituted, and one or more of the carbon atoms in the alkyl, alkenyl, alkynyl, cycloalkyl, aryl, heteroaryl or acyl groups of $R_2$ to $R_4$ is optionally replaced with a heteroatom selected from the group consisting of O, S, N, P and Si, which, where possible, is optionally substituted with one or more groups;

Y represents O or $NR^c$, in which $R^c$ is a hydrogen atom or a cyclic, linear or branched alkyl, aryl or alkenyl group;

$R_2$ represents $OR^c$, a hydrogen atom or a cyclic, linear or branched alkyl, aryl or alkenyl group;

$R_5$ and $R_6$ represents hydrogen, deuterium, halide, a linear or branched alkyl group of any length, possibly substituted, an alkenyl group of any length, possibly substituted, an alkynyl group, possibly substituted, a cycloalkyl group, possibly substituted, an aryl group, possibly substituted, an heteroaryl group, possibly substituted, an acyl group, possibly substituted, a carboxylate group, possibly substituted, and one or more of the carbon atoms in the alkyl, alkenyl, alkynyl, cycloalkyl, aryl, heteroaryl, acyl or carboxylate groups of $R_5$ and/or $R_6$ is optionally replaced with a heteroatom selected from the group consisting of O, S, N, P and Si, which, where possible, is optionally substituted with one or more groups; and X represents a suitable leaving group, including but not limited to halide, sulfonate, carboxylate, carbonate or $MX_n$ groups (M=Li, Mg, Zn, Sn, B, Si; X is halide, OH, OR, $(C_1-C_{20})$-alkyl, $(C_1-C_{20})$-aryl, etc.; n=0 to 3).

In one embodiment, the $R_1$ groups are independently or simultaneously selected from the group consisting of hydrogen and deuterium;

$R_3$ to $R_4$ represents hydrogen, deuterium, an optionally substituted $C_1$-$C_{20}$-alkyl group, an optionally substituted $C_2$-$C_{20}$-alkenyl group, an optionally substituted $C_2$-$C_{20}$-alkynyl group, an optionally substituted $C_3$-$C_{20}$-cycloalkyl group, an optionally substituted $C_6$-$C_{14}$-aryl group, an optionally substituted $C_5$-$C_{14}$-heteroaryl, an optionally substituted acyl group, and one or more of the carbon atoms in the alkyl, alkenyl, alkynyl, cycloalkyl, aryl, heteroaryl or acyl groups of $R_3$ to $R_4$ is optionally replaced with a heteroatom selected from the group consisting of O, S, N, P and Si, which, where possible, is optionally substituted, wherein the optional substituents are one or more groups selected from OH, halo and $C_1$-$C_6$-alkyl;

Y represents O or $NR^c$, in which $R^c$ is a hydrogen atom, $C_1$-$C_6$-alkyl, $C_3$-$C_6$-cycloalkyl, $C_6$-$C_{10}$-aryl or $C_2$-$C_6$-alkenyl group;

$R_2$ represents a hydrogen atom, $C_1$-$C_6$-alkyl, $C_3$-$C_6$-cycloalkyl, $C_6$-$C_{10}$-aryl, $C_2$-$C_6$-alkenyl group or $OR^c$;

$R_5$ and $R_6$ represent hydrogen, deuterium, halide, an optionally substituted $C_1$-$C_{20}$-alkyl group, an optionally substituted $C_2$-$C_{20}$-alkenyl group, an optionally substituted $C_2$-$C_{20}$-alkynyl group, an optionally substituted $C_3$-$C_{20}$-cycloalkyl group, an optionally substituted $C_6$-$C_{14}$-aryl group, an optionally substituted $C_5$-$C_{14}$-heteroaryl, an optionally substituted acyl group, or an optionally substituted carboxylate group, and one or more of the carbon atoms in the alkyl, alkenyl, alkynyl, cycloalkyl, aryl, heteroaryl, acyl or carboxylate groups of $R_5$ and/or $R_6$ is optionally replaced with a heteroatom selected from the group consisting of O, S, N, P and Si, which, where possible, is optionally substituted, wherein the optional substituents are one or more groups selected from OH, halo and $C_1$-$C_6$-alkyl; and X represents a suitable leaving group.

In one embodiment, at least one of the $R_1$ groups is deuterium.

In one embodiment, at least one of the carbon-12 atoms in the following moiety from formula (I) is replaced with a carbon-13 or carbon-14 atom:

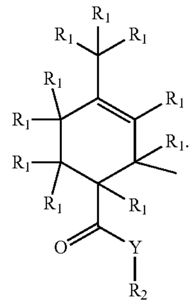

For example, at least one of the carbon-12 atoms in the cyclohexene ring and substituents, is replaced with a carbon-13 or carbon-14 atom.

In a general way, the compounds of Formula (I) can be prepared and isolated prior to use.

In some embodiments, the present disclosure relates to compounds of Formula (II):

(II)

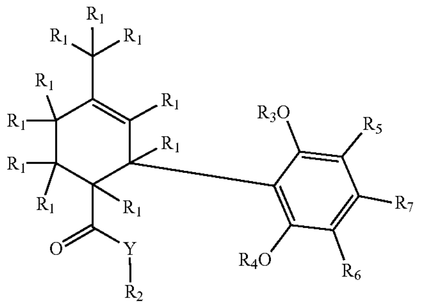

wherein, the $R_1$ groups are independently or simultaneously selected from the group consisting of hydrogen and deuterium; and at least one $R_1$ is deuterium;

$R_3$ to $R_4$ represents hydrogen, deuterium, a linear or branched alkyl group of any length, possibly substituted, an alkenyl group of any length, possibly substituted, an alkynyl group, possibly substituted, a cycloalkyl group, possibly substituted, an aryl group, possibly substituted, an heteroaryl group, possibly substituted, an acyl group, possibly substituted, and one or more of the carbon atoms in the alkyl, alkenyl, alkynyl, cycloalkyl, aryl, heteroaryl or acyl groups of $R_2$ to $R_4$ is optionally replaced with a heteroatom selected from the group consisting of O, S, N, P and Si, which, where possible, is optionally substituted with one or more groups;

Y represents O or $NR^c$, in which $R^c$ is a hydrogen atom or a cyclic, linear or branched alkyl, aryl or alkenyl group;

$R_2$ represents $OR^c$, a hydrogen atom or a cyclic, linear or branched alkyl, aryl or alkenyl group;

$R_5$ and $R_6$ represents hydrogen, deuterium, halide, a linear or branched alkyl group of any length, possibly substituted, an alkenyl group of any length, possibly substituted, an alkynyl group, possibly substituted, a cycloalkyl group, possibly substituted, an aryl group, possibly substituted, an heteroaryl group, possibly substituted, an acyl group, possibly substituted, a carboxylate group, possibly substituted, and one or more of the carbon atoms in the alkyl, alkenyl, alkynyl, cycloalkyl, aryl, heteroaryl, acyl or carboxylate groups of $R_5$ and/or $R_6$ is optionally replaced with a heteroatom selected from the group consisting of O, S, N, P and Si, which, where possible, is optionally substituted with one or more groups; and $R_7$ represents a hydrogen atom, a linear or branched alkyl group of any length, possibly substituted, or an alkenyl group of any length, possibly substituted, or an alkynyl group, possibly substituted, or a cycloalkyl group, possibly substituted, or an aryl group, possibly substituted.

In one embodiment, the $R_1$ groups are independently or simultaneously selected from the group consisting of hydrogen and deuterium; and at least one $R_1$ is deuterium;

$R_3$ to $R_4$ represents hydrogen, deuterium, an optionally substituted $C_1$-$C_{20}$-alkyl group, an optionally substituted $C_2$-$C_{20}$-alkenyl group, an optionally substituted $C_2$-$C_{20}$-alkynyl group, an optionally substituted $C_3$-$C_{20}$-cycloalkyl group, an optionally substituted $C_6$-$C_{14}$-aryl group, an optionally substituted $C_5$-$C_{14}$-heteroaryl, an optionally substituted acyl group, and one or more of the carbon atoms in the alkyl, alkenyl, alkynyl, cycloalkyl, aryl, heteroaryl or acyl groups of $R_3$ to $R_4$ is optionally replaced with a heteroatom selected from the group consisting of O, S, N, P and Si, which, where possible, is optionally substituted, wherein the optional substituents are one or more groups selected from OH, halo and $C_1$-$C_6$-alkyl;

Y represents O or $NR^c$, in which $R^c$ is a hydrogen atom, $C_1$-$C_6$-alkyl, $C_3$-$C_6$-cycloalkyl, $C_6$-$C_{10}$-aryl or $C_2$-$C_6$-alkenyl group;

$R_2$ represents a hydrogen atom, $C_1$-$C_6$-alkyl, $C_3$-$C_6$-cycloalkyl, $C_6$-$C_{10}$-aryl, $C_2$-$C_6$-alkenyl group or $OR^c$;

$R_5$ and $R_6$ represent hydrogen, deuterium, halide, an optionally substituted $C_1$-$C_{20}$-alkyl group, an optionally substituted $C_2$-$C_{20}$-alkenyl group, an optionally substituted $C_2$-$C_{20}$-alkynyl group, an optionally substituted $C_3$-$C_{20}$-cycloalkyl group, an optionally substituted $C_6$-$C_{14}$-aryl group, an optionally substituted $C_5$-$C_{14}$-heteroaryl, an optionally substituted acyl group, or an optionally substituted carboxylate group, and one or more of the carbon atoms in the alkyl, alkenyl, alkynyl, cycloalkyl, aryl, heteroaryl, acyl or carboxylate groups of $R_5$ and/or $R_6$ is optionally replaced with a heteroatom selected from the group consisting of O, S, N, P and Si, which, where possible, is optionally substituted, wherein the optional substituents are one or more groups selected from OH, halo and $C_1$-$C_6$-alkyl; and $R_7$ represents a hydrogen atom, an optionally substituted $C_1$-$C_{20}$-alkyl group, an optionally substituted $C_2$-$C_{20}$-alkenyl group, an optionally substituted $C_2$-$C_{20}$-alkynyl group, an optionally substituted $C_3$-$C_{20}$-cycloalkyl group, or an optionally substituted $C_6$-$C_{14}$-aryl group, wherein the optional substituents are one or more groups selected from OH, halo, $C_6$-aryl and $C_1$-$C_6$-alkyl.

In one embodiment, at least one of the carbon-12 atoms in the cyclohexene ring and its substituents, is replaced with a carbon-13 or carbon-14 atom.

In a general way, the compounds of Formula (II) can be prepared and isolated prior to use.

Accordingly, in some embodiments, the present disclosure relates to a compound of Formula (III):

(III)

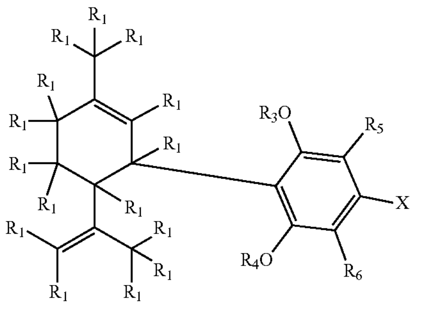

wherein, the $R_1$ groups are independently or simultaneously selected from the group consisting of hydrogen and deuterium;

$R_3$ to $R_4$ represents hydrogen, deuterium, a linear or branched alkyl group of any length, possibly substituted, or an alkenyl group of any length, possibly substituted, or an alkynyl group, possibly substituted, or a cycloalkyl group, possibly substituted, or an aryl group, possibly substituted, or an heteroaryl group, possibly substituted, or an acyl group, possibly substituted, and one or more of the carbon atoms in the alkyl, alkenyl, alkynyl, cycloalkyl, aryl, heteroaryl or acyl groups of $R_3$ to $R_4$ is optionally replaced with a heteroatom selected from the group consisting of O, S, N, P and Si, which, where possible, is optionally substituted with one or more groups;

$R_5$ and $R_6$ represents hydrogen, deuterium, halide, a linear or branched alkyl group of any length, possibly substituted, or an alkenyl group of any length, possibly substituted, or an alkynyl group, possibly substituted, or a cycloalkyl group, possibly substituted, or an aryl group, possibly substituted, or an heteroaryl group, possibly substituted, or an acyl group, possibly substituted, or a carboxylate group, possibly substituted, and one or more of the carbon atoms in the alkyl, alkenyl, alkynyl, cycloalkyl, aryl, heteroaryl, acyl or carboxylate groups of $R_5$ and/or $R_6$ is optionally replaced with a heteroatom selected from the group consisting of O, S, N, P and Si, which, where possible, is optionally substituted with one or more groups; and X represents a suitable leaving group, including but not limited to halide, sulfonate, carboxylate, carbonate or $MX_n$ groups (M=Li, Mg, Zn, Sn, B, Si; X is halide, OH, OR, ($C_1$-$C_{20}$)-alkyl, ($C_1$-$C_{20}$)-aryl, etc.; n=0 to 3).

In one embodiment, the $R_1$ groups are independently or simultaneously selected from the group consisting of hydrogen and deuterium;

$R_3$ to $R_4$ represents hydrogen, deuterium, an optionally substituted $C_1$-$C_{20}$-alkyl group, an optionally substituted $C_2$-$C_{20}$-alkenyl group, an optionally substituted $C_2$-$C_{20}$-alkynyl group, an optionally substituted $C_3$-$C_{20}$-cycloalkyl group, an optionally substituted $C_6$-$C_{14}$-aryl group, an optionally substituted $C_5$-$C_{14}$-heteroaryl, an optionally substituted acyl group, and one or more of the carbon atoms in the alkyl, alkenyl, alkynyl, cycloalkyl, aryl, heteroaryl or acyl groups of $R_3$ to $R_4$ is optionally replaced with a heteroatom selected from the group consisting of O, S, N, P and Si, which, where possible, is optionally substituted, wherein the optional substituents are one or more groups selected from OH, halo and $C_1$-$C_6$-alkyl;

$R_5$ and $R_6$ represent hydrogen, deuterium, halide, an optionally substituted $C_1$-$C_{20}$-alkyl group, an optionally substituted $C_2$-$C_{20}$-alkenyl group, an optionally substituted $C_2$-$C_{20}$-alkynyl group, an optionally substituted $C_3$-$C_{20}$-cycloalkyl group, an optionally substituted $C_6$-$C_{14}$-aryl group, an optionally substituted $C_5$-$C_{14}$-heteroaryl, an optionally substituted acyl group, or an optionally substituted carboxylate group, and one or more of the carbon atoms in the alkyl, alkenyl, alkynyl, cycloalkyl, aryl, heteroaryl, acyl or carboxylate groups of $R_5$ and/or $R_6$ is optionally replaced with a heteroatom selected from the group consisting of O, S, N, P and Si, which, where possible, is optionally substituted, wherein the optional substituents are one or more groups selected from OH, halo and $C_1$-$C_6$-alkyl; and X represents a suitable leaving group.

In one embodiment, at least one of the $R_1$ groups is deuterium.

In one embodiment, at least one of the carbon-12 atoms in the following moiety from formula (III) is replaced with a carbon-13 or carbon-14 atom:

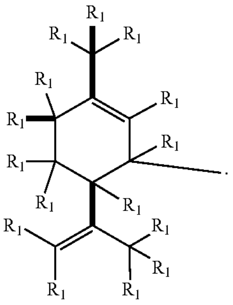

For example, at least one of the carbon-12 atoms in the cyclohexene ring and its substituents, is replaced with a carbon-13 or carbon-14 atom.

In one embodiment, the compound of Formula (III) is

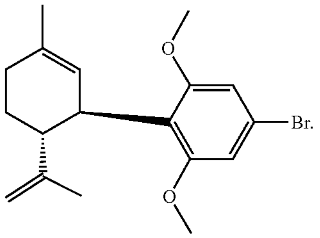 [SMILES: C=C(C)[C@@H]1CCC(C)=C[C@H]1c1c(OC)cc(Br)cc1OC]

In one embodiment, the alkyl groups of any length in any of the Formulas of the disclosure for the compounds and the processes is optionally substituted $C_1$-$C_{20}$-alkyl. In another embodiment, the alkyl group is optionally substituted $C_1$-$C_{10}$-alkyl. In another embodiment, the alkyl group is optionally substituted $C_1$-$C_6$-alkyl. In another embodiment, the alkyl group is methyl, ethyl, propyl, butyl or pentyl. In another embodiment, the optional substituents are hydroxyl, halo or $C_1$-$C_6$-alkyl.

In one embodiment, the alkenyl groups of any length in any of the Formulas of the disclosure for the compounds and the processes is optionally substituted $C_2$-$C_{20}$-alkenyl. In another embodiment, the alkenyl group is optionally substituted $C_2$-$C_{10}$-alkenyl. In another embodiment, the alkenyl group is optionally substituted $C_2$-$C_6$-alkenyl. In another embodiment, the alkenyl group is ethenyl, propenyl, butenyl or pentenyl. In another embodiment, the optional substituents are hydroxyl, halo or $C_1$-$C_6$-alkyl.

In one embodiment, the alkynyl groups of any length in any of the Formulas of the disclosure for the compounds and the processes is optionally substituted $C_2$-$C_{20}$-alkynyl. In another embodiment, the alkynyl group is optionally substituted $C_2$-$C_{10}$-alkynyl. In another embodiment, the alkynyl group is optionally substituted $C_2$-$C_6$-alkynyl. In another embodiment, the alkynyl group is ethynyl, propynyl, butynyl or pentynyl. In another embodiment, the optional substituents are hydroxyl, halo or $C_1$-$C_6$-alkyl.

In one embodiment, the cycloalkyl groups in any of the Formulas of the disclosure for the compounds and the processes is optionally substituted $C_3$-$C_{20}$-cycloalkyl. In another embodiment, the cycloalkyl group is optionally substituted $C_3$-$C_{10}$-cycloalkyl. In another embodiment, the cycloalkyl group is optionally substituted $C_3$-$C_6$-cycloalkyl. In another embodiment, the cycloalkyl group is cyclopropyl, cyclobutyl or cyclopentyl. In another embodiment, the optional substituents are hydroxyl, halo or $C_1$-$C_6$-alkyl.

In one embodiment, the aryl groups in any of the Formulas of the disclosure for the compounds and the processes is optionally substituted $C_6$-$C_{14}$-aryl. In another embodiment, the aryl group is optionally substituted $C_6$-$C_{10}$-aryl, or phenyl. In another embodiment, the aryl group is phenyl, naphthyl, tetrahydronaphthyl, phenanthrenyl, biphenylenyl, indanyl, or indenyl and the like. In another embodiment, the optional substituents are hydroxyl, halo or $C_1$-$C_6$-alkyl.

In one embodiment, the heteroaryl groups in any of the Formulas of the disclosure for the compounds and the processes is optionally substituted $C_6$-$C_{14}$-heteroaryl. In another embodiment, the heteroaryl group is optionally substituted $C_5$-$C_{10}$-heteroaryl, or $C_6$-$C_6$-heteroaryl. In another embodiment, the heteroaryl group is benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, quinolinyl, quinazolinyl, triazolyl, thiazolyl, thiophenyl, tetrahydroindolyl, tetrazolyl, thiadiazolyl, thienyl, triazolyl and the like. In another embodiment, the optional substituents are hydroxyl, halo or $C_1$-$C_6$-alkyl.

In another embodiment, the compounds of the disclosure include

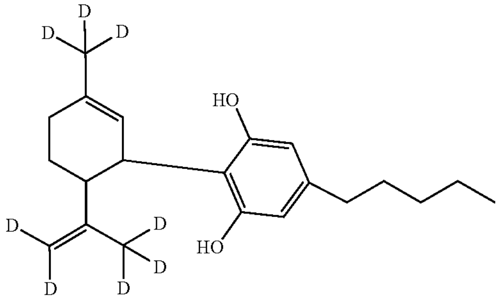

-continued
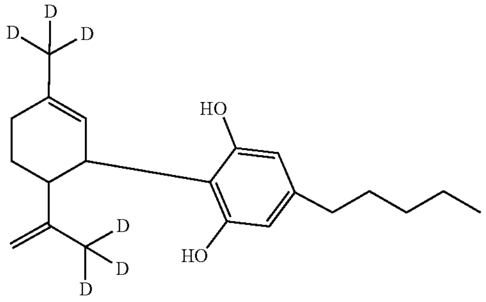
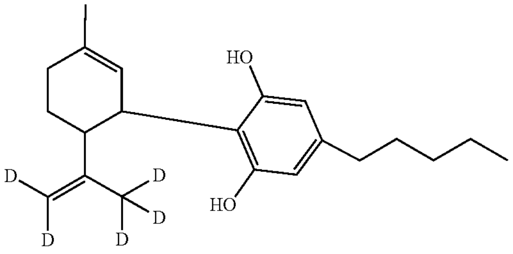
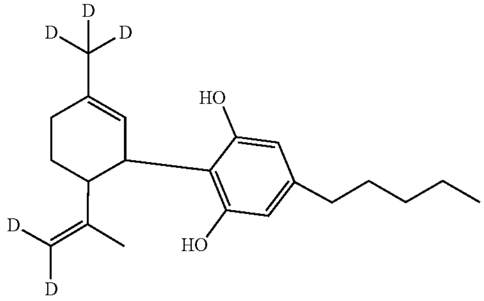
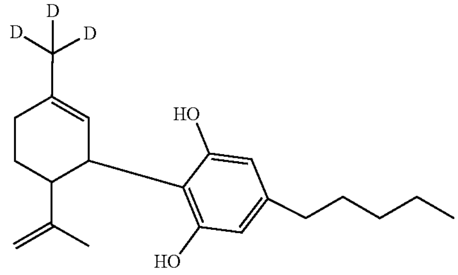
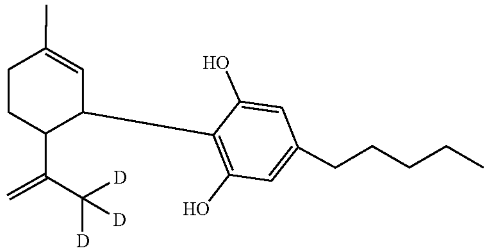
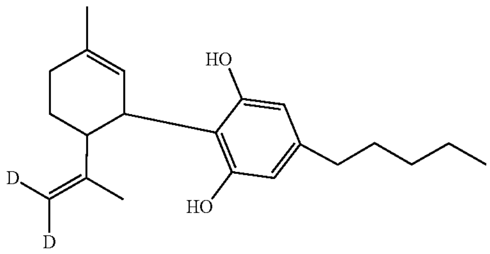
-continued
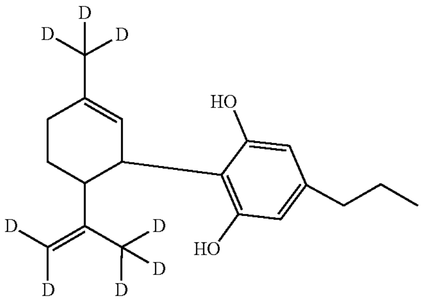
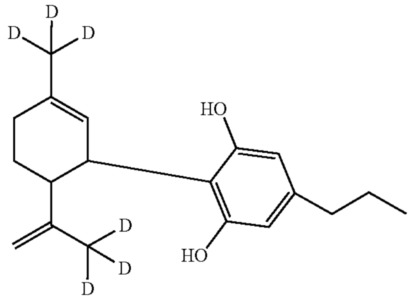
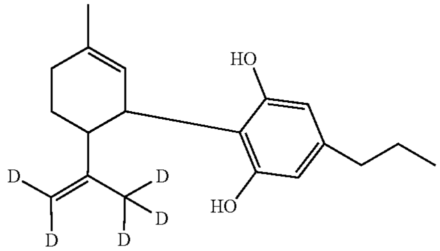
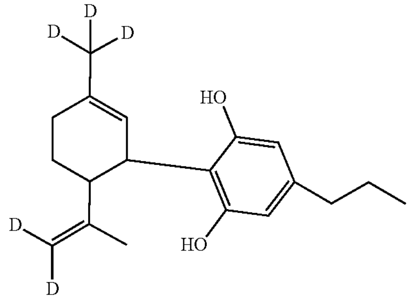
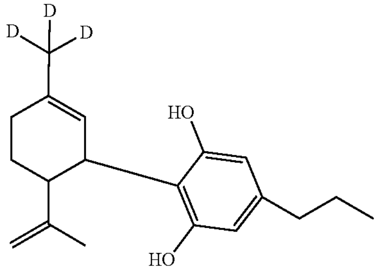
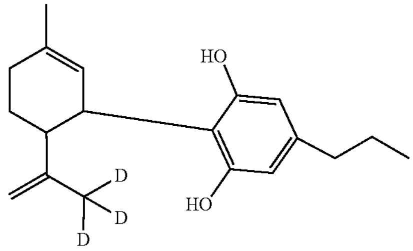

-continued
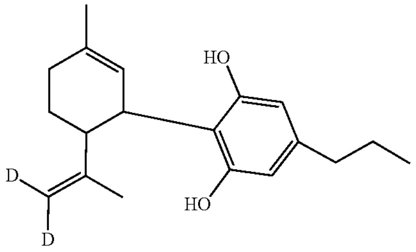
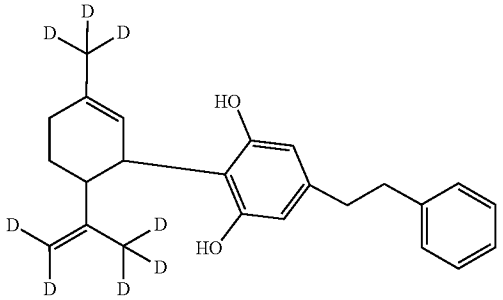
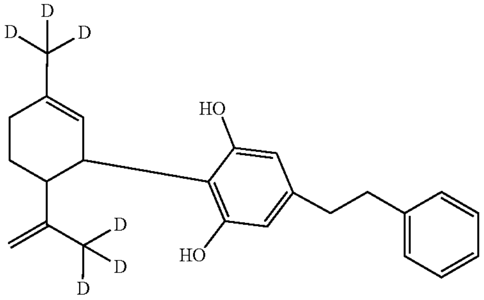
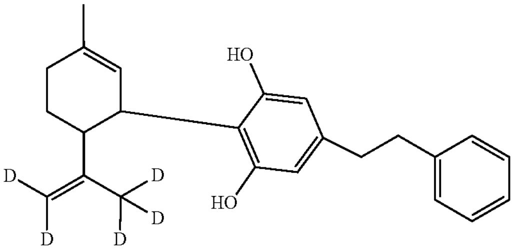
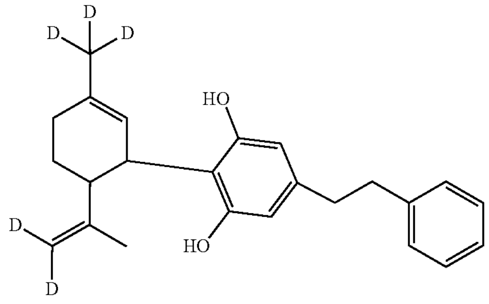
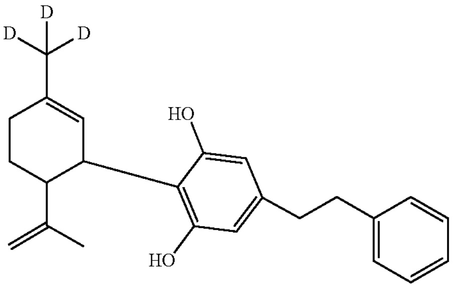
-continued
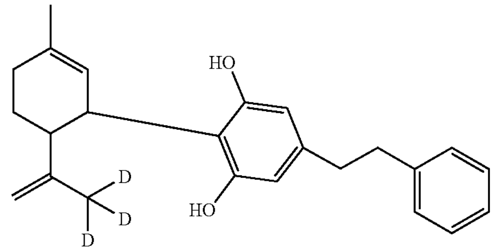
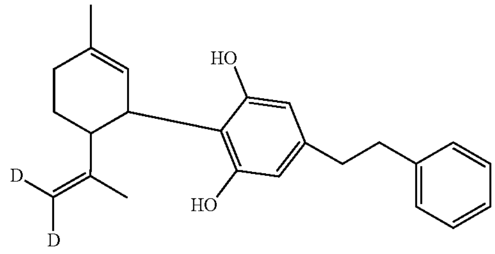
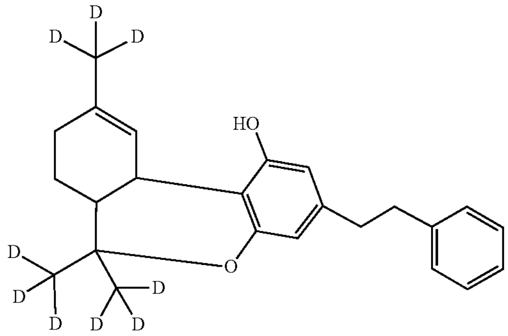
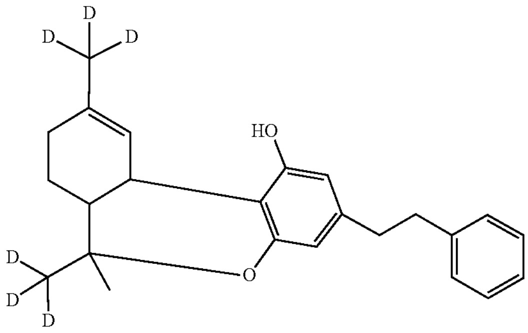
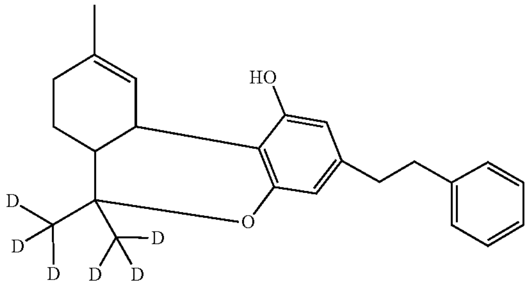

-continued
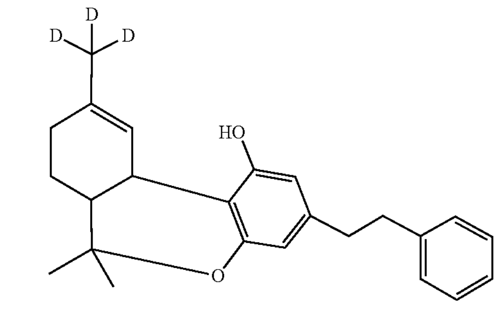
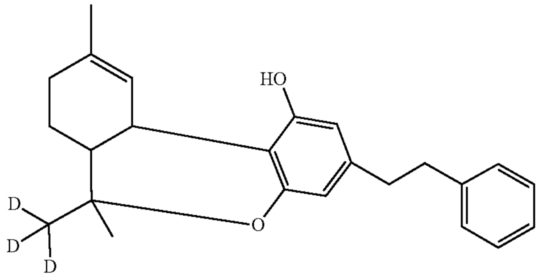
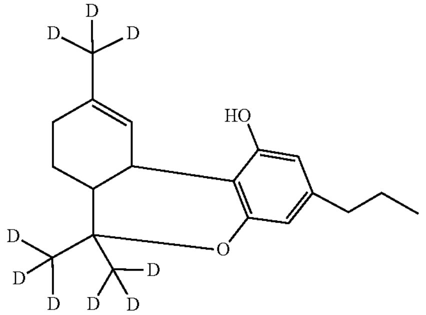
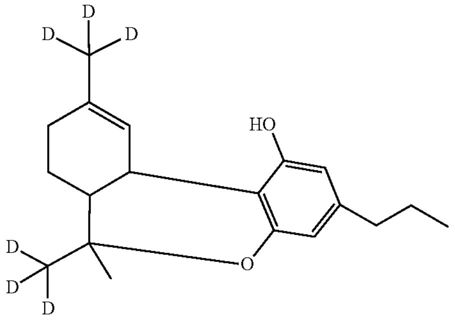
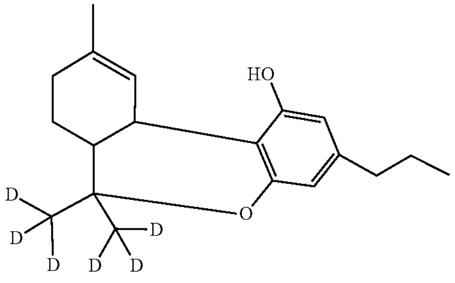
-continued
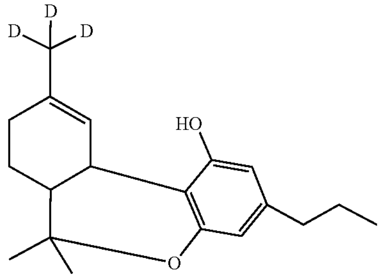
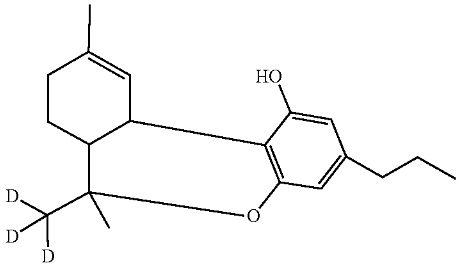
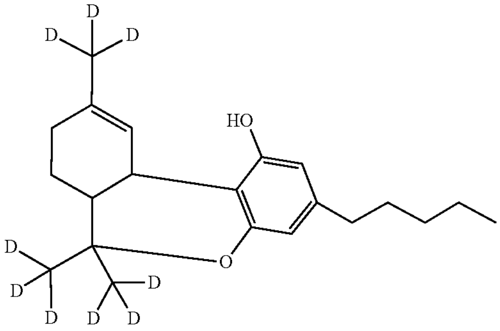
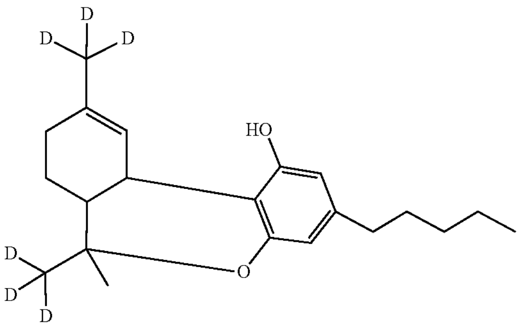
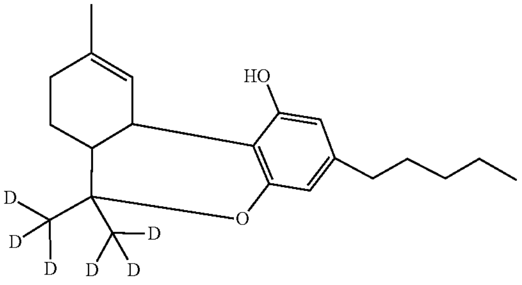

-continued

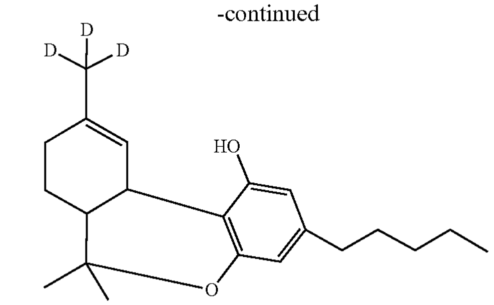

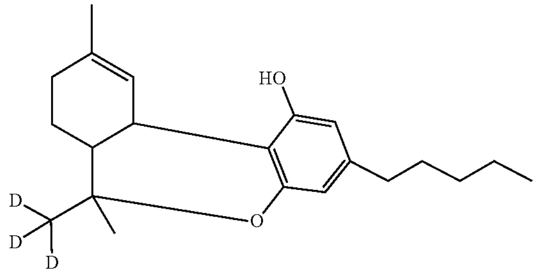

(III) Processes for Preparing Compounds

The present disclosure also relates to processes for the preparation of compounds of the disclosure.

The disclosure also relates to processes for the catalytic and non-catalytic production of the compounds of the disclosure. Such processes include catalytic hydrogenation, olefin metathesis and carbon-carbon bond forming reactions.

Catalytic hydrogenation reactions include asymmetric and non-asymmetric hydrogenation. Desirable catalysts include chiral and achiral transition metal catalysts, including but not limited to catalysts containing iron, ruthenium, osmium, cobalt, rhodium and iridium. Preferred catalysts include chiral and achiral ruthenium catalysts of the type $RuX_2$(diphosphine)(diamine), $RuX_2$(diphosphine)(aminophosphine), $RuX_2(aminophosphine)_2$ and RuX(arene)(tosyldiamine).

Bond forming reactions include, but are not limited to catalytic and non-catalytic Ullman, Suzuki-Miyaura, Negishi, Kumada, Sonogashira and Stille reactions.

In some embodiments of the disclosure, the coupling reactions require a boron containing compound such as $R_7$—$B(OH)_2$, $R_7$—$B(OR)_2$ or $R_7$—$BF_3K$; or a Grignard compound such as $R_7$—MgX; or an organozinc compound, such as $R_7$—ZnX, in the presence or absence of a catalyst, wherein $R_7$ is as defined above, and R is $C_1$-$C_{10}$-alkyl or $C_6$-$C_{10}$-aryl. In one embodiment, R is $C_1$-$C_6$-alkyl or $C_6$-aryl.

In some embodiments of the disclosure, the catalytic system characterizing the process of the instant disclosure may comprise a base. In some embodiments, said base can be any conventional base. In some embodiments, non-limiting examples include: organic non-coordinating bases such as DBU, an alkaline or alkaline-earth metal carbonate, a carboxylate salt such as sodium or potassium acetate, or an alcoholate or hydroxide salt. Preferred bases are the alcoholate or hydroxide salts selected from the group consisting of the compounds of formula $(RO)_2M'$ and ROM", wherein M' is an alkaline-earth metal, M" is an alkaline metal and R stands for hydrogen or a linear or branched alkyl group.

In some embodiments of the disclosure, the reactions require a suitable acid catalyst. Suitable acid catalysts include but are not limited to Lewis acids, organic acids and inorganic acids.

The catalyst can be added to the reaction medium in a large range of concentrations. As non-limiting examples, one can cite as catalyst concentration values ranging from 0.01% to 50%, relative to the amount of substrate, thus representing respectively a substrate/catalyst (S/cat) ratio of 10,000 to 2. Preferably, the complex concentration will be comprised between 0.1% and 10%, i.e. a S/cat ratio of 1,000 to 10 respectively. In some preferred embodiments, there will be used concentrations in the range of 1.0 to 5%, corresponding to a S/cat ratio of 100 to 20 respectively.

If required, useful quantities of base, added to the reaction mixture, may be comprised in a relatively large range. In some embodiments, non-limiting examples include: ranges between 1 to 100 molar equivalents relative to the substrate. However, it should be noted that it is also possible to add a small amount of base (e.g. base/substrate=1 to 3) to achieve high yields.

In the processes of this disclosure, the catalytic reaction can be carried out in the presence or absence of a solvent. When a solvent is required or used for practical reasons, then any solvent currently used in catalytic reactions can be used for the purposes of the disclosure. Non-limiting examples include aromatic solvents such as benzene, toluene or xylene, hydrocarbon solvents such as hexane or cyclohexane, ethers such as tetrahydrofuran, or yet primary or secondary alcohols, or water, or mixtures thereof. A person skilled in the art is well able to select the solvent most convenient in each case to optimize the catalytic reaction.

The temperature at which the catalytic reaction can be carried out is comprised between −30° C. and 200° C., more preferably in the range of between 0° C. and 100° C. Of course, a person skilled in the art is also able to select the preferred temperature.

Standard catalytic conditions, as used herein, typically implies the mixture of the substrate with the catalyst with or without a base, possibly in the presence of a solvent, and then treating such a mixture with the desired reactant at a chosen temperature in air or under an inert atmosphere of nitrogen or argon gas. Varying the reaction conditions, including for example, catalyst, temperature, solvent and reagent, to optimize the yield of the desired product would be well within the abilities of a person skilled in the art.

Accordingly, in some embodiments, the present disclosure relates to a process for preparing compounds of the Formula (I) comprising:

(a) contacting an α,β-unsaturated ketone of Formula (XXI) with hydrogen in the presence of a catalyst to form an allylic alcohol of Formula (XXII);

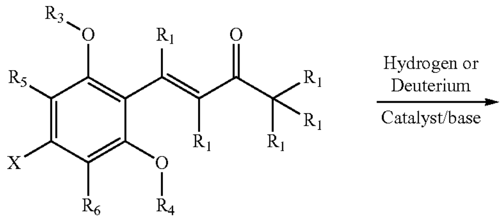

(XXI)

-continued

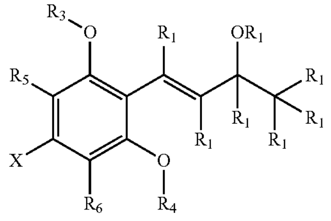

(XXII)

For example, the α,β-unsaturated ketone (E)-4-(4-bromo-2,6-dimethoxyphenyl)but-3-en-2-one was hydrogenated to the chiral allylic alcohol (S,E)-4-(4-bromo-2,6-dimethoxyphenyl)but-3-en-2-ol using the chiral ruthenium catalyst $RuCl_2$((R)-Xyl-Garphos)(R-Daipen) in the presence of hydrogen gas and a base:

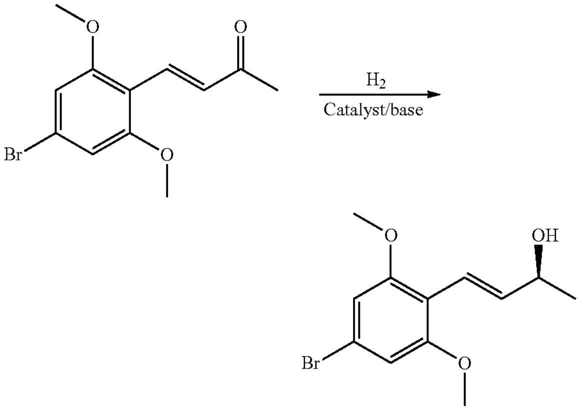

(b) contacting the allylic alcohol of Formula (XXII) with a 5-methylhex-5-enoic acid in the presence of a coupling agent to form an allylic ester of Formula (XXIV);

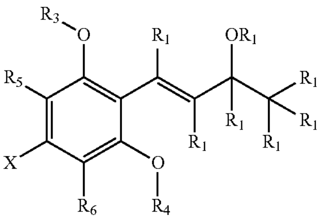

(XXII)

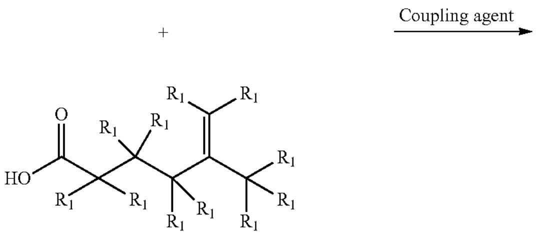

(XXIII)

-continued

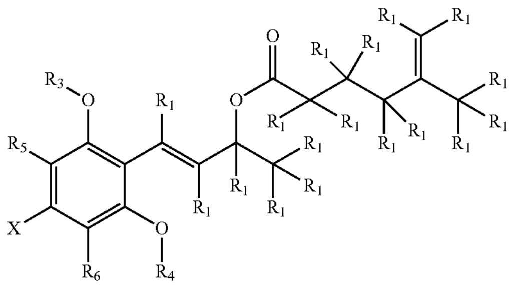

(XXIV)

For example, the chiral allylic alcohol (S,E)-4-(4-bromo-2,6-dimethoxyphenyl)but-3-en-2-ol was reacted with 5-methylhex-5-enoic acid in the presence of the coupling agent, for example, N,N'-Dicyclohexylcarbodiimide (DCC) to form the allylic ester (S,E)-4-(4-bromo-2,6-dimethoxyphenyl)but-3-en-2-yl 5-methylhex-5-enoate:

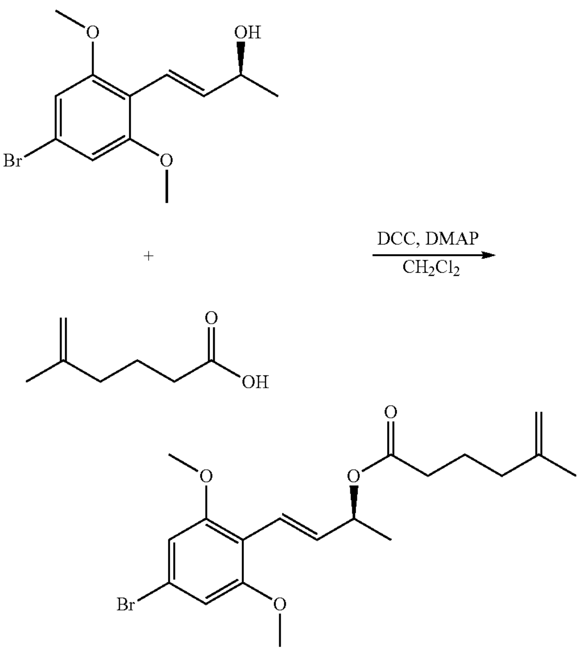

(c) rearranging and transforming the allylic ester of Formula (XXIV) to a γ,δ-unsaturated carboxylic acid ester of Formula (XXV);

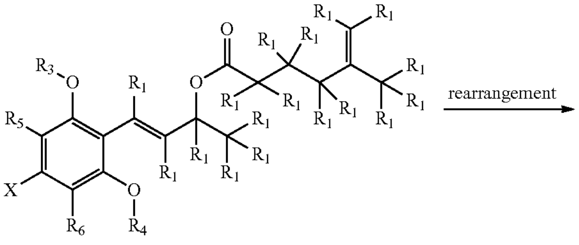

(XXIV)

-continued

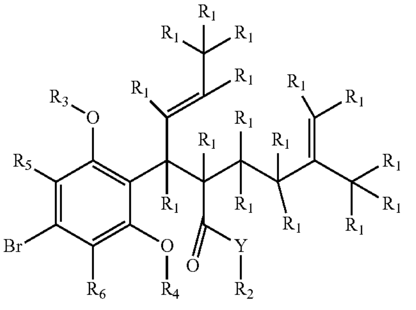

(XXV)

For example, the allylic ester (S,E)-4-(4-bromo-2,6-dimethoxyphenyl)but-3-en-2-yl 5-methylhex-5-enoate was rearranged to the γ,δ-unsaturated carboxylic acid (2R,3R,E)-3-(4-bromo-2,6-dimethoxyphenyl)-2-(3-methylbut-3-enyl) hex-4-enoic acid, which was reacted with methyl iodide to transform it to the γ,δ-unsaturated carboxylic ester (2R,3R,E)-methyl 3-(4-bromo-2,6-dimethoxyphenyl)-2-(3-methylbut-3-enyl)hex-4-enoate:

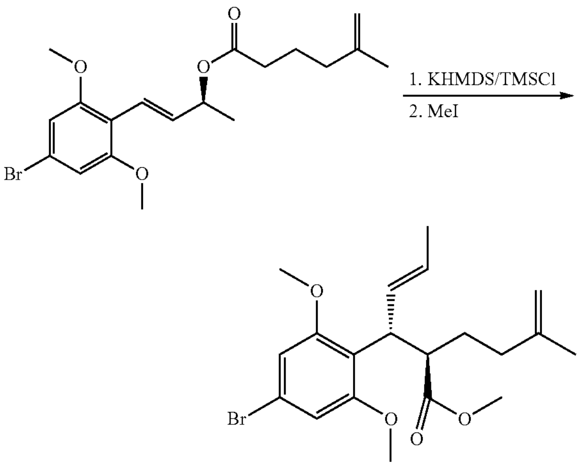

(d) contacting the γ,δ-unsaturated carboxylic acid ester of Formula (XXV) with an olefin metathesis catalyst to form a compound of Formula (I):

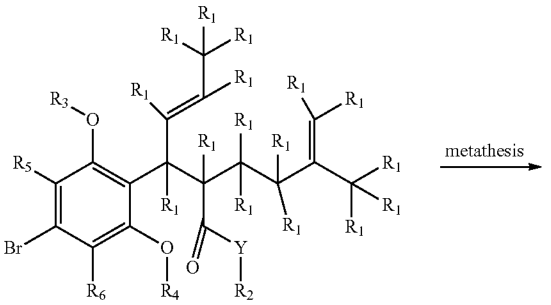

(XXV)

-continued

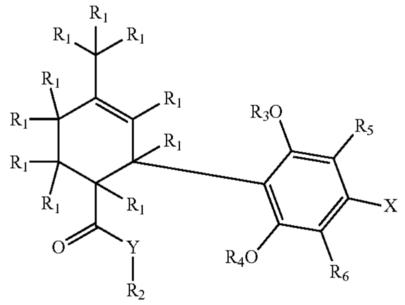

(I)

For example, the γ,δ-unsaturated carboxylic acid ester (2R,3R,E)-methyl 3-(4-bromo-2,6-dimethoxyphenyl)-2-(3-methylbut-3-enyl)hex-4-enoate was converted to (1R,2R)-methyl 2-(4-bromo-2,6-dimethoxyphenyl)-4-methylcyclohex-3-enecarboxylate by using $RuCl_2$(SIMes)($PCy_3$)(benzylidene) as the olefin metathesis catalyst:

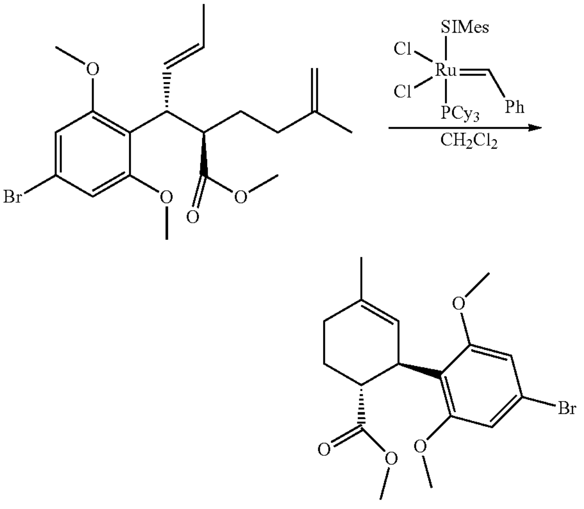

Accordingly, in some embodiments, the present disclosure relates to a process for the preparation of compounds of Formula (II), comprising reacting a compound of the Formula (I) with a $R_7$-M compound:

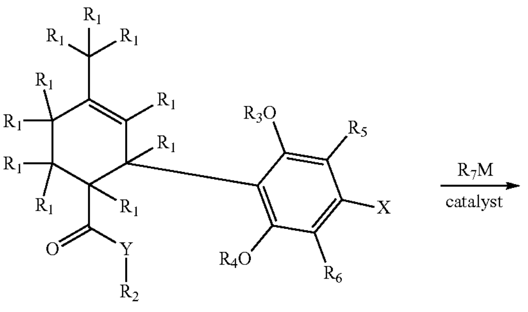

(I)

-continued

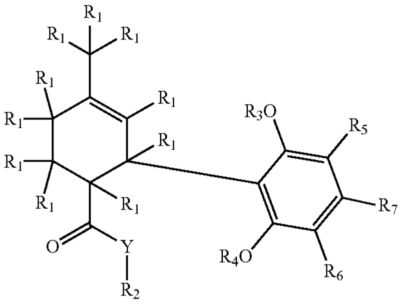

(II)

For example, (1R,2R)-methyl 2-(4-bromo-2,6-dimethoxyphenyl)-4-methylcyclohex-3-enecarboxylate is reacted with pentylzinc bromide in the presence of the catalyst $PdCl_2$(dppf) to form (1R,2R)-methyl 2-(2,6-dimethoxy-4-pentylphenyl)-4-methylcyclohex-3-enecarboxylate:

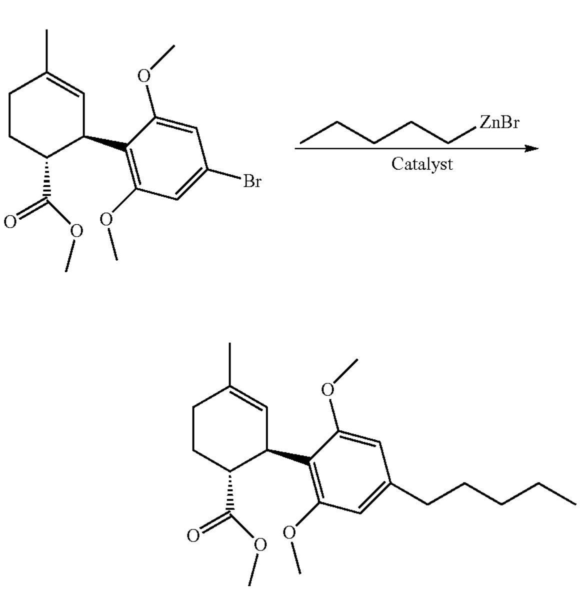

Accordingly, in some embodiments, the present disclosure relates to a process of (a) converting a compound of Formula (II) to a ketone of Formula (XXVI);

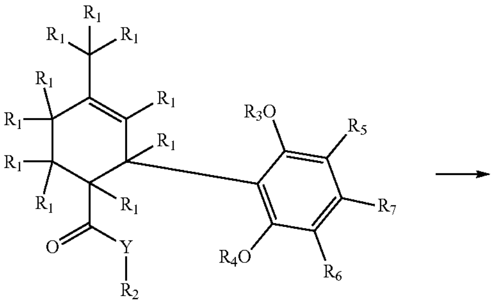

(II)

-continued

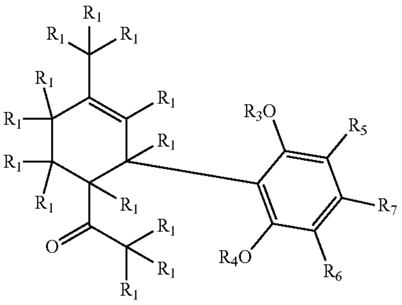

(XXVI)

For example, the Weinreb amide (1R,2R)-2-(2,6-dimethoxy-4-pentylphenyl)-N-methoxy-N,4-dimethylcyclohex-3-enecarboxamide is reacted with $CD_3MgI$ to form the ketone 1-((1R,2R)-2',6'-dimethoxy-5-methyl-4'-pentyl-1,2,3,4-tetrahydro-[1,1'-biphenyl]-2-yl)ethan-1-one-2,2,2-$d_3$;

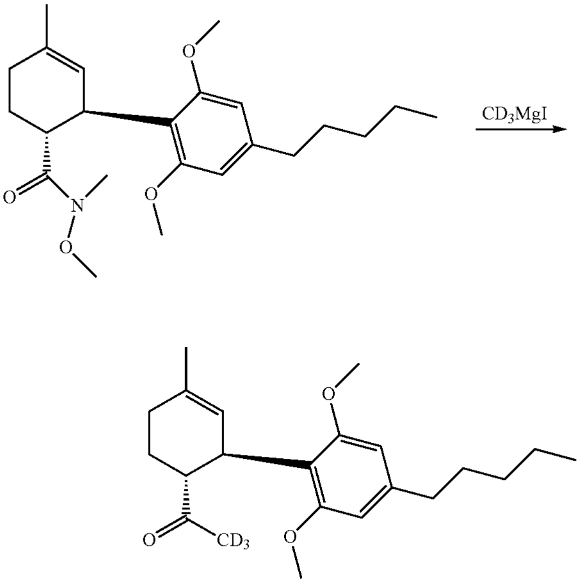

(b) reacting the ketone of Formula (XXVI) with a suitable Wittig reagent to form a compound of Formula (VII):

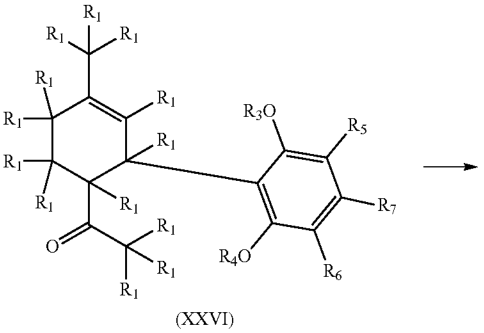

(XXVI)

-continued

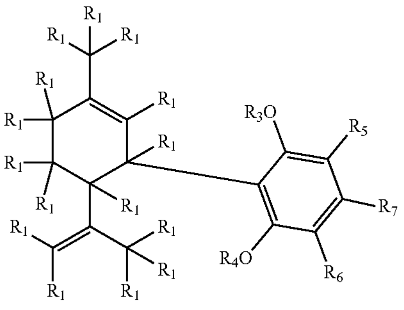

(VII)

For example, the ketone 1-((1R,2R)-2',6'-dimethoxy-5-methyl-4'-pentyl-1,2,3,4-tetrahydro-[1,1'-biphenyl]-2-yl) ethan-1-one-2,2,2-$d_3$ reacted with the Wittig reagent $d_3$-methyltriphenylphosphonium bromide to form the cannabinoid compound (1R,2R)-2',6'-dimethoxy-5-methyl-4'-pentyl-2-(prop-1-en-2-yl-$d_5$)-1,2,3,4-tetrahydro-1,1'-biphenyl.

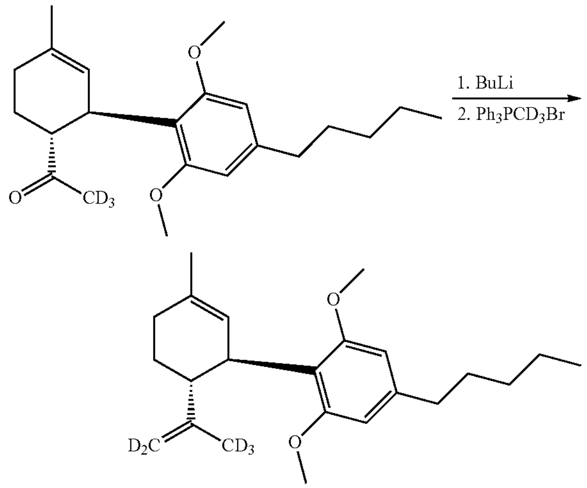

Accordingly, in some embodiments, the present disclosure relates to a process of (a) converting a compound of Formula (I) to a ketone of Formula (XXVII);

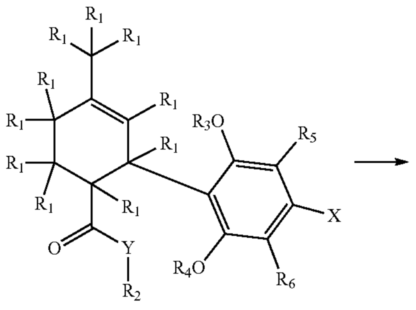

(I)

-continued

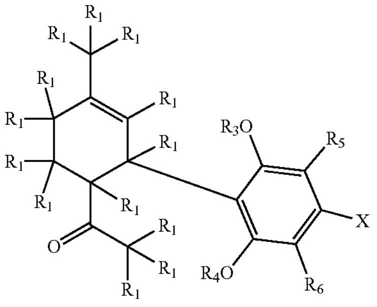

(XXVII)

for example, the Weinreb amide (1R,2R)-2-(4-bromo-2,6-dimethoxyphenyl)-N-methoxy-N,4-dimethylcyclohex-3-en-ecarboxamide is reacted with $CD_3MgI$ to form the ketone 1-((1R,2R)-4'-bromo-2',6'-dimethoxy-5-methyl-1,2,3,4-tetrahydro-[1,1'-biphenyl]-2-yl)ethan-1-one-2,2,2-$d_3$;

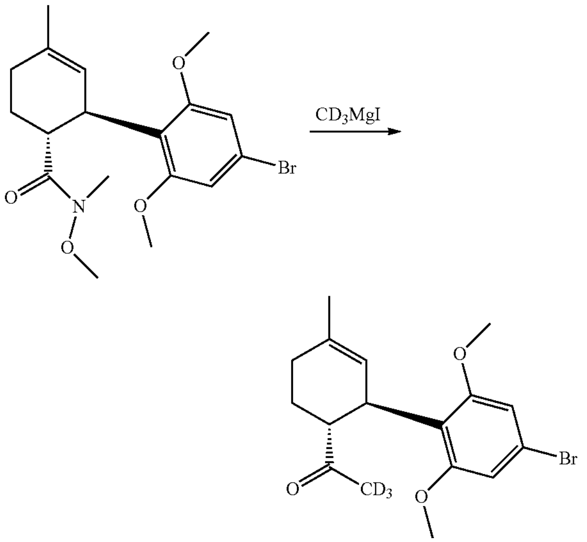

(b) reacting the ketone of Formula (XXVII) with a suitable Wittig reagent to form a compound of Formula (III):

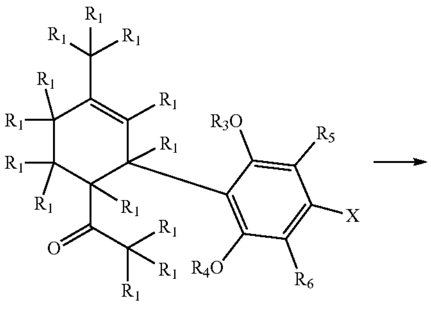

(XXVII)

-continued

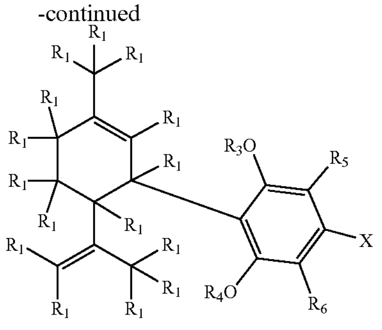

(III)

For example, the ketone 1-((1R,2R)-4'-bromo-2',6'-dimethoxy-5-methyl-1,2,3,4-tetrahydro-[1,1'-biphenyl]-2-yl)ethan-1-one-2,2,2-$d_3$ was reacted with the Wittig reagent $d_3$-methyltriphenylphosphonium bromide to form (1R,2R)-4'-bromo-2',6'-dimethoxy-5-methyl-2-(prop-1-en-2-yl-$d_5$)-1,2,3,4-tetrahydro-1,1'-biphenyl.

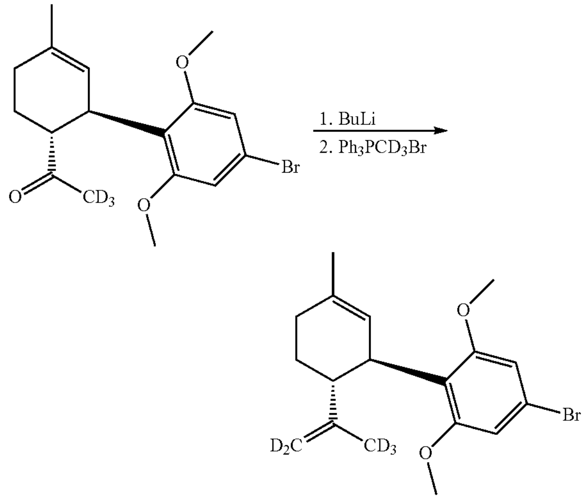

Accordingly, in some embodiments, the present disclosure relates to a process for the preparation of compounds of Formula (VII):

(VII)

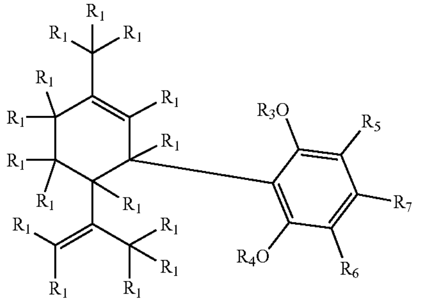

wherein, the $R_1$ groups are independently selected from the group consisting of hydrogen and deuterium, wherein at least one $R_1$ is deuterium;

$R_3$ to $R_4$ represents hydrogen, deuterium, a linear or branched alkyl group of any length, possibly substituted, or an alkenyl group of any length, possibly substituted, or an alkynyl group, possibly substituted, or a cycloalkyl group, possibly substituted, or an aryl group, possibly substituted, or an heteroaryl group, possibly substituted, or an acyl group, possibly substituted, and one or more of the carbon atoms in the alkyl, alkenyl, alkynyl, cycloalkyl, aryl, heteroaryl or acyl groups of $R_3$ to $R_4$ is optionally replaced with a heteroatom selected from the group consisting of O, S, N, P and Si, which, where possible, is optionally substituted with one or more groups;

$R_5$ and $R_6$ represents hydrogen, deuterium, halide, a linear or branched alkyl group of any length, possibly substituted, or an alkenyl group of any length, possibly substituted, or an alkynyl group, possibly substituted, or a cycloalkyl group, possibly substituted, or an aryl group, possibly substituted, or an heteroaryl group, possibly substituted, or an acyl group, possibly substituted, or a carboxylate group, possibly substituted, and one or more of the carbon atoms in the alkyl, alkenyl, alkynyl, cycloalkyl, aryl, heteroaryl, acyl or carboxylate groups of $R_5$ and/or $R_6$ is optionally replaced with a heteroatom selected from the group consisting of O, S, N, P and Si, which, where possible, is optionally substituted with one or more groups;

$R_7$ represents a hydrogen atom, a linear or branched alkyl group of any length, possibly substituted, or an alkenyl group of any length, possibly substituted, or an alkynyl group, possibly substituted, or a cycloalkyl group, possibly substituted, or an aryl group, possibly substituted;

comprising reacting a compound of the Formula (III) with a nucleophilic compound of the formula $R_7$-M,

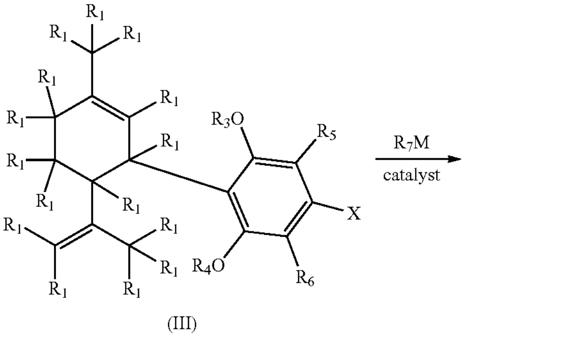

(III)

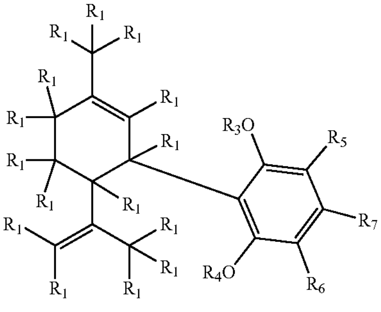

(VII)

wherein M is a leaving group, such as $B(OH)_2$, $B(OR)_2$, $BF_3K$, MgX, or ZnX (where X is halide such as bromide, chloride or iodide).

In one embodiment, the $R_1$ groups are independently selected from the group consisting of hydrogen and deuterium; and at least one $R_1$ is deuterium;

$R_3$ to $R_4$ represents hydrogen, deuterium, an optionally substituted $C_1$-$C_{20}$-alkyl group, an optionally substituted $C_2$-$C_{20}$-alkenyl group, an optionally substituted $C_2$-$C_{20}$-alkynyl group, an optionally substituted $C_3$-$C_{20}$-cycloalkyl group, an optionally substituted $C_6$-$C_{14}$-aryl group, an optionally substituted $C_5$-$C_{14}$-heteroaryl, an optionally substituted acyl group, and one or more of the carbon atoms in the alkyl, alkenyl, alkynyl, cycloalkyl, aryl, heteroaryl or acyl groups of $R_3$ to $R_4$ is optionally replaced with a heteroatom selected from the group consisting of O, S, N, P and Si, which, where possible, is optionally substituted, wherein the optional substituents are one or more groups selected from OH, halo and $C_1$-$C_6$-alkyl;

$R_5$ and $R_6$ represent hydrogen, deuterium, halide, an optionally substituted $C_1$-$C_{20}$-alkyl group, an optionally substituted $C_2$-$C_{20}$-alkenyl group, an optionally substituted $C_2$-$C_{20}$-alkynyl group, an optionally substituted $C_3$-$C_{20}$-cycloalkyl group, an optionally substituted $C_6$-$C_{14}$-aryl group, an optionally substituted $C_5$-$C_{14}$-heteroaryl, an optionally substituted acyl group, or an optionally substituted carboxylate group, and one or more of the carbon atoms in the alkyl, alkenyl, alkynyl, cycloalkyl, aryl, heteroaryl, acyl or carboxylate groups of $R_5$ and/or $R_6$ is optionally replaced with a heteroatom selected from the group consisting of O, S, N, P and Si, which, where possible, is optionally substituted, wherein the optional substituents are one or more groups selected from OH, halo and $C_1$-$C_6$-alkyl; and $R_7$ represents a hydrogen atom, an optionally substituted $C_1$-$C_{20}$-alkyl group, an optionally substituted $C_2$-$C_{20}$-alkenyl group, an optionally substituted $C_2$-$C_{20}$-alkynyl group, an optionally substituted $C_3$-$C_{20}$-cycloalkyl group, or an optionally substituted $C_6$-$C_{14}$-aryl group, wherein the optional substituents are one or more groups selected from OH, halo, $C_6$-aryl and $C_1$-$C_6$-alkyl.

In a general way, the compounds of Formula (VII) can be prepared and isolated prior to use.

For example, (1R,2R)-4'-bromo-2',6'-dimethoxy-5-methyl-2-(prop-1-en-2-yl-3-$^{13}$C-1,1-$d_2$)-1,2,3,4-tetrahydro-1,1'-biphenyl was reacted with pentylzinc bromide in the presence of the catalyst $PdCl_2$(dppf) to form the cannabinoid compound (1R,2R)-2',6'-dimethoxy-5-methyl-4'-pentyl-2-(prop-1-en-2-yl-3-$^{13}$C-1,1-$d_2$)-1,2,3,4-tetrahydro-1,1'-biphenyl:

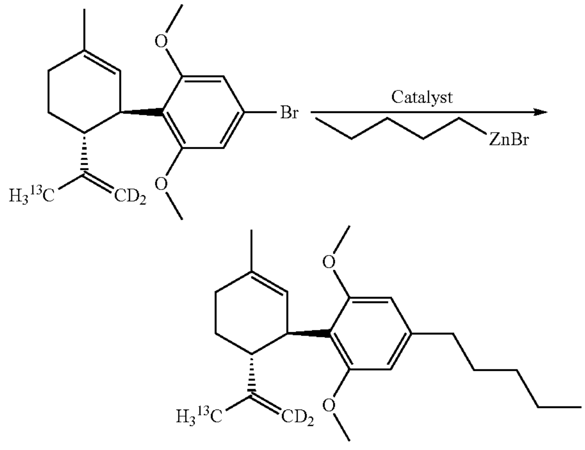

Accordingly, in some embodiments, the present disclosure relates to a process for the preparation of compounds of Formula (VIII):

(VIII)

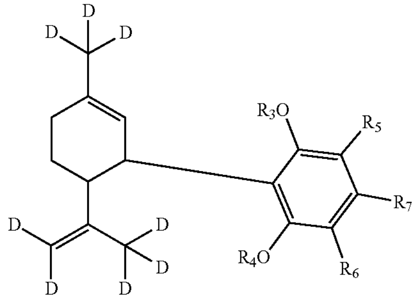

wherein, $R_3$ to $R_4$ represents hydrogen, deuterium, a linear or branched alkyl group of any length, possibly substituted, or an alkenyl group of any length, possibly substituted, or an alkynyl group, possibly substituted, or a cycloalkyl group, possibly substituted, or an aryl group, possibly substituted, or an heteroaryl group, possibly substituted, or an acyl group, possibly substituted, and one or more of the carbon atoms in the alkyl, alkenyl, alkynyl, cycloalkyl, aryl, heteroaryl or acyl groups of $R_3$ to $R_4$ is optionally replaced with a heteroatom selected from the group consisting of O, S, N, P and Si, which, where possible, is optionally substituted with one or more groups;

$R_5$ and $R_6$ represents hydrogen, deuterium, halide, a linear or branched alkyl group of any length, possibly substituted, or an alkenyl group of any length, possibly substituted, or an alkynyl group, possibly substituted, or a cycloalkyl group, possibly substituted, or an aryl group, possibly substituted, or an heteroaryl group, possibly substituted, or an acyl group, possibly substituted, or a carboxylate group, possibly substituted, and one or more of the carbon atoms in the alkyl, alkenyl, alkynyl, cycloalkyl, aryl, heteroaryl, acyl or carboxylate groups of $R_5$ and/or $R_6$ is optionally replaced with a heteroatom selected from the group consisting of O, S, N, P and Si, which, where possible, is optionally substituted with one or more groups;

$R_7$ represents a hydrogen atom, a linear or branched alkyl group of any length, possibly substituted, or an alkenyl group of any length, possibly substituted, or an alkynyl group, possibly substituted, or a cycloalkyl group, possibly substituted, or an aryl group, possibly substituted;

comprising reacting a compound of the formula

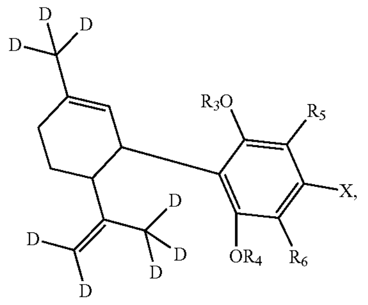

with a nucleophilic compound of the formula $R_7$-M where M is a leaving group.

In one embodiment, $R_3$ to $R_4$ represents hydrogen, deuterium, an optionally substituted $C_1$-$C_{20}$-alkyl group, an optionally substituted $C_2$-$C_{20}$-alkenyl group, an optionally substituted $C_2$-$C_{20}$-alkynyl group, an optionally substituted $C_3$-$C_{20}$-cycloalkyl group, an optionally substituted $C_6$-$C_{14}$-aryl group, an optionally substituted $C_6$-$C_{14}$-heteroaryl, an optionally substituted acyl group, and one or more of the carbon atoms in the alkyl, alkenyl, alkynyl, cycloalkyl, aryl, heteroaryl or acyl groups of $R_3$ to $R_4$ is optionally replaced with a heteroatom selected from the group consisting of O, S, N, P and Si, which, where possible, is optionally substituted, wherein the optional substituents are one or more groups selected from OH, halo and $C_1$-$C_6$-alkyl;

$R_5$ and $R_6$ represent hydrogen, deuterium, halide, an optionally substituted $C_1$-$C_{20}$-alkyl group, an optionally substituted $C_2$-$C_{20}$-alkenyl group, an optionally substituted $C_2$-$C_{20}$-alkynyl group, an optionally substituted $C_3$-$C_{20}$-cycloalkyl group, an optionally substituted $C_6$-$C_{14}$-aryl group, an optionally substituted $C_6$-$C_{14}$-heteroaryl, an optionally substituted acyl group, or an optionally substituted carboxylate group, and one or more of the carbon atoms in the alkyl, alkenyl, alkynyl, cycloalkyl, aryl, heteroaryl, acyl or carboxylate groups of $R_5$ and/or $R_6$ is optionally replaced with a heteroatom selected from the group consisting of O, S, N, P and Si, which, where possible, is optionally substituted, wherein the optional substituents are one or more groups selected from OH, halo and $C_1$-$C_6$-alkyl; and $R_7$ represents a hydrogen atom, an optionally substituted $C_1$-$C_{20}$-alkyl group, an optionally substituted $C_2$-$C_{20}$-alkenyl group, an optionally substituted $C_2$-$C_{20}$-alkynyl group, an optionally substituted $C_3$-$C_{20}$-cycloalkyl group, or an optionally substituted $C_6$-$C_{14}$-aryl group, wherein the optional substituents are one or more groups selected from OH, halo, $C_6$-aryl and $C_1$-$C_6$-alkyl.

In a general way, the compounds of Formula (VIII) can be prepared and isolated prior to use.

In a similar manner to compounds of Formula (VIII), the present disclosure relates to processes for preparing compounds of Formula (IX), Formula (X) and Formula (XI):

(IX)

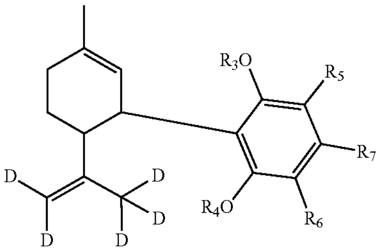

-continued (X)

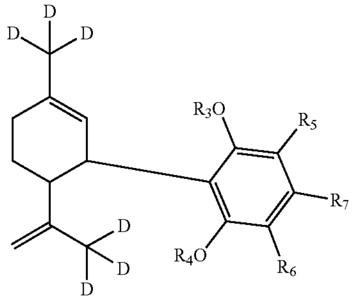

(XI)

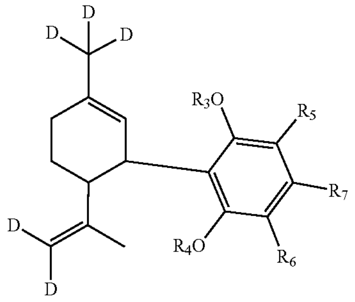

Comprising reacting compounds of the formulae

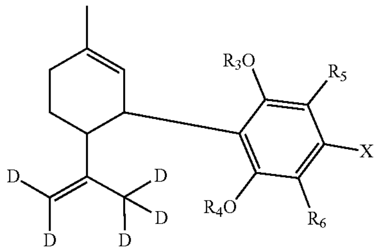

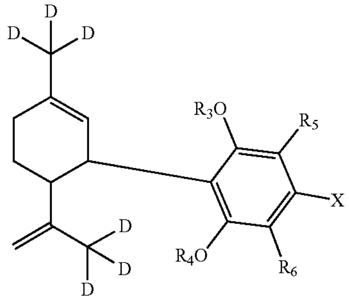

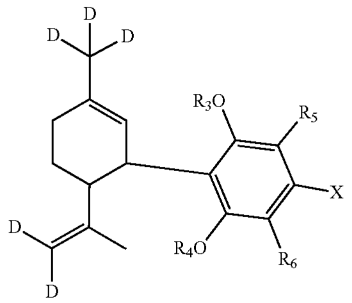

with a nucleophilic compound of the formula $R_7$-M where M is a leaving group.

wherein, $R_3$ to $R_4$ represents hydrogen, deuterium, a linear or branched alkyl group of any length, possibly substituted, or an alkenyl group of any length, possibly substituted, or an alkynyl group, possibly substituted, or a cycloalkyl group, possibly substituted, or an aryl group, possibly substituted, or an heteroaryl group, possibly substituted, or an acyl group, possibly substituted, and one or more of the carbon atoms in the alkyl, alkenyl, alkynyl, cycloalkyl, aryl, heteroaryl or acyl groups of $R_3$ to $R_4$ is optionally replaced with a heteroatom selected from the group consisting of O, S, N, P and Si, which, where possible, is optionally substituted with one or more groups;

$R_5$ and $R_6$ represents hydrogen, deuterium, halide, a linear or branched alkyl group of any length, possibly substituted, or an alkenyl group of any length, possibly substituted, or an alkynyl group, possibly substituted, or a cycloalkyl group, possibly substituted, or an aryl group, possibly substituted, or an heteroaryl group, possibly substituted, or an acyl group, possibly substituted, or a carboxylate group, possibly substituted, and one or more of the carbon atoms in the alkyl, alkenyl, alkynyl, cycloalkyl, aryl, heteroaryl, acyl or carboxylate groups of $R_5$ and/or $R_6$ is optionally replaced with a heteroatom selected from the group consisting of O, S, N, P and Si, which, where possible, is optionally substituted with one or more groups;

$R_7$ represents a hydrogen atom, a linear or branched alkyl group of any length, possibly substituted, or an alkenyl group of any length, possibly substituted, or an alkynyl group, possibly substituted, or a cycloalkyl group, possibly substituted, or an aryl group, possibly substituted.

In one embodiment, $R_3$ to $R_4$ represents hydrogen, deuterium, an optionally substituted $C_1$-$C_{20}$-alkyl group, an optionally substituted $C_2$-$C_{20}$-alkenyl group, an optionally substituted $C_2$-$C_{20}$-alkynyl group, an optionally substituted $C_3$-$C_{20}$-cycloalkyl group, an optionally substituted $C_6$-$C_{14}$-aryl group, an optionally substituted $C_5$-$C_{14}$-heteroaryl, an optionally substituted acyl group, and one or more of the carbon atoms in the alkyl, alkenyl, alkynyl, cycloalkyl, aryl, heteroaryl or acyl groups of $R_3$ to $R_4$ is optionally replaced with a heteroatom selected from the group consisting of O, S, N, P and Si, which, where possible, is optionally substituted, wherein the optional substituents are one or more groups selected from OH, halo and $C_1$-$C_6$-alkyl;

$R_5$ and $R_6$ represent hydrogen, deuterium, halide, an optionally substituted $C_1$-$C_{20}$-alkyl group, an optionally substituted $C_2$-$C_{20}$-alkenyl group, an optionally substituted $C_2$-$C_{20}$-alkynyl group, an optionally substituted $C_3$-$C_{20}$-cycloalkyl group, an optionally substituted $C_6$-$C_{14}$-aryl group, an optionally substituted $C_6$-$C_{14}$-heteroaryl, an optionally substituted acyl group, or an optionally substituted carboxylate group, and one or more of the carbon atoms in the alkyl, alkenyl, alkynyl, cycloalkyl, aryl, heteroaryl, acyl or carboxylate groups of $R_5$ and/or $R_6$ is optionally replaced with a heteroatom selected from the group consisting of O, S, N, P and Si, which, where possible, is optionally substituted, wherein the optional substituents are one or more groups selected from OH, halo and $C_1$-$C_6$-alkyl; and $R_7$ represents a hydrogen atom, an optionally substituted $C_1$-$C_{20}$-alkyl group, an optionally substituted $C_2$-$C_{20}$-alkenyl group, an optionally substituted $C_2$-$C_{20}$-alkynyl group, an optionally substituted $C_3$-$C_{20}$-cycloalkyl group, or an optionally substituted $C_6$-$C_{14}$-aryl group, wherein the optional substituents are one or more groups selected from OH, halo, $C_6$-aryl and $C_1$-$C_6$-alkyl.

In a general way, the compounds of Formula (IX), Formula (X) and Formula (XI) can be prepared and isolated prior to use.

In a similar manner to compounds of Formula (VIII), the present disclosure relates to processes for the preparation of compounds of Formula (XII), Formula (XIII) and Formula (XIV):

(XII)

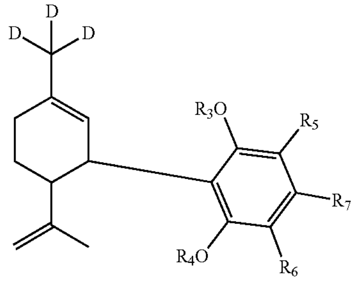

(XIII)

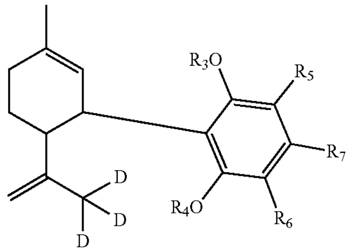

(XIV)

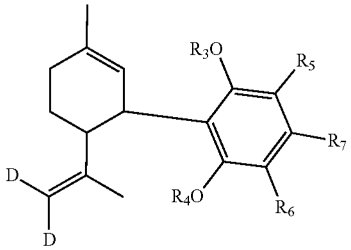

Comprising reacting compounds of formulae

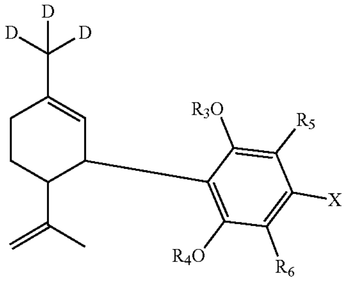

-continued

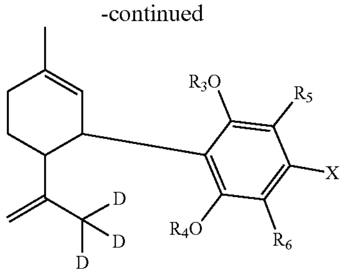

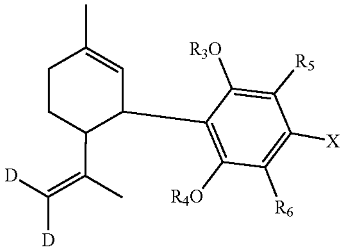

with a nucleophilic compound of the formula $R_7$-M where M is a leaving group.

wherein, $R_3$ to $R_4$ represents hydrogen, deuterium, a linear or branched alkyl group of any length, possibly substituted, or an alkenyl group of any length, possibly substituted, or an alkynyl group, possibly substituted, or a cycloalkyl group, possibly substituted, or an aryl group, possibly substituted, or an heteroaryl group, possibly substituted, or an acyl group, possibly substituted, and one or more of the carbon atoms in the alkyl, alkenyl, alkynyl, cycloalkyl, aryl, heteroaryl or acyl groups of $R_3$ to $R_4$ is optionally replaced with a heteroatom selected from the group consisting of O, S, N, P and Si, which, where possible, is optionally substituted with one or more groups;

$R_5$ and $R_6$ represents hydrogen, deuterium, halide, a linear or branched alkyl group of any length, possibly substituted, or an alkenyl group of any length, possibly substituted, or an alkynyl group, possibly substituted, or a cycloalkyl group, possibly substituted, or an aryl group, possibly substituted, or an heteroaryl group, possibly substituted, or an acyl group, possibly substituted, or a carboxylate group, possibly substituted, and one or more of the carbon atoms in the alkyl, alkenyl, alkynyl, cycloalkyl, aryl, heteroaryl, acyl or carboxylate groups of $R_5$ and/or $R_6$ is optionally replaced with a heteroatom selected from the group consisting of O, S, N, P and Si, which, where possible, is optionally substituted with one or more groups;

$R_7$ represents a hydrogen atom, a linear or branched alkyl group of any length, possibly substituted, or an alkenyl group of any length, possibly substituted, or an alkynyl group, possibly substituted, or a cycloalkyl group, possibly substituted, or an aryl group, possibly substituted.

In one embodiment, $R_3$ to $R_4$ represents hydrogen, deuterium, an optionally substituted $C_1$-$C_{20}$-alkyl group, an optionally substituted $C_2$-$C_{20}$-alkenyl group, an optionally substituted $C_2$-$C_{20}$-alkynyl group, an optionally substituted $C_3$-$C_{20}$-cycloalkyl group, an optionally substituted $C_6$-$C_{14}$-aryl group, an optionally substituted $C_6$-$C_{14}$-heteroaryl, an optionally substituted acyl group, and one or more of the carbon atoms in the alkyl, alkenyl, alkynyl, cycloalkyl, aryl, heteroaryl or acyl groups of $R_3$ to $R_4$ is optionally replaced with a heteroatom selected from the group consisting of O, S, N, P and Si, which, where possible, is optionally substituted, wherein the optional substituents are one or more groups selected from OH, halo and $C_1$-$C_6$-alkyl;

$R_5$ and $R_6$ represent hydrogen, deuterium, halide, an optionally substituted $C_1$-$C_{20}$-alkyl group, an optionally substituted $C_2$-$C_{20}$-alkenyl group, an optionally substituted $C_2$-$C_{20}$-alkynyl group, an optionally substituted $C_3$-$C_{20}$-cycloalkyl group, an optionally substituted $C_6$-$C_{14}$-aryl group, an optionally substituted $C_6$-$C_{14}$-heteroaryl, an optionally substituted acyl group, or an optionally substituted carboxylate group, and one or more of the carbon atoms in the alkyl, alkenyl, alkynyl, cycloalkyl, aryl, heteroaryl, acyl or carboxylate groups of $R_5$ and/or $R_6$ is optionally replaced with a heteroatom selected from the group consisting of O, S, N, P and Si, which, where possible, is optionally substituted, wherein the optional substituents are one or more groups selected from OH, halo and $C_1$-$C_6$-alkyl; and $R_7$ represents a hydrogen atom, an optionally substituted $C_1$-$C_{20}$-alkyl group, an optionally substituted $C_2$-$C_{20}$-alkenyl group, an optionally substituted $C_2$-$C_{20}$-alkynyl group, an optionally substituted $C_3$-$C_{20}$-cycloalkyl group, or an optionally substituted $C_6$-$C_{14}$-aryl group, wherein the optional substituents are one or more groups selected from OH, halo, $C_6$-aryl and $C_1$-$C_6$-alkyl.

In a general way, the compounds of Formula (XII), Formula (XIII) and Formula (XIV) can be prepared and isolated prior to use.

Accordingly, in some embodiments, the present disclosure relates to a process for the preparation of compounds of Formula (XV), comprising contacting a compound of Formula (II) with a compound of Formula $(R_1)_3C$-M (M=Li, MgX; where X=halide, such as chloride, bromide, iodide):

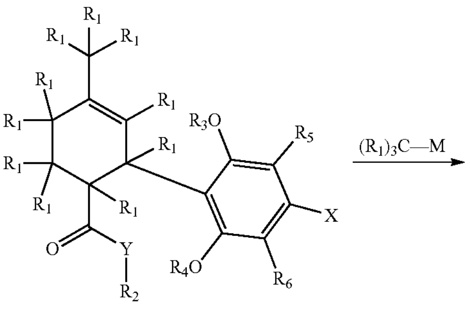

(II)

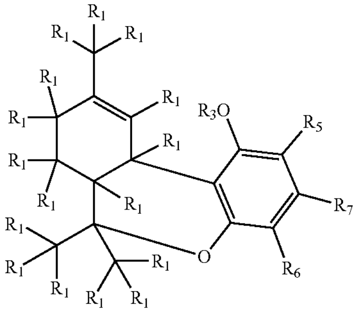

(XV)

wherein, the $R_1$ groups are independently selected from the group consisting of hydrogen and deuterium;

$R_3$ represents hydrogen, deuterium, a linear or branched alkyl group of any length, possibly substituted, or an alkenyl group of any length, possibly substituted, or an alkynyl group, possibly substituted, or a cycloalkyl group, possibly substituted, or an aryl group, possibly substituted, or an heteroaryl group, possibly substituted, or an acyl group, possibly substituted, and one or more of the carbon atoms in the alkyl, alkenyl, alkynyl, cycloalkyl, aryl, heteroaryl or acyl groups of $R_3$ is optionally replaced with a heteroatom selected from the group consisting of O, S, N, P and Si, which, where possible, is optionally substituted with one or more groups;

$R_5$ and $R_6$ represents hydrogen, deuterium, halide, a linear or branched alkyl group of any length, possibly substituted, or an alkenyl group of any length, possibly substituted, or an alkynyl group, possibly substituted, or a cycloalkyl group, possibly substituted, or an aryl group, possibly substituted, or an heteroaryl group, possibly substituted, or an acyl group, possibly substituted, or a carboxylate group, possibly substituted, and one or more of the carbon atoms in the alkyl, alkenyl, alkynyl, cycloalkyl, aryl, heteroaryl, acyl or carboxylate groups of $R_5$ and/or $R_6$ is optionally replaced with a heteroatom selected from the group consisting of O, S, N, P and Si, which, where possible, is optionally substituted with one or more groups; and $R_7$ represents a hydrogen atom, a linear or branched alkyl group of any length, possibly substituted, or an alkenyl group of any length, possibly substituted, or an alkynyl group, possibly substituted, or a cycloalkyl group, possibly substituted, or an aryl group, possibly substituted.

In one embodiment, the $R_1$ groups are independently selected from the group consisting of hydrogen and deuterium; and at least one $R_1$ is deuterium;

$R_3$ represents hydrogen, deuterium, an optionally substituted $C_1$-$C_{20}$-alkyl group, an optionally substituted $C_2$-$C_{20}$-alkenyl group, an optionally substituted $C_2$-$C_{20}$-alkynyl group, an optionally substituted $C_3$-$C_{20}$-cycloalkyl group, an optionally substituted $C_6$-$C_{14}$-aryl group, an optionally substituted $C_5$-$C_{14}$-heteroaryl, an optionally substituted acyl group, and one or more of the carbon atoms in the alkyl, alkenyl, alkynyl, cycloalkyl, aryl, heteroaryl or acyl groups of $R_3$ is optionally replaced with a heteroatom selected from the group consisting of O, S, N, P and Si, which, where possible, is optionally substituted, wherein the optional substituents are one or more groups selected from OH, halo and $C_1$-$C_6$-alkyl; Y represents O or $NR^c$, in which $R^c$ is a hydrogen atom, $C_1$-$C_6$-alkyl, $C_3$-$C_6$-cycloalkyl, $C_6$-$C_{10}$-aryl or $C_2$-$C_6$-alkenyl group;

$R_5$ and $R_6$ represent hydrogen, deuterium, halide, an optionally substituted $C_1$-$C_{20}$-alkyl group, an optionally substituted $C_2$-$C_{20}$-alkenyl group, an optionally substituted $C_2$-$C_{20}$-alkynyl group, an optionally substituted $C_3$-$C_{20}$-cycloalkyl group, an optionally substituted $C_6$-$C_{14}$-aryl group, an optionally substituted $C_5$-$C_{14}$-heteroaryl, an optionally substituted acyl group, or an optionally substituted carboxylate group, and one or more of the carbon atoms in the alkyl, alkenyl, alkynyl, cycloalkyl, aryl, heteroaryl, acyl or carboxylate groups of $R_5$ and/or $R_6$ is optionally replaced with a heteroatom selected from the group consisting of O, S, N, P and Si, which, where possible, is optionally substituted, wherein the optional substituents are one or more groups selected from OH, halo and $C_1$-$C_6$-alkyl; and $R_7$ represents a hydrogen atom, an optionally substituted $C_1$-$C_{20}$-alkyl group, an optionally substituted $C_2$-$C_{20}$-alkenyl group, an optionally substituted $C_2$-$C_{20}$-alkynyl group, an optionally substituted $C_3$-$C_{20}$-cycloalkyl group, or an optionally substituted $C_6$-$C_{14}$-aryl group, wherein the optional substituents are one or more groups selected from OH, halo, $C_6$-aryl and $C_1$-$C_6$-alkyl.

In a general way, the compounds of Formula (XV) can be prepared and isolated prior to use.

In one embodiment, at least one of the carbon-12 atoms in the cyclohexene ring and substituents of Formula (XV) is replaced with a carbon-13 or carbon-14 atom.

For example, (1R,2R)-methyl 2-(2,6-dimethoxy-4-pentylphenyl)-4-methylcyclohex-3-enecarboxylate is reacted with $CD_3MgI$ followed by addition of a Lewis acid such as $ZnBr_2$, or a protic acid such as $H_2SO_4$, to form (6aR)-9-methyl-6,6-bis(methyl-d$_3$)-3-pentyl-6a,7,8,10a-tetrahydro-6H-benzo[c]chromen-1-ol.

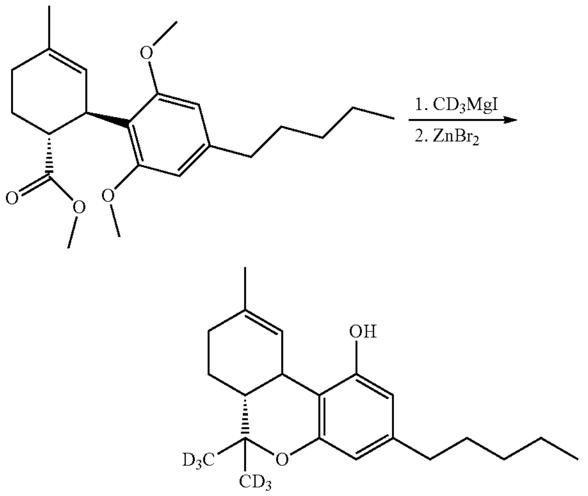

Accordingly, in some embodiments, the present disclosure relates to a process for the preparation of compounds of Formula (XVI):

(XVI)

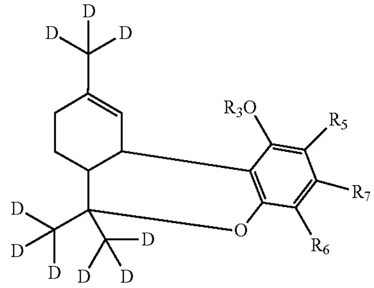

by contacting a compound of the formula

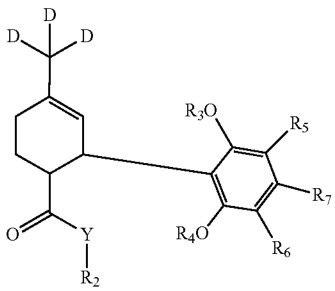

with $CD_3M$ (M=Li or MgX; X=halide such as chloride, bromide, iodide), followed by contacting with a Lewis acid or a protic acid, wherein, $R_3$ represents hydrogen, deuterium, a linear or branched alkyl group of any length, possibly substituted, or an alkenyl group of any length, possibly substituted, or an alkynyl group, possibly substituted, or a cycloalkyl group, possibly substituted, or an aryl group, possibly substituted, or an heteroaryl group, possibly substituted, or an acyl group, possibly substituted, and one or more of the carbon atoms in the alkyl, alkenyl, alkynyl, cycloalkyl, aryl, heteroaryl or acyl groups of $R_3$ is optionally replaced with a heteroatom selected from the group consisting of O, S, N, P and Si, which, where possible, is optionally substituted with one or more groups;

$R_5$ and $R_6$ represents hydrogen, deuterium, halide, a linear or branched alkyl group of any length, possibly substituted, or an alkenyl group of any length, possibly substituted, or an alkynyl group, possibly substituted, or a cycloalkyl group, possibly substituted, or an aryl group, possibly substituted, or an heteroaryl group, possibly substituted, or an acyl group, possibly substituted, or a carboxylate group, possibly substituted, and one or more of the carbon atoms in the alkyl, alkenyl, alkynyl, cycloalkyl, aryl, heteroaryl, acyl or carboxylate groups of $R_5$ and/or $R_6$ is optionally replaced with a heteroatom selected from the group consisting of O, S, N, P and Si, which, where possible, is optionally substituted with one or more groups;

$R_7$ represents a hydrogen atom, a linear or branched alkyl group of any length, possibly substituted, or an alkenyl group of any length, possibly substituted, or an alkynyl group, possibly substituted, or a cycloalkyl group, possibly substituted, or an aryl group, possibly substituted.

In one embodiment, $R_3$ represents hydrogen, deuterium, an optionally substituted $C_1$-$C_{20}$-alkyl group, an optionally substituted $C_2$-$C_{20}$-alkenyl group, an optionally substituted $C_2$-$C_{20}$-alkynyl group, an optionally substituted $C_3$-$C_{20}$-cycloalkyl group, an optionally substituted $C_6$-$C_{14}$-aryl group, an optionally substituted $C_5$-$C_{14}$-heteroaryl, an optionally substituted acyl group, and one or more of the carbon atoms in the alkyl, alkenyl, alkynyl, cycloalkyl, aryl, heteroaryl or acyl groups of $R_3$ is optionally replaced with a heteroatom selected from the group consisting of O, S, N, P and Si, which, where possible, is optionally substituted, wherein the optional substituents are one or more groups selected from OH, halo and $C_1$-$C_6$-alkyl;

Y represents O or $NR^c$, in which $R^c$ is a hydrogen atom, $C_1$-$C_6$-alkyl, $C_3$-$C_6$-cycloalkyl, $C_6$-$C_{10}$-aryl or $C_2$-$C_6$-alkenyl group;

$R_5$ and $R_6$ represent hydrogen, deuterium, halide, an optionally substituted $C_1$-$C_{20}$-alkyl group, an optionally substituted $C_2$-$C_{20}$-alkenyl group, an optionally substituted $C_2$-$C_{20}$-alkynyl group, an optionally substituted $C_3$-$C_{20}$-cycloalkyl group, an optionally substituted $C_6$-$C_{14}$-aryl group, an optionally substituted $C_5$-$C_{14}$-heteroaryl, an optionally substituted acyl group, or an optionally substituted carboxylate group, and one or more of the carbon atoms in the alkyl, alkenyl, alkynyl, cycloalkyl, aryl, heteroaryl, acyl or carboxylate groups of $R_5$ and/or $R_6$ is optionally replaced with a heteroatom selected from the group consisting of O, S, N, P and Si, which, where possible, is optionally substituted, wherein the optional substituents are one or more groups selected from OH, halo and $C_1$-$C_6$-alkyl; and $R_7$ represents a hydrogen atom, an optionally substituted $C_1$-$C_{20}$-alkyl group, an optionally substituted $C_2$-$C_{20}$-alkenyl group, an optionally substituted $C_2$-$C_{20}$-alkynyl group, an optionally substituted $C_3$-$C_{20}$-cycloalkyl group, or an optionally substituted $C_6$-$C_{14}$-aryl group, wherein the optional substituents are one or more groups selected from OH, halo, $C_6$-aryl and $C_1$-$C_6$-alkyl.

In a general way, the compounds of Formula (XVI) can be prepared and isolated prior to use.

Accordingly, in some embodiments, the present disclosure relates to a process for the preparation of compounds of Formula (XVII) and Formula (XVIII):

(XVII)

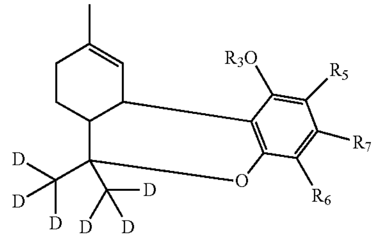

(XVIII)

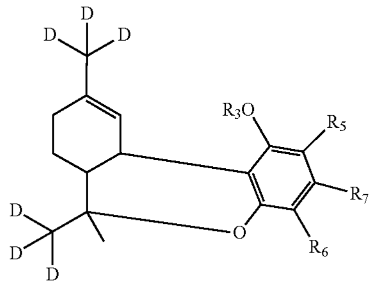

by contacting compounds of the formulae:

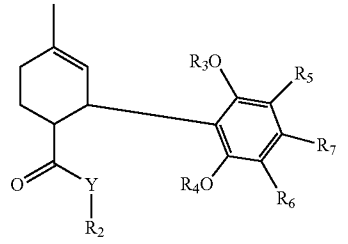

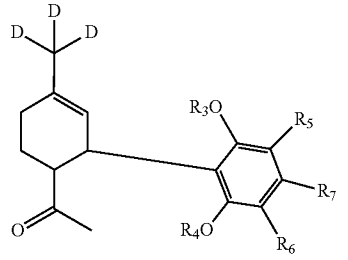

with $CD_3M$ (M=Li or MgX; X=halide such as chloride, bromide, iodide), followed by contacting with a Lewis acid or a protic acid, wherein, $R_3$ represents hydrogen, deuterium, a linear or branched alkyl group of any length, possibly substituted, or an alkenyl group of any length, possibly substituted, or an alkynyl group, possibly substituted, or a cycloalkyl group, possibly substituted, or an aryl group, possibly substituted, or an heteroaryl group, possibly substituted, or an acyl group, possibly substituted, and one or more of the carbon atoms in the alkyl, alkenyl, alkynyl, cycloalkyl, aryl, heteroaryl or acyl groups of $R_3$ is optionally replaced with a heteroatom selected from the group consisting of O, S, N, P and Si, which, where possible, is optionally substituted with one or more groups;

$R_5$ and $R_6$ represents hydrogen, deuterium, halide, a linear or branched alkyl group of any length, possibly substituted, or an alkenyl group of any length, possibly substituted, or an alkynyl group, possibly substituted, or a cycloalkyl group, possibly substituted, or an aryl group, possibly substituted, or an heteroaryl group, possibly substituted, or an acyl group, possibly substituted, or a carboxylate group, possibly substituted, and one or more of the carbon atoms in the alkyl, alkenyl, alkynyl, cycloalkyl, aryl, heteroaryl, acyl or carboxylate groups of $R_5$ and/or $R_6$ is optionally replaced with a heteroatom selected from the group consisting of O, S, N, P and Si, which, where possible, is optionally substituted with one or more groups;

$R_7$ represents a hydrogen atom, a linear or branched alkyl group of any length, possibly substituted, or an alkenyl group of any length, possibly substituted, or an alkynyl group, possibly substituted, or a cycloalkyl group, possibly substituted, or an aryl group, possibly substituted.

In one embodiment, $R_3$ represents hydrogen, deuterium, an optionally substituted $C_1$-$C_{20}$-alkyl group, an optionally substituted $C_2$-$C_{20}$-alkenyl group, an optionally substituted $C_2$-$C_{20}$-alkynyl group, an optionally substituted $C_3$-$C_{20}$-cycloalkyl group, an optionally substituted $C_6$-$C_{14}$-aryl group, an optionally substituted $C_5$-$C_{14}$-heteroaryl, an optionally substituted acyl group, and one or more of the carbon atoms in the alkyl, alkenyl, alkynyl, cycloalkyl, aryl, heteroaryl or acyl groups of $R_3$ is optionally replaced with a heteroatom selected from the group consisting of O, S, N, P and Si, which, where possible, is optionally substituted, wherein the optional substituents are one or more groups selected from OH, halo and $C_1$-$C_6$-alkyl;

Y represents O or $NR^c$, in which $R^c$ is a hydrogen atom, $C_1$-$C_6$-alkyl, $C_3$-$C_6$-cycloalkyl, $C_6$-$C_{10}$-aryl or $C_2$-$C_6$-alkenyl group;

$R_5$ and $R_6$ represent hydrogen, deuterium, halide, an optionally substituted $C_1$-$C_{20}$-alkyl group, an optionally substituted $C_2$-$C_{20}$-alkenyl group, an optionally substituted $C_2$-$C_{20}$-alkynyl group, an optionally substituted $C_3$-$C_{20}$-cycloalkyl group, an optionally substituted $C_6$-$C_{14}$-aryl group, an optionally substituted $C_5$-$C_{14}$-heteroaryl, an optionally substituted acyl group, or an optionally substituted carboxylate group, and one or more of the carbon atoms in the alkyl, alkenyl, alkynyl, cycloalkyl, aryl, heteroaryl, acyl or carboxylate groups of $R_5$ and/or $R_6$ is optionally replaced with a heteroatom selected from the group consisting of O, S, N, P and Si, which, where possible, is optionally substituted, wherein the optional substituents are one or more groups selected from OH, halo and $C_1$-$C_6$-alkyl; and $R_7$ represents a hydrogen atom, an optionally substituted $C_1$-$C_{20}$-alkyl group, an optionally substituted $C_2$-$C_{20}$-alkenyl group, an optionally substituted $C_2$-$C_{20}$-alkynyl group, an optionally substituted $C_3$-$C_{20}$-cycloalkyl group, or an optionally substituted $C_6$-$C_{14}$-aryl group, wherein the optional substituents are one or more groups selected from OH, halo, $C_6$-aryl and $C_1$-$C_6$-alkyl.

In a general way, the compounds of Formula (XVII) and Formula (XVIII) can be prepared and isolated prior to use.

Accordingly, in some embodiments, the present disclosure relates to a process for the preparation of compounds of Formula (XIX) and Formula (XX):

(XIX)

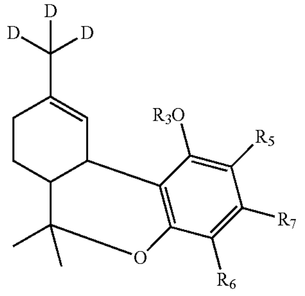

(XX)

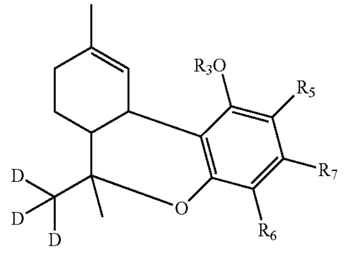

by contacting compounds of the formulae:

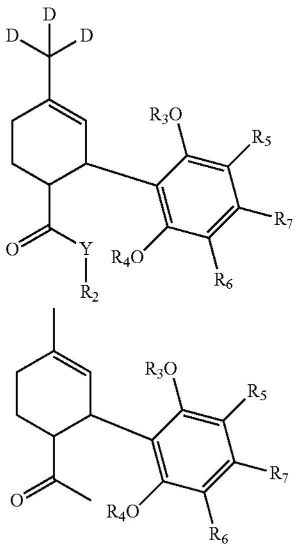

with $CH_3M$ or $CD_3M$ (M=Li or MgX; X=halide such as chloride, bromide, iodide), followed by contacting with a Lewis acid or a protic acid, wherein, $R_3$ represents hydrogen, deuterium, a linear or branched alkyl group of any length, possibly substituted, or an alkenyl group of any length, possibly substituted, or an alkynyl group, possibly substituted, or a cycloalkyl group, possibly substituted, or an aryl group, possibly substituted, or an heteroaryl group, possibly substituted, or an acyl group, possibly substituted, and one or more of the carbon atoms in the alkyl, alkenyl, alkynyl, cycloalkyl, aryl, heteroaryl or acyl groups of $R_3$ is optionally replaced with a heteroatom selected from the group consisting of O, S, N, P and Si, which, where possible, is optionally substituted with one or more groups;

$R_5$ and $R_6$ represents hydrogen, deuterium, halide, a linear or branched alkyl group of any length, possibly substituted, or an alkenyl group of any length, possibly substituted, or an alkynyl group, possibly substituted, or a cycloalkyl group, possibly substituted, or an aryl group, possibly substituted, or an heteroaryl group, possibly substituted, or an acyl group, possibly substituted, or a carboxylate group, possibly substituted, and one or more of the carbon atoms in the alkyl, alkenyl, alkynyl, cycloalkyl, aryl, heteroaryl, acyl or carboxylate groups of $R_5$ and/or $R_6$ is optionally replaced with a heteroatom selected from the group consisting of O, S, N, P and Si, which, where possible, is optionally substituted with one or more groups;

$R_7$ represents a hydrogen atom, a linear or branched alkyl group of any length, possibly substituted, or an alkenyl group of any length, possibly substituted, or an alkynyl group, possibly substituted, or a cycloalkyl group, possibly substituted, or an aryl group, possibly substituted.

In one embodiment, the alkyl groups of any length in any of the above Formulas in the processes is optionally substituted $C_1$-$C_{20}$-alkyl. In another embodiment, the alkyl group is optionally substituted $C_1$-$C_{10}$-alkyl. In another embodiment, the alkyl group is optionally substituted $C_1$-$C_6$-alkyl. In another embodiment, the alkyl group is methyl, ethyl, propyl, butyl or pentyl. In another embodiment, the optional substituents are hydroxyl, halo or $C_1$-$C_6$-alkyl.

In one embodiment, the alkenyl groups of any length in any of the above Formulas in the processes is optionally substituted $C_2$-$C_{20}$-alkenyl. In another embodiment, the alkenyl group is optionally substituted $C_2$-$C_{10}$-alkenyl. In another embodiment, the alkenyl group is optionally substituted $C_2$-$C_6$-alkenyl. In another embodiment, the alkenyl group is ethenyl, propenyl, butenyl or pentenyl. In another embodiment, the optional substituents are hydroxyl, halo or $C_1$-$C_6$-alkyl.

In one embodiment, the alkynyl groups of any length in any of the above Formulas in the processes is optionally substituted $C_2$-$C_{20}$-alkynyl. In another embodiment, the alkynyl group is optionally substituted $C_2$-$C_{10}$-alkynyl. In another embodiment, the alkynyl group is optionally substituted $C_2$-$C_6$-alkynyl. In another embodiment, the alkynyl group is ethynyl, propynyl, butynyl or pentynyl. In another embodiment, the optional substituents are hydroxyl, halo or $C_1$-$C_6$-alkyl.

In one embodiment, the cycloalkyl groups in any of the above Formulas in the processes is optionally substituted $C_3$-$C_{20}$-cycloalkyl. In another embodiment, the cycloalkyl group is optionally substituted $C_3$-$C_{10}$-cycloalkyl. In another embodiment, the cycloalkyl group is optionally substituted $C_3$-$C_6$-cycloalkyl. In another embodiment, the cycloalkyl group is cyclopropyl, cyclobutyl or cyclopentyl. In another embodiment, the optional substituents are hydroxyl, halo or $C_1$-$C_6$-alkyl.

In one embodiment, the aryl groups in any of the above Formulas in the processes is optionally substituted $C_6$-$C_{14}$-aryl. In another embodiment, the aryl group is optionally substituted $C_6$-$C_{10}$-aryl, or phenyl. In another embodiment, the aryl group is phenyl, naphthyl, tetrahydronaphthyl, phenanthrenyl, biphenylenyl, indanyl, or indenyl and the like. In another embodiment, the optional substituents are hydroxyl, halo or $C_1$-$C_6$-alkyl.

In one embodiment, the heteroaryl groups in any of the above Formulas in the processes is optionally substituted $C_5$-$C_{14}$-heteroaryl. In another embodiment, the heteroaryl group is optionally substituted $C_5$-$C_{10}$-heteroaryl, or $C_5$-$C_6$-heteroaryl. In another embodiment, the heteroaryl group is benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, quinolinyl, quinazolinyl, triazolyl, thiazolyl, thiophenyl, tetrahydroindolyl, tetrazolyl, thiadiazolyl, thienyl, triazolyl and the like. In another embodiment, the optional substituents are hydroxyl, halo or $C_1$-$C_6$-alkyl.

In a general way, the compounds of Formula (XIX) and Formula (XX) can be prepared and isolated prior to use.

In some other aspects of the disclosure, the present disclosure provides a method for the synthesis of one or more of the cannabinoid products below:

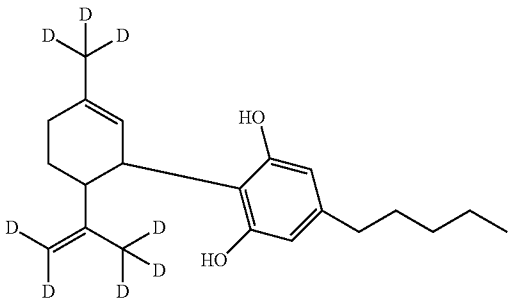
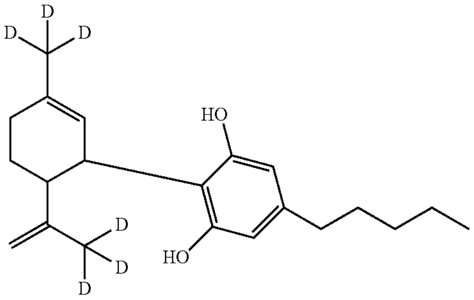
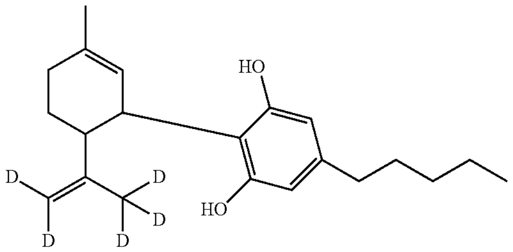
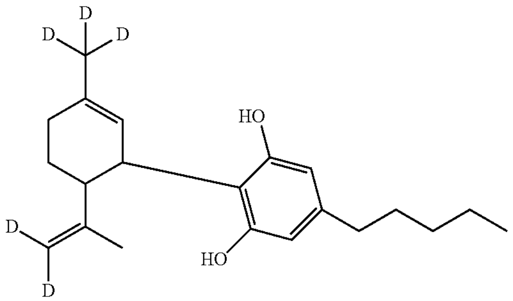
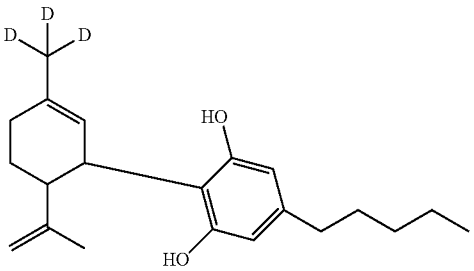
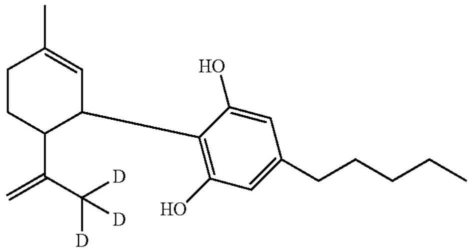
-continued
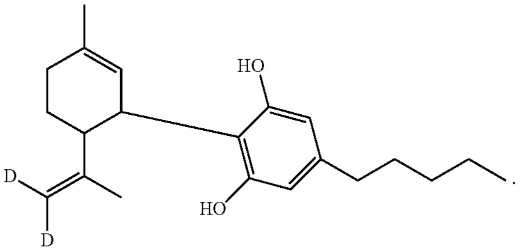
In some other aspects of the disclosure, the present disclosure provides a method for the synthesis of one or more of the cannabinoid products below:
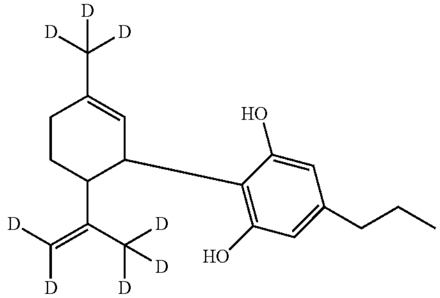
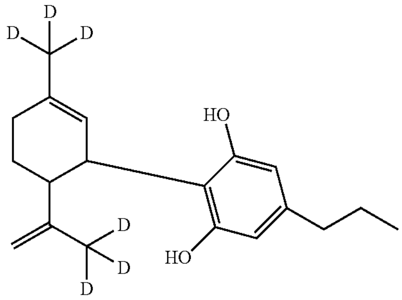
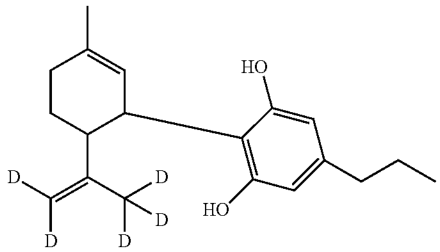
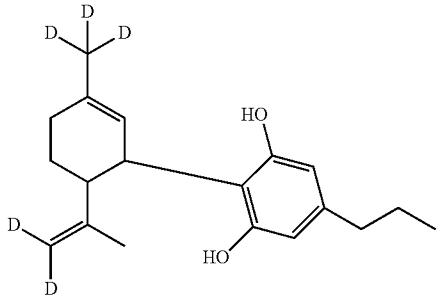

-continued
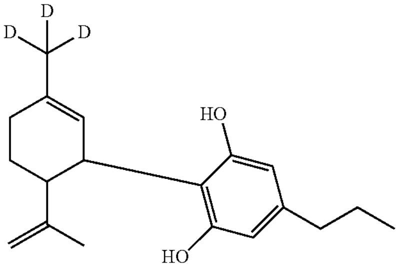
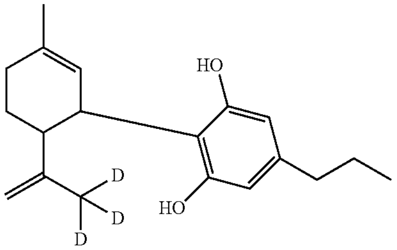
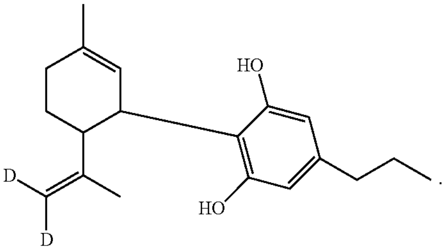
In some other aspects of the disclosure, the present disclosure provides a method for the synthesis of one or more of the cannabinoid products below:
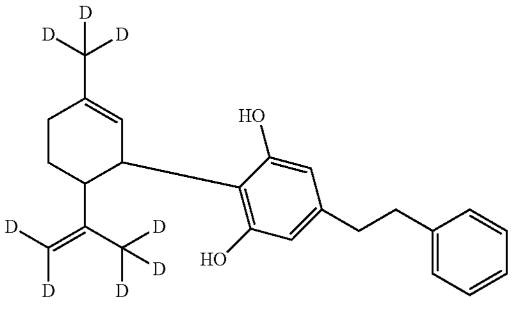
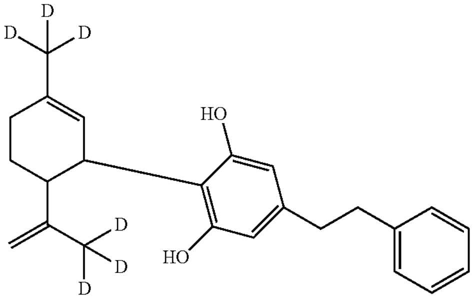
-continued
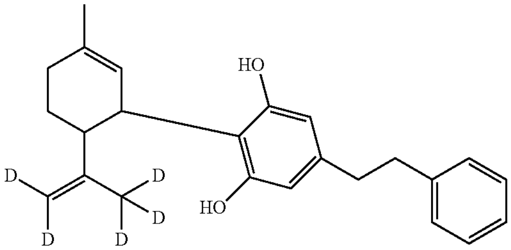
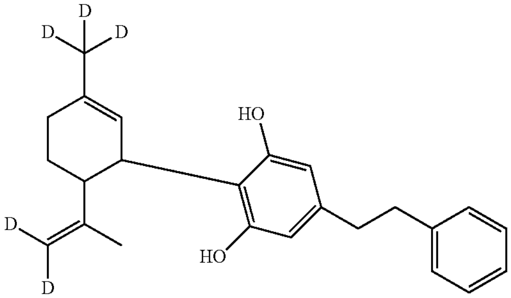
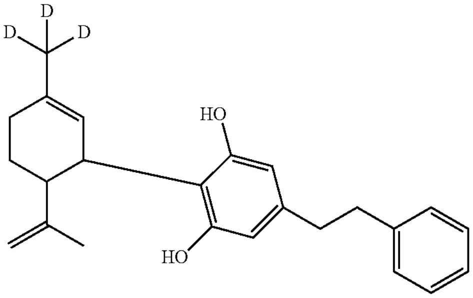
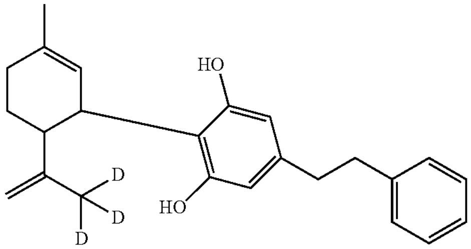
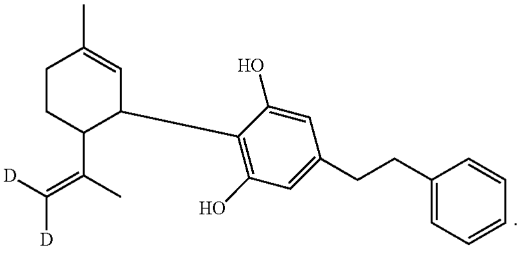
In some other aspects of the disclosure, the present disclosure provides a method for the synthesis of one or more of the cannabinoid products below:

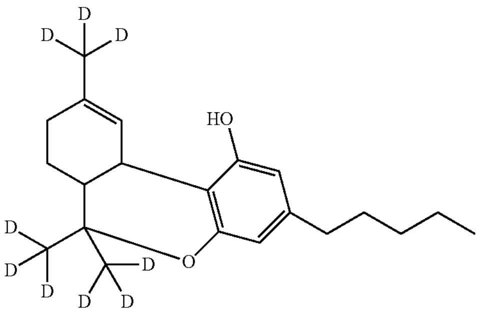
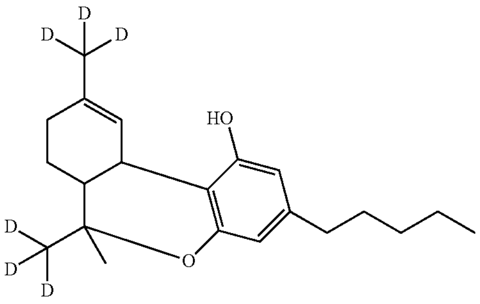
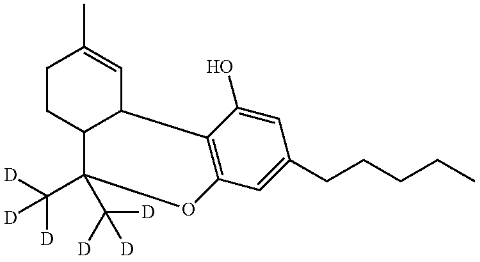
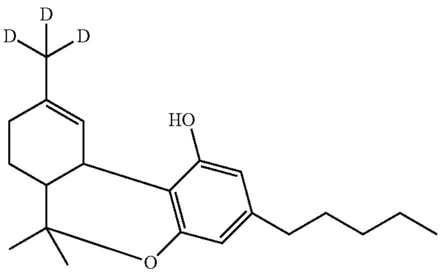
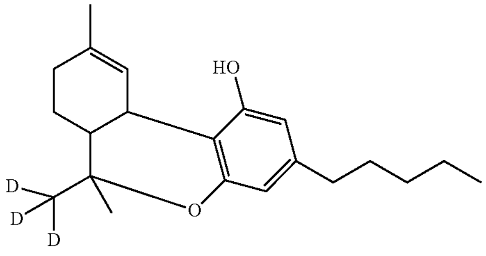
In some other aspects of the disclosure, the present disclosure provides a method for the synthesis of one or more of the cannabinoid products below:
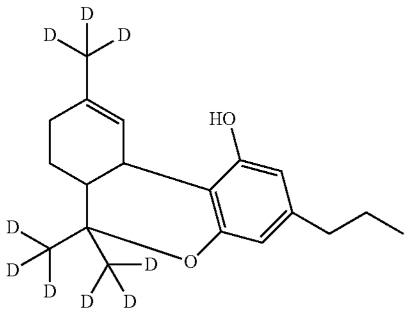
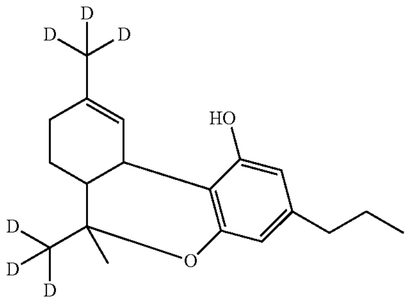
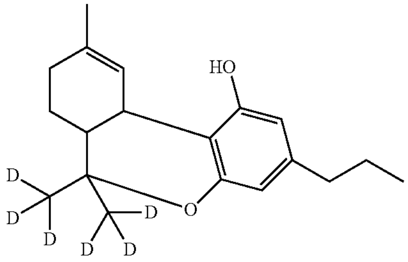
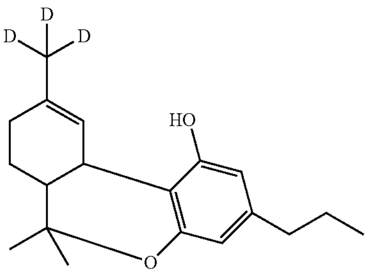
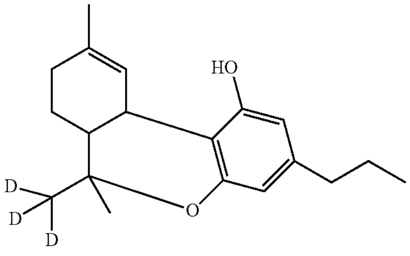
In some other aspects of the disclosure, the present disclosure provides a method for the synthesis of one or more of the cannabinoid products below:

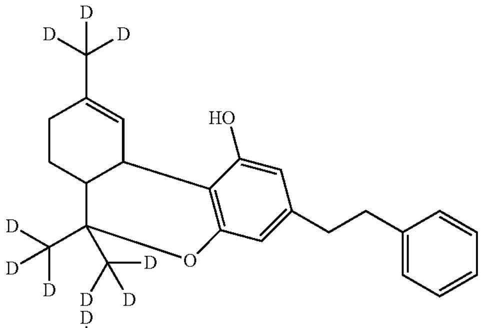

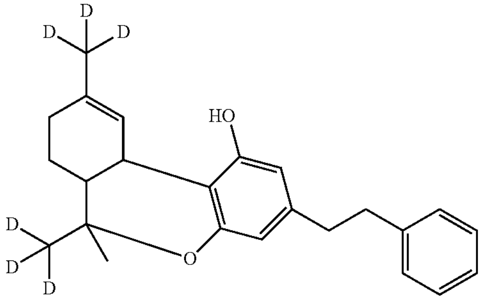

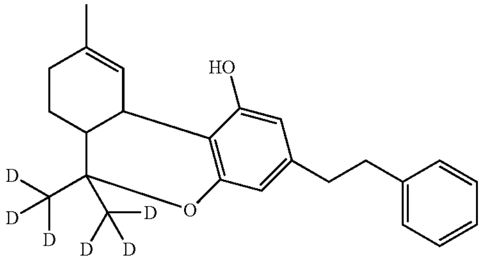

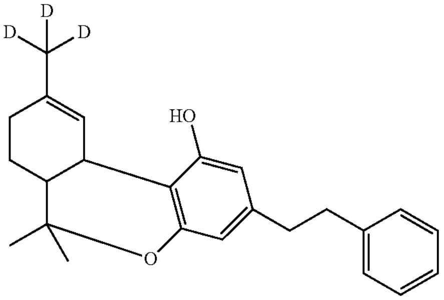

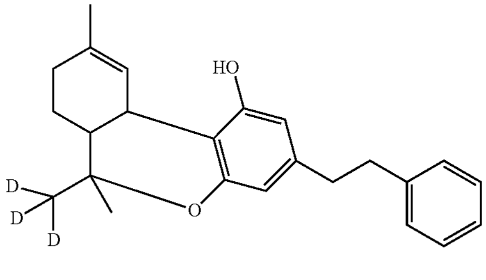

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

The present disclosure is described in the following Examples, which are set forth to aid in the understanding of the disclosure, and should not be construed to limit in any way the scope of the disclosure as defined in the claims which follow thereafter.

EXAMPLES

The disclosure will now be described in further details by way of the following examples, wherein the temperatures are indicated in degrees centigrade and the abbreviations have the usual meaning in the art.

All the procedures described hereafter have been carried out under an inert atmosphere unless stated otherwise. All preparations and manipulations under air-free conditions were carried out under $N_2$ or Ar atmospheres with the use of standard Schlenk, vacuum line and glove box techniques in dry, oxygen-free solvents. Deuterated solvents were degassed and dried over activated molecular sieves. NMR spectra were recorded on a 300 MHz spectrometer (300 MHz for $^{1}H$, 75 MHz for $^{13}C$ and 121.5 MHz for $^{31}P$) or a 400 MHz spectrometer (400 MHz for $^{1}H$, 100 MHz for $^{13}C$ and 162 MHz for $^{31}P$). All $^{31}P$ chemical shifts were measured relative to 85% $H_3PO_4$ as an external reference. $^{1}H$ and $^{13}C$ chemical shifts were measured relative to partially deuterated solvent peaks but are reported relative to tetramethylsilane.

Example 1. Preparation of (E)-4-(4-bromo-2,6-dimethoxyphenyl)but-3-en-2-one

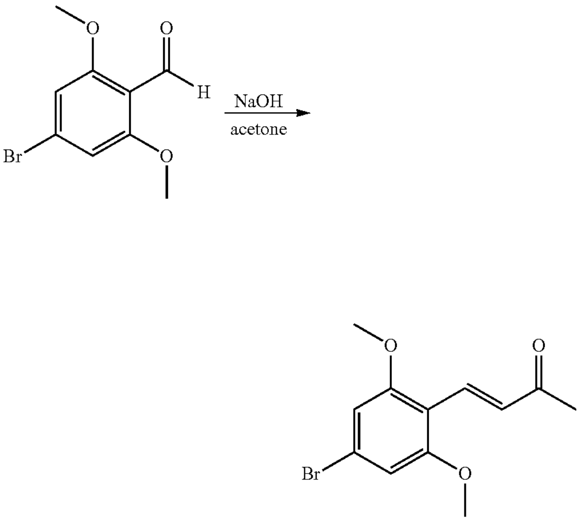

Water (200 ml) and 4-bromo-2,6-dimethoxybenzaldehyde (12.5 g, 51 mmol) was added to a 500 ml Schlenk flask. Acetone (16 g, 276 mmol) and NaOH (8.0 g, 200 mmol) in water (50 ml) were added and the reaction mixture was heated to 60° C. until all the aldehyde was converted (TLC, about 15 hours). The mixture was cooled to room temperature and extracted with diethyl ether (3×100 ml) and the combined organic layer was washed with 0.1 M $H_2SO_4$ (100 ml), brine (100 ml) and dried ($MgSO_4$). The mixture was concentrated to about 50 ml and filtered through a pad of silica gel. It was then evaporated to dryness to give a yellow solid. Yield=13.4 g.

Example 2. Preparation of (S,E)-4-(4-bromo-2,6-dimethoxyphenyl)but-3-en-2-ol

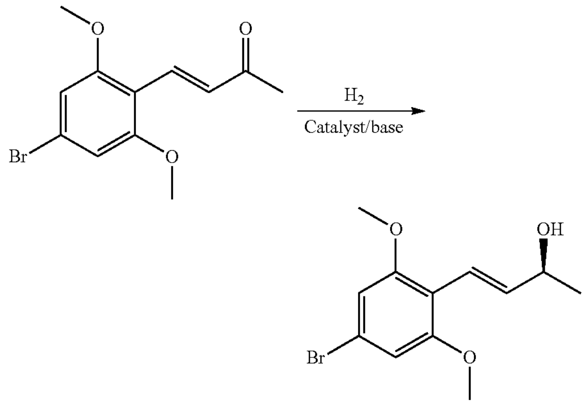

(E)-4-(4-Bromo-2,6-dimethoxyphenyl)but-3-en-2-one (12.1 g, 42.3 mmol) was added to a mixture of $RuCl_2$(R-Xyl-Garphos)(R-Daipen) (25 mg, 0.02 mmol) and $K_2CO_3$ (1.0 g, 7.2 mmol) in a 100 ml Parr pressure reactor. The mixture was degassed with hydrogen and 2-propanol (50 ml) was added with stirring. A solution of KO$^t$Bu (5 mg, 0.045 mmol) in 2-propanol (5 ml) was then added. The pressure was set to 30 atm and the temperature was set to 30° C. and the mixture was stirred for 10 hours. The mixture was cooled to room temperature and the hydrogen vented. The solvent was removed, and the mixture dissolved in diethyl ether and filtered through a pad of silica gel. The solvent was removed under reduced pressure to give the product. Yield=11.9 g (97% e.e., S-isomer).

Example 3. Preparation of 5-methylhex-5-enoic acid

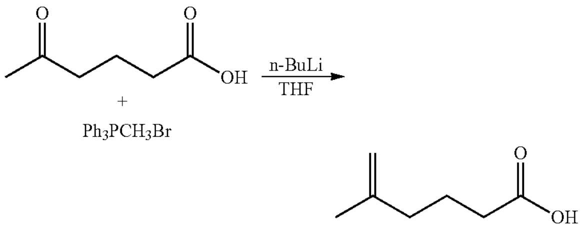

A solution of n-butyllithium (450.0 mL, 720.0 mmol, 1.6 M in hexane) was added to a stirred solution of methyltriphenylphosphonium bromide (257 g, 720.0 mmol) in THF (3000 ml) at 0° C., and the mixture was stirred for 1 hour under argon. A solution of 5-oxohexanoic acid (28.4 mL, 31.2 g, 240.0 mmol) in THF (100 ml) was added, and the mixture was stirred for 24 hours at room temperature. The reaction was quenched with 0.1 M $H_2SO_4$ solution, and the mixture extracted with ethyl acetate. The combined organic layers were washed with brine, dried over $MgSO_4$, and concentrated under vacuum. The resulting residue was purified by column chromatography (hexane-ethyl acetate, 3:1) to afford 5-methylhex-5-enoic acid as a colourless oil. Yield=23.2 g.

Example 4. Preparation of (S,E)-4-(4-bromo-2,6-dimethoxyphenyl)but-3-en-2-yl 5-methylhex-5-enoate

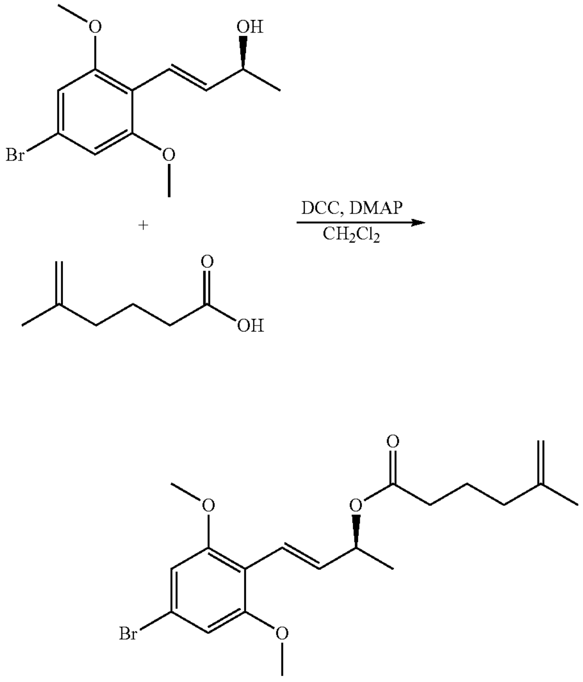

(S,E)-4-(4-Bromo-2,6-dimethoxyphenyl)but-3-en-2-ol (12.06 g, 42.0 mmol) was added to a 500 ml Schlenk along with $CH_2Cl_2$ (250 ml) and the mixture cooled to 0° C. with stirring. DCC (10.4 g, 50 mmol) and DMAP (0.50 g, 4.1 mmol) were added along with 5-methylhex-5-enoic acid (5.38 g, 42.0 mmol). The mixture was stirred at 0° C. for 2 hours then warmed to room temperature and stirred overnight. On completion of the reaction (TLC) the mixture was filtered and the filtrate was washed with 0.5 M $H_2SO_4$ (200 ml), followed by saturated $NaHCO_3$ solution (200 ml) and brine. The mixture was dried ($MgSO_4$), then filtered and concentrated under vacuum. The crude material was purified by column chromatography using hexanes/ethyl acetate (10:1) to give the product as a colourless oil. Yield=14.76 g.

Example 5. Preparation of (2R,3R,E)-3-(4-bromo-2,6-dimethoxyphenyl)-2-(3-methylbut-3-enyl)hex-4-enoic acid

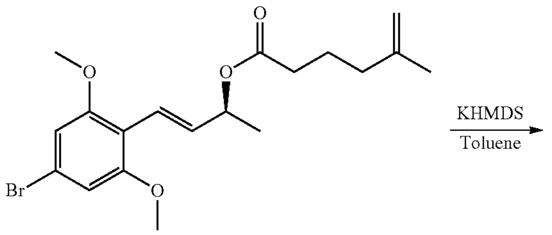

-continued

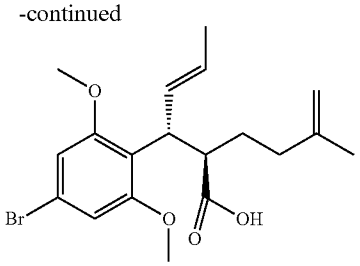

KHMDS (150 mL of a 0.5 M in Toluene, 75.3 mmol) was added to a 1000 ml reaction flask under argon, followed by anhydrous toluene (150 ml) at −78° C. A solution of (S,E)-4-(4-bromo-2,6-dimethoxyphenyl)but-3-en-2-yl 5-methylhex-5-enoate (11.4 g, 28.7 mmol) in anhydrous toluene (150 mL) was added over 30 minutes and the mixture stirred for 1 hour at −78° C. This was followed by a solution of anhydrous pyridine (8.78 g, 111 mmol) and TMSCl (13.0 g, 120 mmol) in anhydrous toluene (100 ml) over 10 minutes and the mixture stirred at −78° C. for 30 min before warming to room temperature and stirred for an additional 6 hours. The reaction was quenched with saturated $NH_4Cl$ solution (250 ml) followed by 0.5 M $H_2SO_4$ (200 ml) and stirred for another 1 hour. The layers were separated and extracted with ethyl acetate (3×200 ml). The combined organic layers were washed with brine (250 ml), dried over $MgSO_4$, filtered and concentrated to give an oily solid. The crude product was purified by silica gel chromatography using hexanes/ethyl acetate (5:1) to give the product as a white solid. Yield=9.71 g.

Example 6. Preparation of (2R,3R,E)-methyl 3-(4-bromo-2,6-dimethoxyphenyl)-2-(3-methylbut-3-enyl)hex-4-enoate

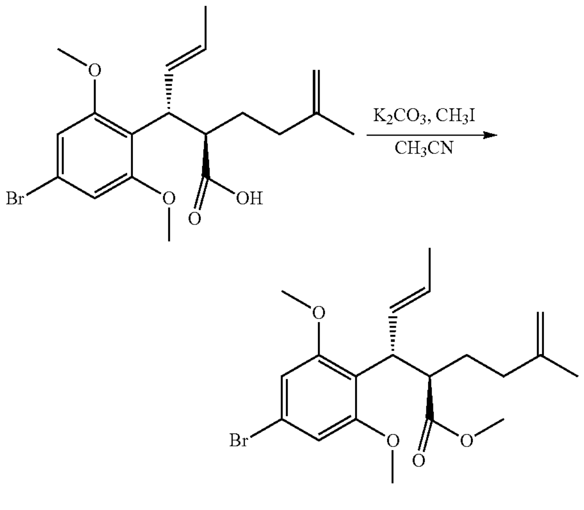

Acetonitrile (50 ml) was added to a mixture of (2R,3R,E)-3-(4-bromo-2,6-dimethoxyphenyl)-2-(3-methylbut-3-enyl)hex-4-enoic acid (4.57 g, 11.5 mmol) and $K_2CO_3$ (4.76 g, 34.5 mmol) with stirring at room temperature. Methyl iodide (4.90 g, 34.5 mmol) was added dropwise. The mixture was stirred for 1 hour at room temperature, then heated to 60° C. and stirred overnight. On completion of the reaction (TLC) it was quenched with saturated $NH_4Cl$ solution (50 ml) and ethyl acetate (50 ml) added. The phases were separated, and the aqueous layer was extracted with ethyl acetate (3×50 ml), washed with brine (50 ml), dried ($MgSO_4$), filtered and the solvent removed under reduced pressure. The residue was purified by chromatography using hexanes/ethyl acetate to give the product as a pale-yellow oil. Yield=4.37 g.

Example 7. Preparation of (1R,2R)-methyl 2-(4-bromo-2,6-dimethoxyphenyl)-4-methylcyclohex-3-enecarboxylate

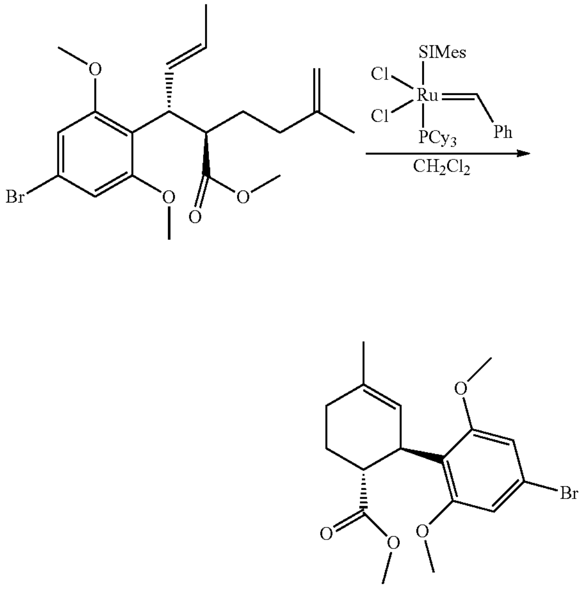

$RuCl_2(SIMes)(PCy_3)$(benzylidene) (156 mg, 0.19 mmol) was added to a solution of (2R,3R,E)-methyl 3-(4-bromo-2,6-dimethoxy-phenyl)-2-(3-methylbut-3-enyl)-hex-4-enoate (3.97 g, 9.66 mmol) in $CH_2Cl_2$ (100 ml) in a Schlenk flask under argon. The reaction mixture was stirred vigorously for 12 hours at 40° C. The solvent was removed under vacuum and the crude oil was purified by chromatography using hexanes/ethyl acetate to give the product as a pale-yellow oil. Yield=3.28 g.

Example 8. Preparation of (1R,2R)-methyl 2-(2,6-dimethoxy-4-pentylphenyl)-4-methylcyclohex-3-enecarboxylate

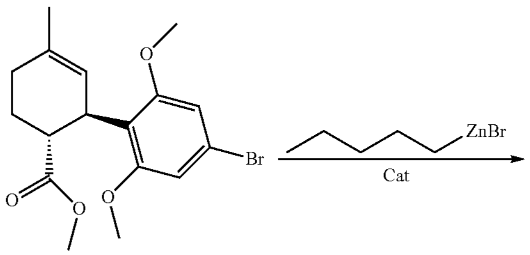

-continued

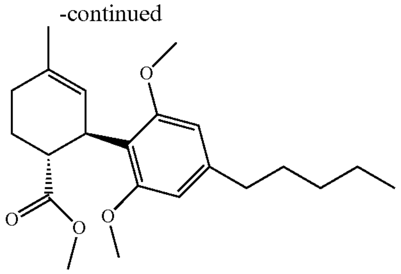

A solution of n-pentylzinc bromide (8.15 ml of a 0.5 M solution in THF, 4.07 mmol) was added to a mixture of (1R,2R)-methyl 2-(4-bromo-2,6-dimethoxy-phenyl)-4-methylcyclohex-3-enecarboxylate (1.0 g, 2.72 mmol) and $PdCl_2$(dppf) (50 mg, 0.047 mmol, 2.5%) and the mixture stirred at 60° C. for 2 hours under argon. It was quenched with ammonium chloride solution and diethyl ether added. The phases were separated, and the organic layer was dried ($MgSO_4$), filtered and evaporated to dryness. The NMR spectrum of the residue shows 100% conversion of the substrate to the product. Yield=0.94 g.

Example 9. Preparation of (6aR)-6,6,9-trimethyl-3-pentyl-6a,7,8,10a-tetrahydro-6H-benzo-[c]chromen-1-ol

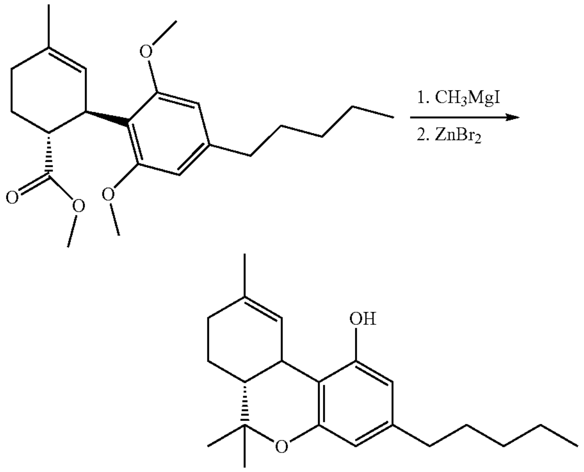

(1R,2R)-methyl 2-(2,6-dimethoxy-4-pentylphenyl)-4-methylcyclohex-3-enecarboxylate (200 mg, 0.55 mmol) was added to a Schlenk flask under argon at 0° C. A solution of methylmagnesium iodide (2.0 ml of a 3.0 M solution in $Et_2O$, 6.0 mmol) was added slowly at 0° C. and the mixture allowed to warm to room temperature and stirred for 30 minutes. The solvent was slowly removed under reduced pressure, then the resultant viscous mixture heated to 160° C. for 2.5 h under vacuum. It was cooled to room temperature and diethyl ether (25 ml) added. Saturated $NH_4Cl$ (25 ml) was used to quench the reaction mixture and the phases separated. The aqueous layer was extracted with diethyl ether (3×25 ml), washed with brine, and the combined organic layers dried ($MgSO_4$), then filtered and concentrated to give the crude intermediate as a pale-yellow oil. This was dissolved in $CH_2Cl_2$ (25 ml) and transferred to a Schlenk flask containing $MgSO_4$ (300 mg, 2.5 mmol) and $ZnBr_2$ (200 mg, 0.89 mmol) and stirred at 35° C. for 12 hours under argon. The reaction mixture was quenched with saturated $NH_4Cl$ solution (25 ml) and the phases separated. The aqueous layer was extracted with $CH_2Cl_2$ (3×25 ml) and the combined organic layers were dried over $MgSO_4$, filtered and evaporated under vacuum. The residue was purified by chromatography using hexanes/ethyl acetate (20:1) to give the product as a pale-yellow oil. Yield=152 mg.

Example 10. Preparation of (1R,2R)-methyl 2-(2,6-dimethoxy-4-propyl-phenyl)-4-methylcyclohex-3-enecarboxylate

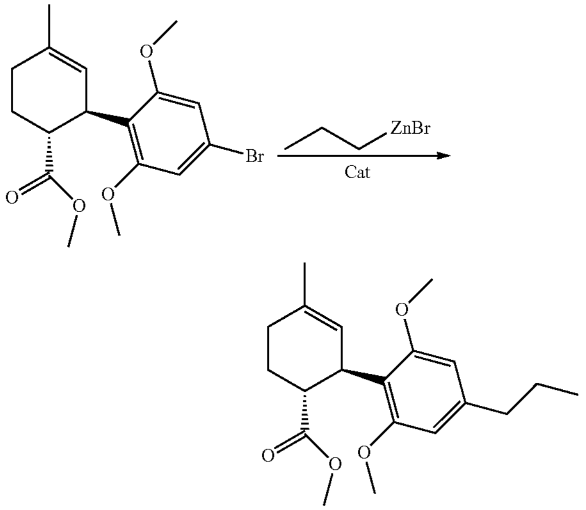

A solution of n-propylzinc bromide (8.15 ml of a 0.5 M solution in THF, 4.07 mmol) was added to a mixture of (1R,2R)-methyl 2-(4-bromo-2,6-dimethoxy-phenyl)-4-methylcyclohex-3-enecarboxylate (1.0 g, 2.72 mmol) and $PdCl_2$(dppf) (50 mg, 0.047 mmol, 2.5%) and the mixture stirred at 40° C. overnight under argon. It was quenched with ammonium chloride solution and hexanes added. The phases were separated, and the organic layer was dried ($MgSO_4$), filtered and evaporated to dryness. The NMR spectrum of the residue shows 100% conversion of the substrate to the product. Yield=0.82 g.

Example 11. Preparation of (6aR)-6,6,9-trimethyl-3-propyl-6a,7,8,10a-tetrahydro-6H-benzo-[c]chromen-1-ol

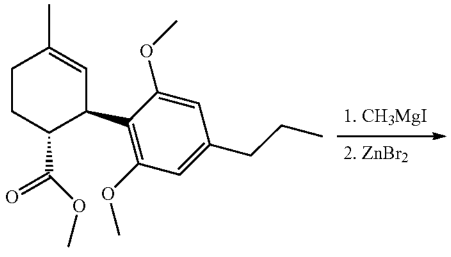

-continued

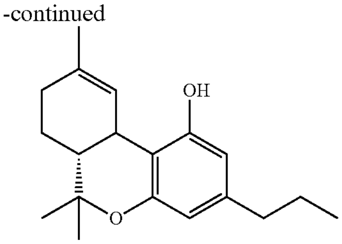

(1R,2R)-methyl 2-(2,6-dimethoxy-4-propylphenyl)-4-methylcyclohex-3-enecarboxylate (183 mg, 0.55 mmol) was added to a Schlenk flask under argon at 0° C. A solution of methylmagnesium iodide (2.0 ml of a 3.0 M solution in $Et_2O$, 6.0 mmol) was added slowly at 0° C. and the mixture allowed to warm to room temperature and stirred for 30 minutes. The solvent was slowly removed under reduced pressure, then the resultant viscous mixture heated to 160° C. for 2.5 h under vacuum. It was cooled to room temperature and diethyl ether (25 ml) added. Saturated $NH_4Cl$ (25 ml) was used to quench the reaction mixture and the phases separated. The aqueous layer was extracted with diethyl ether (3×25 ml), washed with brine, and the combined organic layers dried ($MgSO_4$), then filtered and concentrated to give the crude intermediate as a pale-yellow oil. This was dissolved in $CH_2Cl_2$ (25 ml) and transferred to a Schlenk flask containing $MgSO_4$ (300 mg, 2.5 mmol) and $ZnBr_2$ (200 mg, 0.89 mmol) and stirred at 35° C. for 12 hours under argon. The reaction mixture was quenched with saturated $NH_4Cl$ solution (25 ml) and the phases separated. The aqueous layer was extracted with $CH_2Cl_2$ (3×25 ml) and the combined organic layers were dried over $MgSO_4$, filtered and evaporated under vacuum. The residue was purified by chromatography using hexanes/ethyl acetate (20:1) to give the product as a pale-yellow oil. Yield=138 mg.

Example 12. Preparation of (6aR)-9-methyl-6,6-bis(methyl-$d_3$)-3-pentyl-6a,7,8,10a-tetrahydro-6H-benzo[c]chromen-1-ol

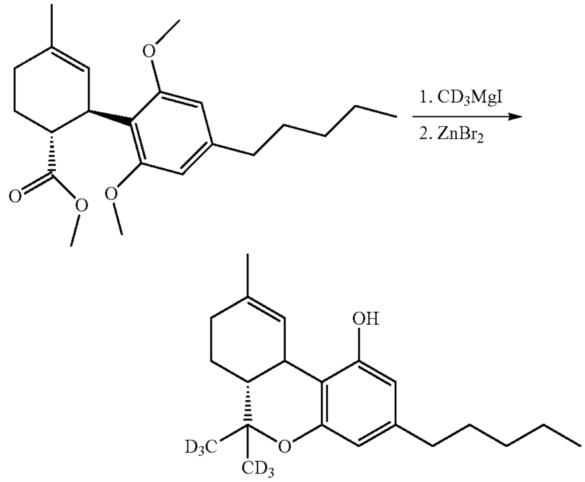

(1R,2R)-methyl 2-(2,6-dimethoxy-4-pentylphenyl)-4-methylcyclohex-3-enecarboxylate (200 mg, 0.55 mmol) was added to a Schlenk flask under argon at 0° C. A solution of $CD_3MgI$ (2.0 ml of a 3.0 M solution in $Et_2O$, 6.0 mmol) was added slowly at 0° C. and the mixture allowed to warm to room temperature and stirred for 30 minutes. The solvent was slowly removed under reduced pressure, then the resultant viscous mixture heated to 160° C. for 2.5 h under vacuum. It was cooled to room temperature and diethyl ether (25 ml) added. Saturated $NH_4Cl$ (25 ml) was used to quench the reaction mixture and the phases separated. The aqueous layer was extracted with diethyl ether (3×25 ml), washed with brine, and the combined organic layers dried ($MgSO_4$), then filtered and concentrated to give the crude intermediate as a pale-yellow oil. This was dissolved in $CH_2Cl_2$ (25 ml) and transferred to a Schlenk flask containing $MgSO_4$ (300 mg, 2.5 mmol) and $ZnBr_2$ (200 mg, 0.89 mmol) and stirred at 35° C. for 12 hours under argon. The reaction mixture was quenched with saturated $NH_4Cl$ solution (25 ml) and the phases separated. The aqueous layer was extracted with $CH_2Cl_2$ (3×25 ml) and the combined organic layers were dried over $MgSO_4$, filtered and evaporated under vacuum. The residue was purified by chromatography using hexanes/ethyl acetate (20:1) to give the product as a pale-yellow oil. Yield=148 mg.

Example 13. Preparation of (6aR)-9-methyl-6,6-bis(methyl-$d_3$)-3-propyl-6a,7,8,10a-tetrahydro-6H-benzo[c]chromen-1-ol

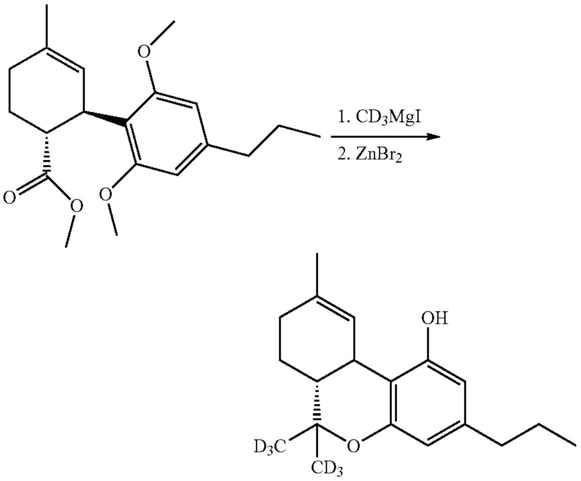

(1R,2R)-methyl 2-(2,6-dimethoxy-4-propylphenyl)-4-methylcyclohex-3-enecarboxylate (183 mg, 0.55 mmol) was added to a Schlenk flask under argon at 0° C. A solution of $CD_3MgI$ (2.0 ml of a 3.0 M solution in $Et_2O$, 6.0 mmol) was added slowly at 0° C. and the mixture allowed to warm to room temperature and stirred for 30 minutes. The solvent was slowly removed under reduced pressure, then the resultant viscous mixture heated to 160° C. for 2.5 h under vacuum. It was cooled to room temperature and diethyl ether (25 ml) added. Saturated $NH_4Cl$ (25 ml) was used to quench the reaction mixture and the phases separated. The aqueous layer was extracted with diethyl ether (3×25 ml), washed with brine, and the combined organic layers dried ($MgSO_4$), then filtered and concentrated to give the crude intermediate as a pale-yellow oil. This was dissolved in $CH_2Cl_2$ (25 ml) and transferred to a Schlenk flask containing $MgSO_4$ (300 mg, 2.5 mmol) and $ZnBr_2$ (200 mg, 0.89 mmol) and stirred at 35° C. for 12 hours under argon. The reaction mixture was quenched with saturated $NH_4Cl$ solution (25 ml) and the phases separated. The aqueous layer was extracted with $CH_2Cl_2$ (3×25 ml) and the combined organic layers were dried over $MgSO_4$, filtered and evaporated under vacuum. The residue was purified by chromatography using hexanes/ethyl acetate (20:1) to give the product as a pale-yellow oil. Yield=132 mg.

Example 14. Preparation of (1R,2R)-2-(2,6-dimethoxy-4-pentylphenyl)-N-methoxy-N,4-dimethylcyclohex-3-enecarboxamide

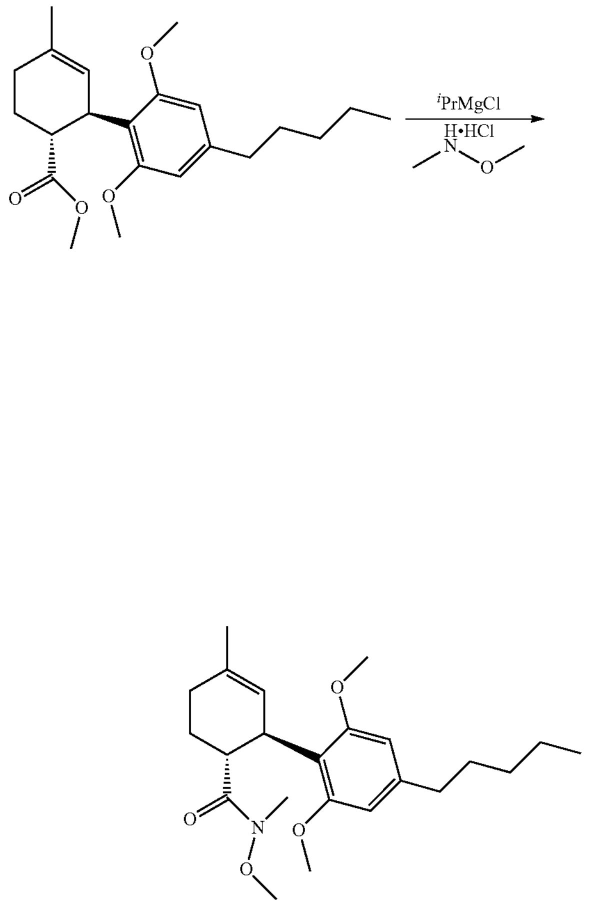

Figure 2:
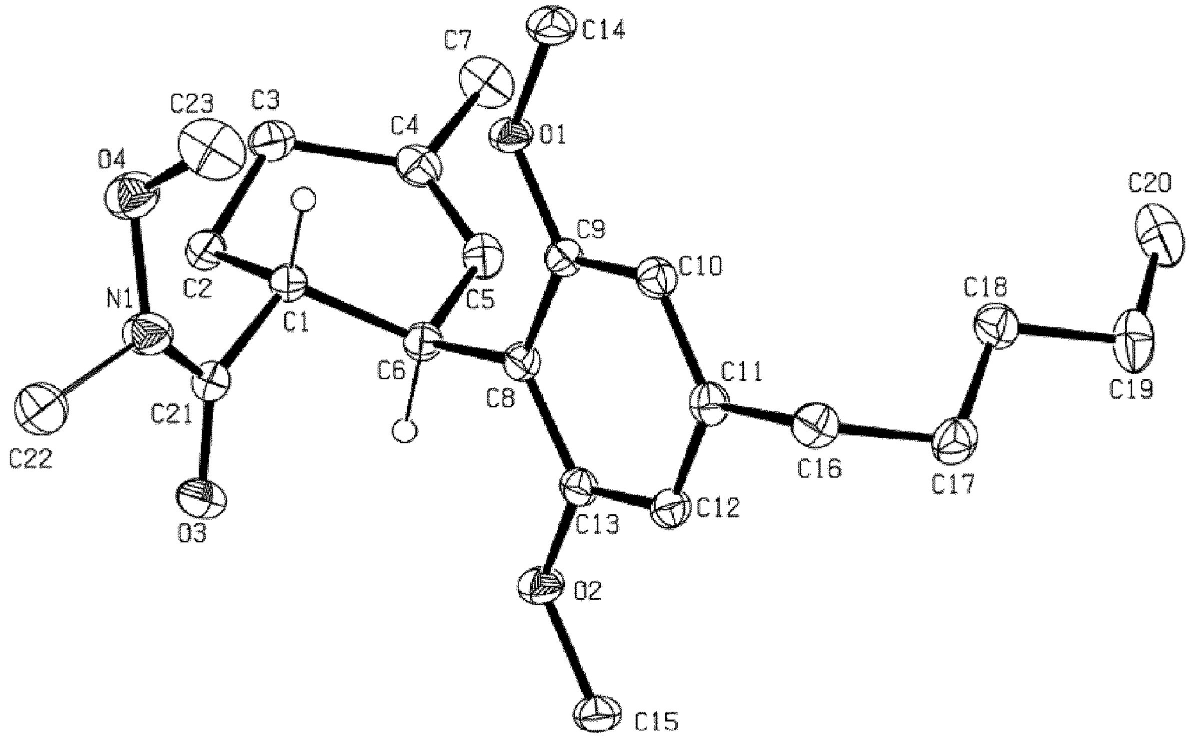
FIG. 2 shows the X-ray structure of (1R,2R)-2-(2,6-dimethoxy-4-pentylphenyl)-N-methoxy-N,4-dimethylcyclohex-3-enecarboxamide.

THF (10 ml) was added to a mixture of (1R,2R)-methyl 2-(2,6-dimethoxy-4-pentylphenyl)-4-methylcyclohex-3-en-ecarb-oxylate (500 mg, 1.39 mmol) and N,O-dimethylhydroxylamine hydrochloride (210 mg, 2.15 mmol) and the mixture was cooled to −20° C. under argon. A solution of isopropylmagnesium chloride (0.83 ml of a 2.0 M solution in THF, 1.66 mmol) was added slowly and the mixture stirred for 2 hours at −20° C., then warmed to room temperature. After completion of the reaction (TLC), the mixture was quenched with ammonium chloride solution. Diethyl ether (10 ml) was added and the phases separated. The aqueous layer was extracted with diethyl ether (3×10 ml) and the combined organic phase was dried ($MgSO_4$) and filtered. The solvent was removed under reduced pressure to give the product as a pale-yellow liquid that crystallizes on standing. Yield=530 mg. The x-ray crystal structure of this compound is shown in FIG. 2.

Example 15. Preparation of 1-((1R,2R)-2',6'-dimethoxy-5-methyl-4'-pentyl-1,2,3,4-tetrahydro-[1,1'-biphenyl]-2-yl)ethan-1-one-2,2,2-$d_3$

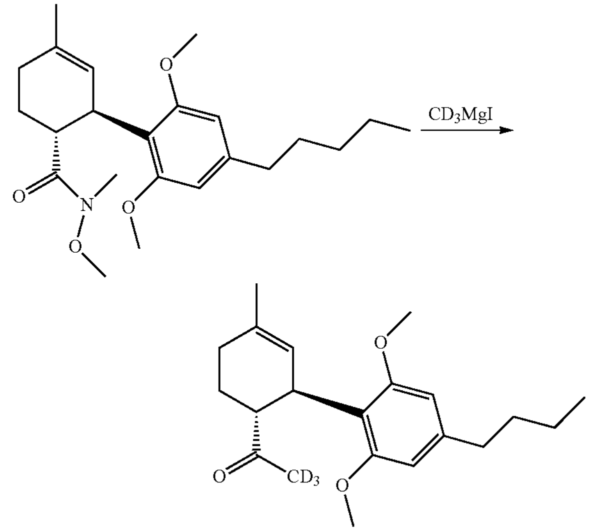

A solution of (1R,2R)-2-(2,6-dimethoxy-4-pentylphenyl)-N-methoxy-N,4-dimethylcyclohex-3-enecarboxamide (200 mg, 0.51 mmol) in THF (5 ml) was cooled to −5° C. under argon. A solution of $CD_3MgI$ (0.54 ml of a 1.0 M solution in THF, 0.54 mmol) was added slowly and the mixture stirred for 2 hours at −5° C., then warmed to room temperature and stirred overnight. The mixture was quenched with ammonium chloride solution and diethyl ether (100 ml) was added and the phases separated. The aqueous layer was extracted with diethyl ether (3×10 ml) and the combined organic phase was dried ($MgSO_4$) and filtered. The solvent was removed under reduced pressure to give the product as a pale-yellow liquid. Yield=162 mg.

Example 16 Preparation of (1R,2R)-2',6'-dimethoxy-5-methyl-4'-pentyl-2-(prop-1-en-2-yl-$d_5$)-1,2,3,4-tetrahydro-1,1'-biphenyl

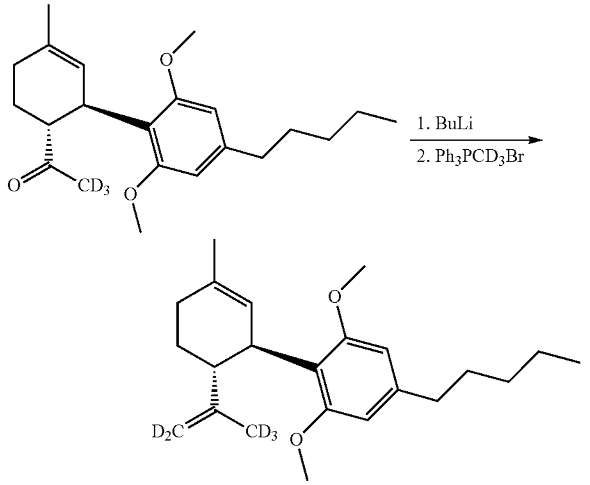

A solution of $d_3$-methyltriphenylphosphonium bromide (218 mg, 0.60 mmol) in THF (10 ml) was cooled to 0° C. under argon. A solution of butyllithium (0.38 ml of a 1.6 M solution in hexanes, 0.60 mmol) was added slowly and the mixture stirred for 2 hours at 0° C. A solution of 1-((1R, 2R)-2',6'-dimethoxy-5-methyl-4'-pentyl-1,2,3,4-tetrahydro-[1,1'-biphenyl]-2-yl)ethan-1-one-2,2,2-$d_3$ (140 mg, 0.40 mmol) in THF (5 ml) was added and the mixture stirred for 1 hour at 0° C., then warmed to room temperature and stirred overnight. The mixture was quenched with ammonium chloride solution and diethyl ether (10 ml) was added and the phases separated. The aqueous layer was extracted with diethyl ether (3×10 ml) and the combined organic phase was dried ($MgSO_4$) and filtered. The solvent was removed under reduced pressure to give the product as a pale-yellow liquid. Yield=118 mg.

Example 17. Preparation of (1'R,2'R)-5'-methyl-4-pentyl-2'-(prop-1-en-2-yl-$d_5$)-1',2',3',4'-tetrahydro-[1,1'-biphenyl]-2,6-diol

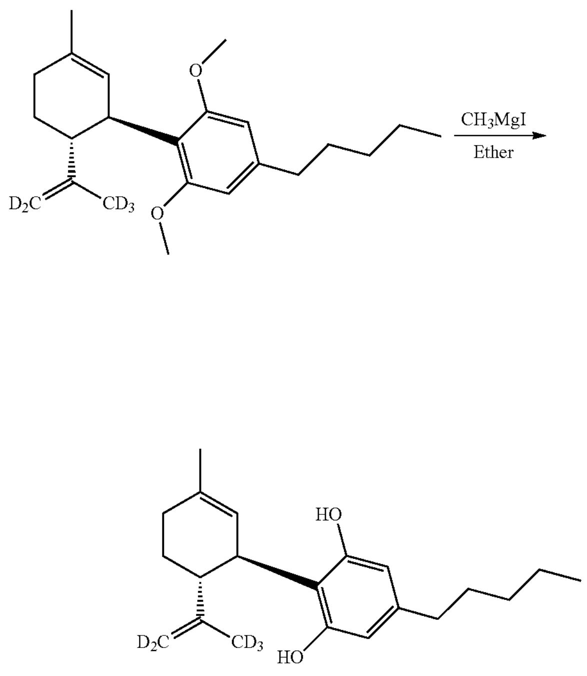

(1R,2R)-2',6'-dimethoxy-5-methyl-4'-pentyl-2-(prop-1-en-2-yl-$d_5$)-1,2,3,4-tetrahydro-1,1'-biphenyl (100 mg, 0.29 mmol) was added to a Schlenk flask under argon at 0° C. A solution of $CH_3MgI$ (2.0 ml of a 3.0 M solution in $Et_2O$, 6.0 mmol) was added slowly at 0° C. and the mixture allowed to warm to room temperature and stirred for 30 minutes. The solvent was slowly removed under reduced pressure, then the resultant viscous mixture heated to 160° C. for 3 hours under vacuum. It was cooled to room temperature and diethyl ether (10 ml) added. Saturated $NH_4Cl$ (10 ml) was used to quench the reaction mixture and the phases separated. The aqueous layer was extracted with diethyl ether (3×10 ml), washed with brine, and the combined organic layers dried ($MgSO_4$), then filtered and concentrated to give the crude intermediate as a pale-yellow oil. Yield=84 mg.

Example 18. Preparation of (1R,2R)-2-(2,6-dimethoxy-4-propylphenyl)-N-methoxy-N,4-dimethylcyclohex-3-enecarboxamide

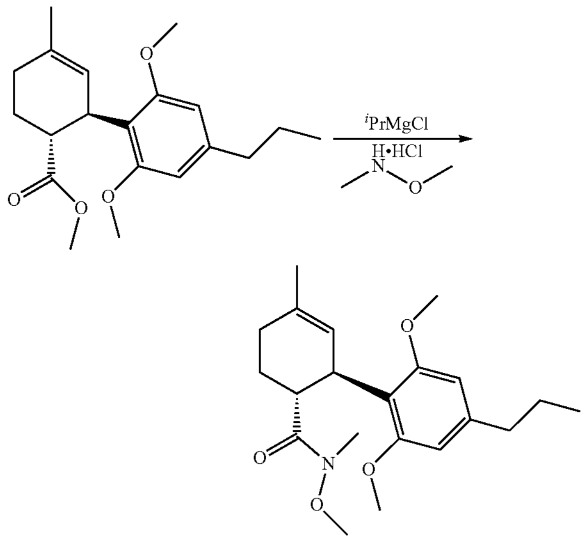

THF (10 ml) was added to a mixture of (1R,2R)-methyl 2-(2,6-dimethoxy-4-propylphenyl)-4-methylcyclohex-3-en-ecarb-oxylate (462 mg, 1.39 mmol) and N,O-dimethylhydroxylamine hydrochloride (210 mg, 2.15 mmol) and the mixture was cooled to −20° C. under argon. A solution of isopropylmagnesium chloride (0.83 ml of a 2.0 M solution in THF, 1.66 mmol) was added slowly and the mixture stirred for 2 hours at −20° C., then warmed to room temperature. After completion of the reaction (TLC), the mixture was quenched with ammonium chloride solution. Diethyl ether (10 ml) was added and the phases separated. The aqueous layer was extracted with diethyl ether (3×10 ml) and the combined organic phase was dried ($MgSO_4$) and filtered. The solvent was removed under reduced pressure to give the product as a pale-yellow liquid that crystallizes on standing. Yield=470 mg.

Example 19. Preparation of 1-((1R,2R)-2',6'-dimethoxy-5-methyl-4'-propyl-1,2,3,4-tetrahydro-[1,1'-biphenyl]-2-yl)ethan-1-one-2,2,2-$d_3$

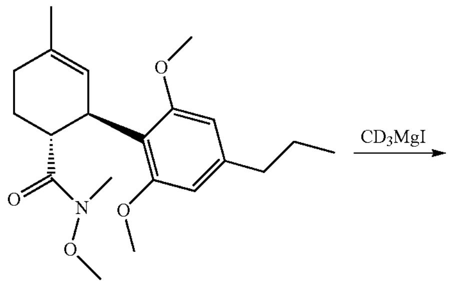

-continued

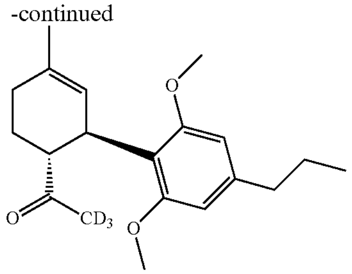

A solution of (1R,2R)-2-(2,6-dimethoxy-4-propylphenyl)-N-methoxy-N,4-dimethylcyclohex-3-enecarboxamide (200 mg, 0.55 mmol) in THF (5 ml) was cooled to −5° C. under argon. A solution of $CD_3MgI$ (0.59 ml of a 1.0 M solution in THF, 0.59 mmol) was added slowly and the mixture stirred for 2 hours at −5° C., then warmed to room temperature and stirred overnight. The mixture was quenched with ammonium chloride solution and diethyl ether (100 ml) was added and the phases separated. The aqueous layer was extracted with diethyl ether (3×10 ml) and the combined organic phase was dried ($MgSO_4$) and filtered. The solvent was removed under reduced pressure to give the product as a pale-yellow liquid. Yield=177 mg.

Example 20. Preparation of (1R,2R)-2',6'-dimethoxy-5-methyl-2-(prop-1-en-2-yl-$d_5$)-4'-propyl-1,2,3,4-tetrahydro-1,1'-biphenyl

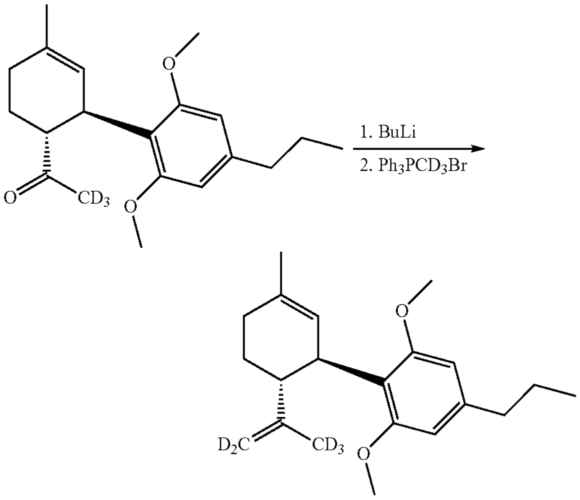

A solution of $d_3$-methyltriphenylphosphonium bromide (271 mg, 0.75 mmol) in THF (10 ml) was cooled to 0° C. under argon. A solution of butyllithium (0.47 ml of a 1.6 M solution in hexanes, 0.75 mmol) was added slowly and the mixture stirred for 2 hours at 0° C. A solution of 1-((1R,2R)-2',6'-dimethoxy-5-methyl-4'-propyl-1,2,3,4-tetrahydro-[1,1'-biphenyl]-2-yl)ethan-1-one-2,2,2-$d_3$ (160 mg, 0.50 mmol) in THF (5 ml) was added and the mixture stirred for 1 hour at 0° C., then warmed to room temperature and stirred overnight. The mixture was quenched with ammonium chloride solution and diethyl ether (10 ml) was added and the phases separated. The aqueous layer was extracted with diethyl ether (3×10 ml) and the combined organic phase was dried ($MgSO_4$) and filtered. The solvent was removed under reduced pressure to give the product as a pale-yellow liquid. Yield=130 mg.

Example 21. Preparation of (1'R,2'R)-5'-methyl-2'-(prop-1-en-2-yl-$d_5$)-4-propyl-1',2',3',4'-tetrahydro-[1,1'-biphenyl]-2,6-diol

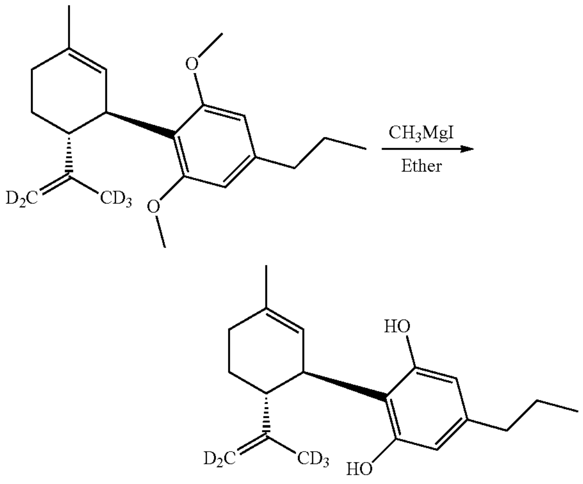

(1R,2R)-2',6'-dimethoxy-5-methyl-2-(prop-1-en-2-yl-$d_5$)-4'-propyl-1,2,3,4-tetrahydro-1,1'-biphenyl (100 mg, 0.31 mmol) was added to a Schlenk flask under argon at 0° C. A solution of $CH_3MgI$ (2.0 ml of a 3.0 M solution in $Et_2O$, 6.0 mmol) was added slowly at 0° C. and the mixture allowed to warm to room temperature and stirred for 30 minutes. The solvent was slowly removed under reduced pressure, then the resultant viscous mixture heated to 160° C. for 3 hours under vacuum. It was cooled to room temperature and diethyl ether (10 ml) added. Saturated $NH_4Cl$ (10 ml) was used to quench the reaction mixture and the phases separated. The aqueous layer was extracted with diethyl ether (3×10 ml), washed with brine, and the combined organic layers dried ($MgSO_4$), then filtered and concentrated to give the crude intermediate as a pale-yellow oil. Yield=86 mg.

Example 22. Preparation of (1R,2R)-methyl 2-(2,6-dimethoxy-4-phenethylphenyl)-4-methylcyclohex-3-enecarboxylate

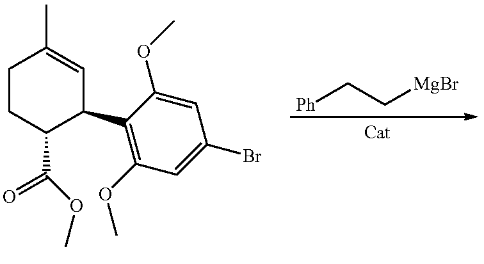

-continued

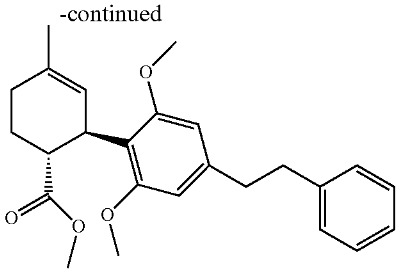

A solution of phenethylmagnesium bromide (2.72 ml of a 0.6 M solution in THF, 1.63 mmol) was added to a mixture of $ZnBr_2$ (0.363 g, 1.63 mmol) and LiBr (0.142 g, 1.63 mmol) and the mixture stirred for 30 minutes at room temperature. A solution of (1R,2R)-methyl 2-(4-bromo-2,6-dimethoxyphenyl)-4-methylcyclohex-3-enecarboxylate (0.4 g, 1.09 mmol) in THF (6 ml) was added to the mixture and $PdCl_2$(dppf) (20 mg, 0.027 mmol) and the mixture stirred at 40° C. overnight under argon. It was cooled to room temperature and quenched with ammonium chloride solution and hexanes added. The phases were separated, and the organic layer was dried ($MgSO_4$), filtered and evaporated to dryness. The residue was filtered through a short silica gel pad, eluting with ethyl acetate/hexanes (1/6). The product was isolated as a yellow oil. Yield=0.50 g.

Example 23. Preparation of (1R,2R)-2-(2,6-dimethoxy-4-phenethylphenyl)-N-methoxy-N,4-dimethylcyclohex-3-enecarboxamide

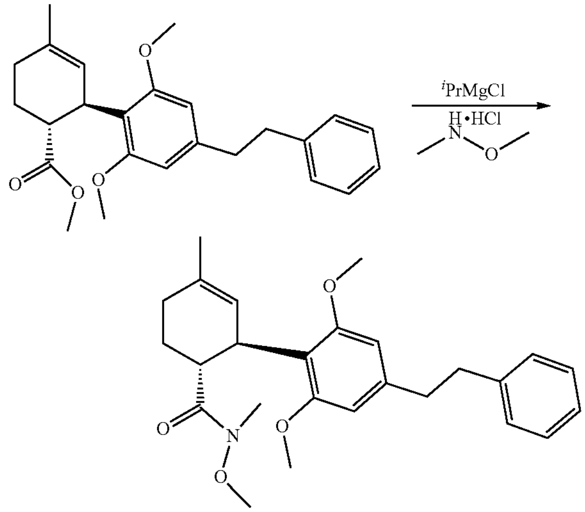

THF (5 ml) was added to a mixture of (1R,2R)-methyl 2-(2,6-dimethoxy-4-phenethylphenyl)-4-methylcyclohex-3-enecarboxylate (420 mg, 1.06 mmol) and N,O-dimethylhydroxylamine hydrochloride (161 mg, 1.65 mmol) and the mixture was cooled to −20° C. under argon. A solution of isopropylmagnesium chloride (1.60 ml of a 2.0 M solution in THF, 3.20 mmol) was added slowly and the mixture stirred for 2 hours at −20° C., then warmed to room temperature. After completion of the reaction (TLC), the mixture was quenched with ammonium chloride solution. Diethyl ether (10 ml) was added and the phases separated. The aqueous layer was extracted with diethyl ether (3×10 ml) and the combined organic phase was dried ($MgSO_4$) and filtered. The solvent was removed under reduced pressure to give the product as a pale-yellow oil. Yield=450 mg.

Example 24 Preparation of 1-((1R,2R)-2',6'-dimethoxy-5-methyl-4'-phenethyl-1,2,3,4-tetrahydro-[1,1'-biphenyl]-2-yl)ethan-1-one-2,2,2-$d_3$

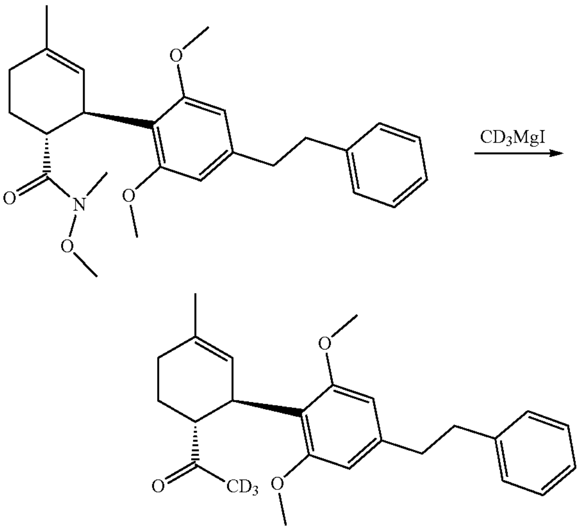

A solution of (1R,2R)-2-(2,6-dimethoxy-4-phenethylphenyl)-N-methoxy-N,4-dimethylcyclohex-3-enecarboxamide (440 mg, 1.04 mmol) in THF (5 ml) was cooled to −5° C. under argon. A solution of $CD_3MgI$ (1.1 ml of a 1.0 M solution in THF, 1.1 mmol) was added slowly and the mixture stirred for 2 hours at −5° C., then warmed to room temperature and stirred overnight. The mixture was quenched with ammonium chloride solution and diethyl ether (100 ml) was added and the phases separated. The aqueous layer was extracted with diethyl ether (3×10 ml) and the combined organic phase was dried ($MgSO_4$) and filtered. The solvent was removed under reduced pressure to give the product as a pale-yellow oil. Yield=400 mg.

Example 25. Preparation of (1R,2R)-2',6'-dimethoxy-5-methyl-4'-phenethyl-2-(prop-1-en-2-yl-$d_5$)-1,2,3,4-tetrahydro-1,1'-biphenyl

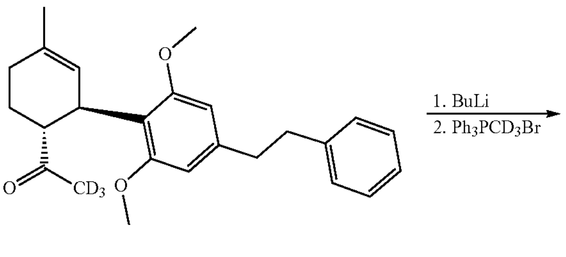

-continued

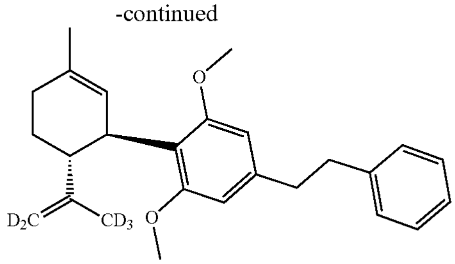

A solution of $d_3$-methyltriphenylphosphonium bromide (496 mg, 1.38 mmol) in THF (10 ml) was cooled to 0° C. under argon. A solution of butyllithium (0.86 ml of a 1.6 M solution in hexanes, 1.38 mmol) was added slowly and the mixture stirred for 2 hours at 0° C. A solution of 1-((1R, 2R)-2',6'-dimethoxy-5-methyl-4'-phenethyl-1,2,3,4-tetrahydro-[1,1'-biphenyl]-2-yl)ethan-1-one-2,2,2-$d_3$ (350 mg, 0.92 mmol) in THF (5 ml) was added and the mixture stirred for 1 hour at 0° C., then warmed to room temperature and stirred overnight. The mixture was quenched with ammonium chloride solution and diethyl ether (10 ml) was added and the phases separated. The aqueous layer was extracted with diethyl ether (3×10 ml) and the combined organic phase was dried ($MgSO_4$) and filtered. The solvent was removed under reduced pressure to give the product as a pale-yellow oil. Yield=302 mg.

Example 26. Preparation of (1'R,2'R)-5'-methyl-4-phenethyl-2'-(prop-1-en-2-yl-$d_5$)-1',2',3',4'-tetrahydro-[1,1'-biphenyl]-2,6-diol

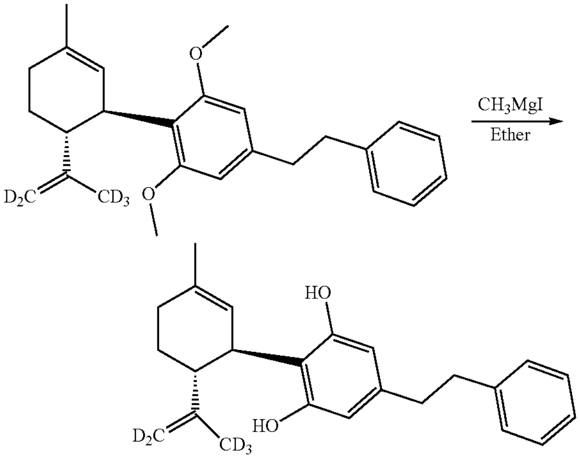

(1R,2R)-2',6'-dimethoxy-5-methyl-4'-phenethyl-2-(prop-1-en-2-yl-$d_5$)-1,2,3,4-tetrahydro-1,1'-biphenyl 110 mg, 0.29 mmol) was added to a Schlenk flask under argon at 0° C. A solution of $CH_3MgI$ (2.0 ml of a 3.0 M solution in $Et_2O$, 6.0 mmol) was added slowly at 0° C. and the mixture allowed to warm to room temperature and stirred for 30 minutes. The solvent was slowly removed under reduced pressure, then the resultant viscous mixture heated to 160° C. for 3 hours under vacuum. It was cooled to room temperature and diethyl ether (10 ml) added. Saturated $NH_4Cl$ (10 ml) was used to quench the reaction mixture and the phases separated. The aqueous layer was extracted with diethyl ether (3×10 ml), washed with brine, and the combined organic layers dried ($MgSO_4$), then filtered and concentrated to give the crude intermediate as a pale-yellow oil. Yield=92 mg.

Example 27. Preparation of (1R,2R)-2-(4-bromo-2,6-dimethoxyphenyl)-N-methoxy-N,4-dimethylcyclohex-3-enecarboxamide

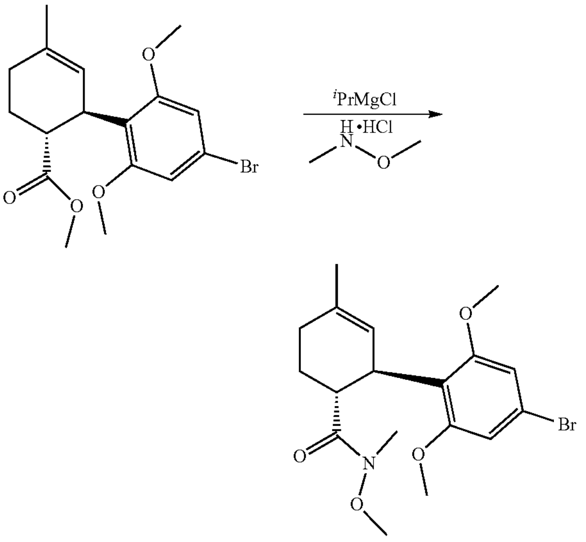

THF (10 ml) was added to a mixture of (1R,2R)-methyl 2-(4-bromo-2,6-dimethoxyphenyl)-4-methylcyclohex-3-enecarboxylate (1.0 g, 2.59 mmol) and N,O-dimethylhydroxylamine hydrochloride (0.392 g, 4.05 mmol) and the mixture was cooled to −20° C. under argon. A solution of isopropylmagnesium chloride (3.9 ml of a 2.0 M solution in THF, 3.20 mmol) was added slowly and the mixture stirred for 2 hours at −20° C., then warmed to room temperature. After completion of the reaction (TLC), the mixture was quenched with ammonium chloride solution. Diethyl ether (10 ml) was added and the phases separated. The aqueous layer was extracted with diethyl ether (3×10 ml) and the combined organic phase was dried ($MgSO_4$) and filtered. The solvent was removed under reduced pressure to give the product as an off-white solid. Yield=1.15 g.

Example 28. Preparation of 1-((1R,2R)-4'-bromo-2',6'-dimethoxy-5-methyl-1,2,3,4-tetrahydro-[1,1'-biphenyl]-2-yl)ethan-1-one-2,2,2-$d_3$

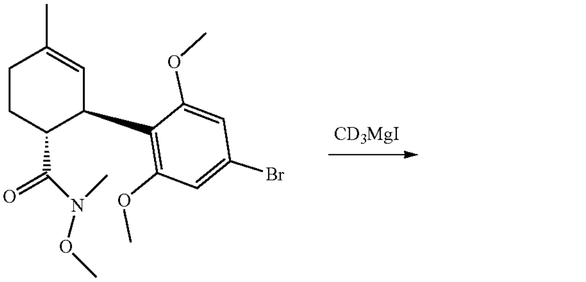

-continued

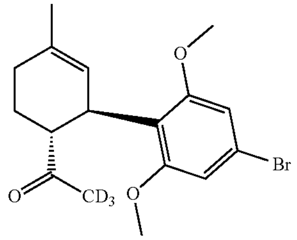

A solution of (1R,2R)-2-(4-bromo-2,6-dimethoxyphenyl)-N-methoxy-N,4-dimethylcyclohex-3-enecarboxamide (0.80 g, 2.01 mmol) in THF (5 ml) was cooled to −5° C. under argon. A solution of $CD_3MgI$ (2.15 ml of a 1.0 M solution in THF, 2.15 mmol) was added slowly and the mixture stirred for 2 hours at −5° C., then warmed to room temperature and stirred overnight. The mixture was quenched with ammonium chloride solution and diethyl ether (100 ml) was added and the phases separated. The aqueous layer was extracted with diethyl ether (3×10 ml) and the combined organic phase was dried ($MgSO_4$) and filtered. The solvent was removed under reduced pressure to give the product as an off-white solid. Yield=0.65 g.

Example 29. Preparation of (1R,2R)-4'-bromo-2',6'-dimethoxy-5-methyl-2-(prop-1-en-2-yl-$d_5$)-1,2,3,4-tetrahydro-1,1'-biphenyl

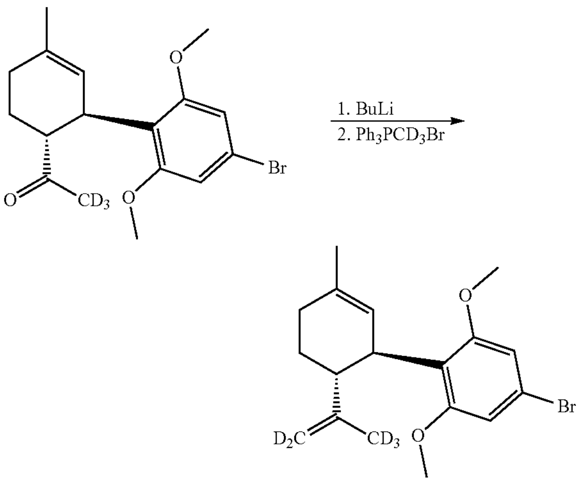

A solution of $d_3$-methyltriphenylphosphonium bromide (0.54 g, 1.49 mmol) in THF (5 ml) was cooled to 0° C. under argon. A solution of butyllithium (0.93 ml of a 1.6 M solution in hexanes, 1.49 mmol) was added slowly and the mixture stirred for 2 hours at 0° C. A solution of 1-((1R,2R)-4'-bromo-2',6'-dimethoxy-5-methyl-1,2,3,4-tetrahydro-[1,1'-biphenyl]-2-yl)ethan-1-one-2,2,2-$d_3$ (0.50 g, 1.40 mmol) in THF (5 ml) was added and the mixture stirred for 1 hour at 0° C., then warmed to room temperature and stirred overnight. The mixture was quenched with ammonium chloride solution and diethyl ether (10 ml) was added and the phases separated. The aqueous layer was extracted with diethyl ether (3×10 ml) and the combined organic phase was dried ($MgSO_4$) and filtered. The solvent was removed under reduced pressure to give the product as a pale-yellow oil which solidified overnight. Yield=0.46 g.

Example 30. Preparation of (1R,2R)-4'-icosyl-2',6'-dimethoxy-5-methyl-2-(prop-1-en-2-yl-$d_5$)-1,2,3,4-tetrahydro-1,1'-biphenyl

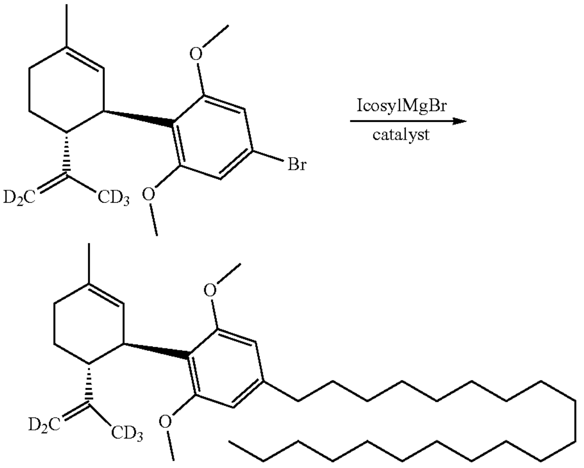

A solution of icosylmagnesium bromide (0.67 ml of a 0.5 M solution in THF, 0.34 mmol) was added to a mixture of $ZnBr_2$ (70 mg, 0.34 mmol) and LiBr (29 mg, 0.34 mmol) and the mixture stirred for 30 minutes at room temperature. A solution of (1R,2R)-4'-bromo-2',6'-dimethoxy-5-methyl-2-(prop-1-en-2-yl-$d_5$)-1,2,3,4-tetrahydro-1,1'-biphenyl (100 mg, 0.28 mmol) in THF (5 ml) was added to the mixture and $PdCl_2$(dppf) (5 mg, 0.007 mmol) added and the mixture stirred at 60° C. overnight under argon. It was cooled to room temperature and quenched with ammonium chloride solution and hexanes added. The phases were separated, and the organic layer was dried ($MgSO_4$), filtered and evaporated to dryness. The residue was filtered through a short silica gel pad, eluting with ethyl acetate/hexanes (1/6). The product was isolated as colourless oil which slowly solidified to a white solid. Yield=142 mg.

Example 31. Preparation of ((1',2'R)-2,6-dimethoxy-5'-methyl-2'-(prop-1-en-2-yl-$d_5$)-1',2',3',4'-tetrahydro-[1,1'-biphenyl]-4-yl)boronic acid

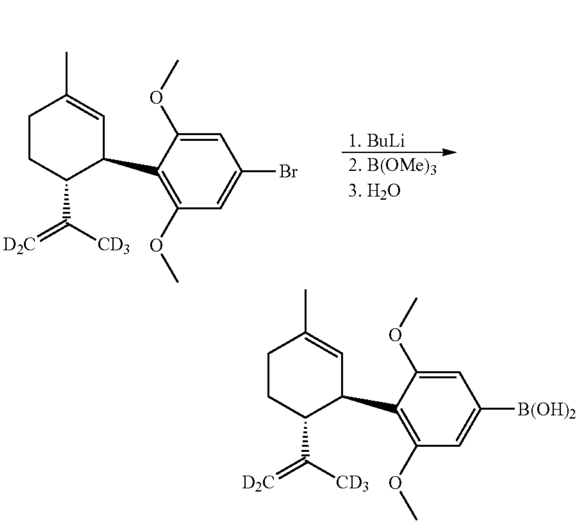

A solution of (1R,2R)-4'-bromo-2',6'-dimethoxy-5-methyl-2-(prop-1-en-2-yl-$d_5$)-1,2,3,4-tetrahydro-1,1'-biphenyl (100 mg, 0.28 mmol) in THF (5 ml) was cooled to −70° C. and butyllithium (0.2 ml of a 1.6 M solution in hexanes, 0.32 mmol) added. The mixture was stirred for 1 hour under argon, and trimethylborate (35 mg, 0.34 mmol) added. The mixture was then allowed to warm to room temperature and stirred for 4 hours under argon. It was quenched with ammonium chloride solution and stirred overnight. Ethyl acetate was added, and the phases were separated. The organic layer was dried ($MgSO_4$), filtered and evaporated to dryness. The residue was recrystallized from ethyl acetate and hexanes. Yield=85 mg.

Example 32. Preparation of 1-((1R,2R)-2',6'-dimethoxy-5-methyl-4'-pentyl-1,2,3,4-tetrahydro-[1,1'-biphenyl]-2-yl)ethan-1-one-2-$^{13}C$

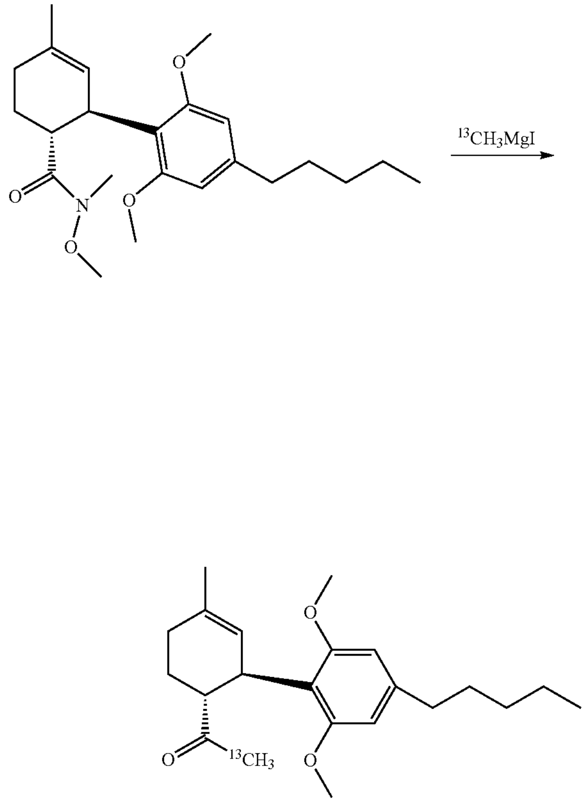

A solution of (1R,2R)-2-(2,6-dimethoxy-4-pentylphenyl)-N-methoxy-N,4-dimethylcyclohex-3-enecarboxamide (100 mg, 0.26 mmol) in THF (5 ml) was cooled to −5° C. under argon. A solution of $^{13}CH_3MgI$ (0.27 ml of a 1.0 M solution in THF, 0.27 mmol) was added slowly and the mixture stirred for 2 hours at −5° C., then warmed to room temperature and stirred overnight. The mixture was quenched with ammonium chloride solution and diethyl ether (10 ml) was added and the phases separated. The aqueous layer was extracted with diethyl ether (3×10 ml) and the combined organic phase was dried ($MgSO_4$) and filtered. The solvent was removed under reduced pressure to give the product as a pale-yellow liquid. Yield=84 mg.

Example 33. Preparation of (1R,2R)-2',6'-dimethoxy-5-methyl-4'-pentyl-2-(prop-1-en-2-yl-3-$^{13}C$-1,1-$d_2$)-1,2,3,4-tetrahydro-1,1'-biphenyl

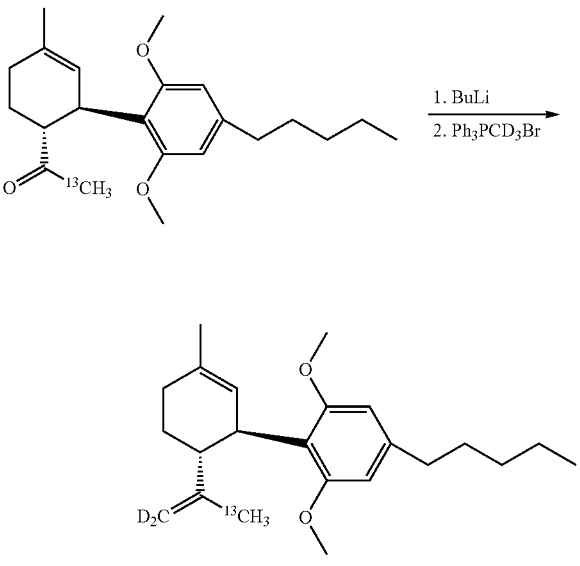

A solution of $d_3$-methyltriphenylphosphonium bromide (125 mg, 0.35 mmol) in THF (5 ml) was cooled to 0° C. under argon. A solution of butyllithium (0.22 ml of a 1.6 M solution in hexanes, 0.35 mmol) was added slowly and the mixture stirred for 2 hours at 0° C. A solution of 1-((1R,2R)-2',6'-dimethoxy-5-methyl-4'-pentyl-1,2,3,4-tetrahydro-[1,1'-biphenyl]-2-yl)ethan-1-one-2-$^{13}C$ (80 mg, 0.23 mmol) in THF (5 ml) was added and the mixture stirred for 1 hour at 0° C., then warmed to room temperature and stirred overnight. The mixture was quenched with ammonium chloride solution and diethyl ether (10 ml) was added and the phases separated. The aqueous layer was extracted with diethyl ether (3×10 ml) and the combined organic phase was dried ($MgSO_4$) and filtered. The solvent was removed under reduced pressure to give the product as a pale-yellow liquid. Yield=72 mg.

Example 34. Preparation of 1-((1R,2R)-4'-bromo-2',6'-dimethoxy-5-methyl-1,2,3,4-tetrahydro-[1,1'-biphenyl]-2-yl)ethan-1-one-2-$^{13}C$

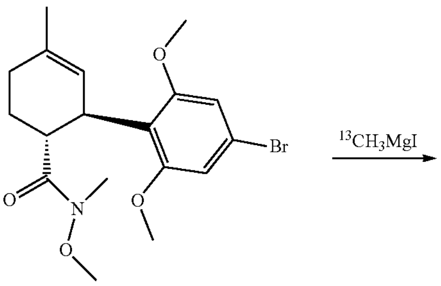

-continued

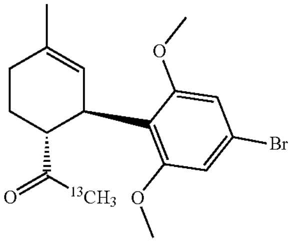

A solution of (1R,2R)-2-(4-bromo-2,6-dimethoxyphenyl)-N-methoxy-N,4-dimethylcyclohex-3-enecarboxamide (282 mg, 0.71 mmol) in THF (5 ml) was cooled to −5° C. under argon. A solution of $^{13}CH_3MgI$ 0.75 ml of a 1.0 M solution in THF, 1.06 mmol) was added slowly and the mixture stirred for 2 hours at −5° C., then warmed to room temperature and stirred overnight. The mixture was quenched with ammonium chloride solution and diethyl ether (10 ml) was added and the phases separated. The aqueous layer was extracted with diethyl ether (3×10 ml) and the combined organic phase was dried ($MgSO_4$) and filtered. The solvent was removed under reduced pressure to give the product as an off-white solid. Yield=235 mg.

Example 35. Preparation of (1R,2R)-4'-bromo-2',6'-dimethoxy-5-methyl-2-(prop-1-en-2-yl-3-$^{13}$C)-1,2,3,4-tetrahydro-1,1'-biphenyl

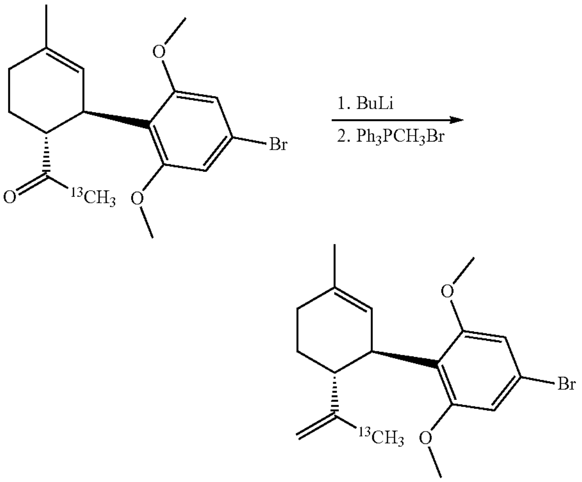

A solution of methyltriphenylphosphonium bromide (304 mg, 0.85 mmol) in THF (5 ml) was cooled to 0° C. under argon. A solution of butyllithium (0.54 ml of a 1.6 M solution in hexanes, 1.49 mmol) was added slowly and the mixture stirred for 2 hours at 0° C. A solution of 1-((1R,2R)-4'-bromo-2',6'-dimethoxy-5-methyl-1,2,3,4-tetrahydro-[1,1'-biphenyl]-2-yl)ethan-1-one-2-$^{13}$C (201 mg, 0.57 mmol) in THF (5 ml) was added and the mixture stirred for 1 hour at 0° C., then warmed to room temperature and stirred overnight. The mixture was quenched with ammonium chloride solution and diethyl ether (10 ml) was added and the phases separated. The aqueous layer was extracted with diethyl ether (3×10 ml) and the combined organic phase was dried ($MgSO_4$) and filtered. The solvent was removed under reduced pressure to give the product as a pale-yellow oil which solidified overnight. Yield=182 mg.

Example 36. Preparation of (1R,2R)-2',6'-dimethoxy-5-methyl-4'-pentyl-2-(prop-1-en-2-yl-3-$^{13}$C)-1,2,3,4-tetrahydro-1,1'-biphenyl

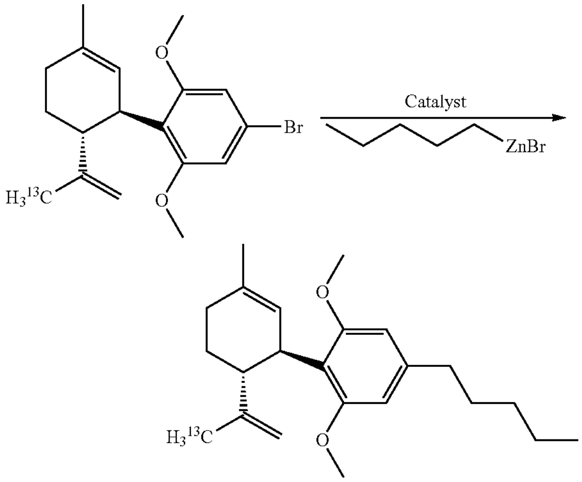

A solution of n-pentylzinc bromide (0.67 ml of a 0.5 M solution in THF, 0.34 mmol) was added to a mixture of (1R,2R)-4'-bromo-2',6'-dimethoxy-5-methyl-2-(prop-1-en-2-yl-3-$^{13}$C)-1,2,3,4-tetrahydro-1,1'-biphenyl (100 mg, 0.28 mmol) and $PdCl_2$(dppf) (5 mg, 0.007 mmol) and the mixture stirred at room temperature for 6 hours under argon. It was quenched with ammonium chloride solution and diethyl ether added. The phases were separated, and the organic layer was dried ($MgSO_4$), filtered and evaporated to dryness. The NMR spectrum of the residue shows 100% conversion of the substrate to the product. Flash chromatography using hexanes/ethyl acetate yielded the product as a pale-yellow oil. Yield=94 mg.

Example 37. Preparation of (1R,2R)-4'-bromo-2',6'-dimethoxy-5-methyl-2-(prop-1-en-2-yl-3-$^{13}$C-1,1-$d_2$)-1,2,3,4-tetrahydro-1,1'-biphenyl

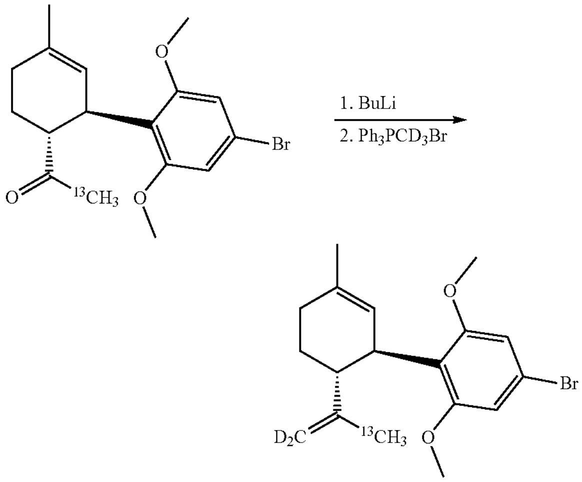

A solution of $d_3$-methyltriphenylphosphonium bromide (142 mg, 0.39 mmol) in THF (5 ml) was cooled to 0° C.

under argon. A solution of butyllithium (0.25 ml of a 1.6 M solution in hexanes, 0.39 mmol) was added slowly and the mixture stirred for 2 hours at 0° C. A solution of 1-((1R, 2R)-4'-bromo-2',6'-dimethoxy-5-methyl-1,2,3,4-tetrahydro-[1,1'-biphenyl]-2-yl)ethan-1-one-2-$^{13}C$ (93 mg, 0.26 mmol) in THF (5 ml) was added and the mixture stirred for 1 hour at 0° C., then warmed to room temperature and stirred overnight. The mixture was quenched with ammonium chloride solution and diethyl ether (10 ml) was added and the phases separated. The aqueous layer was extracted with diethyl ether (3×10 ml) and the combined organic phase was dried ($MgSO_4$) and filtered. The solvent was removed under reduced pressure to give the product as a pale-yellow oil which solidified overnight. Yield=83 mg.

Example 38. Preparation of (1R,2R)-2',6'-dimethoxy-5-methyl-4'-pentyl-2-(prop-1-en-2-yl-3-$^{13}C$-1,1-$d_2$)-1,2,3,4-tetrahydro-1,1'-biphenyl

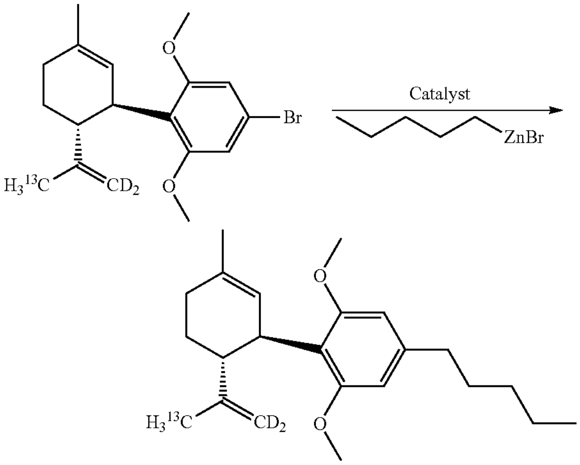

A solution of n-pentylzinc bromide (0.67 ml of a 0.5 M solution in THF, 0.34 mmol) was added to a mixture of (1R,2R)-4'-bromo-2',6'-dimethoxy-5-methyl-2-(prop-1-en-2-yl-3-$^{13}C$-1,1-$d_2$)-1,2,3,4-tetrahydro-1,1'-biphenyl (100 mg, 0.28 mmol) and $PdCl_2$(dppf) (5 mg, 0.007 mmol) and the mixture stirred at room temperature for 6 hours under argon. It was quenched with ammonium chloride solution and diethyl ether added. The phases were separated, and the organic layer was dried ($MgSO_4$), filtered and evaporated to dryness. The NMR spectrum of the residue shows 100% conversion of the substrate to the product. Flash chromatography using hexanes/ethyl acetate yielded the product as a pale-yellow oil. Yield=92 mg.

Example 39. Preparation of methyl 5-bromohex-5-enoate

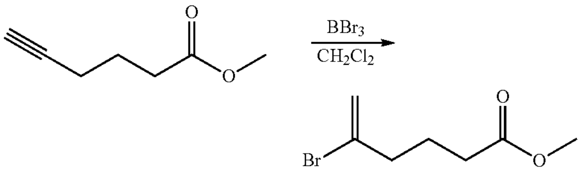

Methyl 5-hexynoate (20 g, 158 mmol) was added to a solution of $BBr_3$ (39.7 g, 158 mmol) in $CH_2Cl_2$ at −78° C. and the mixture was allowed to reach room temperature over 4 hours with stirring. Acetic acid (40 ml) was added slowly and the mixture was stirred for 30 minutes. Water (150 ml) was added and the phases were separated. The organic layer was washed with $NaHCO_3$ solution, then brine and dried ($MgSO_4$). It was filtered through a pad of silica gel and evaporated to dryness. Yield=19.6 g.

Example 40. Preparation of methyl 5-methylhex-5-enoate

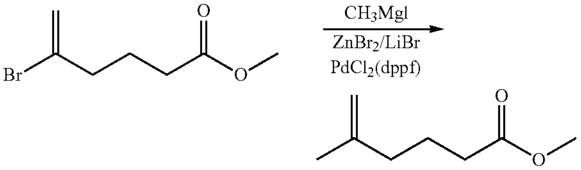

Methylmagnesium iodide (1.77 ml of a 3.0 M, 5.3 mmol) was added to a THF (15 ml) mixture of $ZnBr_2$ (1.30 g, 5.8 mmol) and LiBr (0.50 g, 5.8 mmol) at room temperature and stirred for 30 minutes. A solution of methyl 5-bromohex-5-enoate (1.0 g, 4.83 mmol) in THF (3 ml) was added along with $PdCl_2$(dppf) (88 mg, 0.12 mmol) and the mixture was heated to 60° C. for overnight under argon. It was quenched with ammonium chloride solution and diethyl ether added. The phases were separated, and the organic layer was dried ($MgSO_4$), filtered through a pad of silica gel and evaporated to dryness. Yield=0.65 g.

Example 41. Preparation of 5-methylhex-5-enoic acid

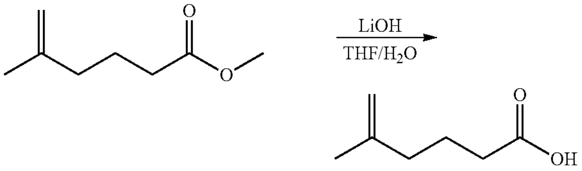

Methyl 5-methylhex-5-enoate (0.5 g, 3.5 mmol) was added to THF/Methanol/water (10 ml of a 2/2/1 mixture) and LiOH (1.7 g, 70 mmol) added at 0° C. The mixture was warmed to room temperature and stirred until the reaction was complete (TLC). It was acidified using $NaH_2PO_4$ and ethyl acetate (10 ml) added. The phases were separated, and the aqueous phase extracted with ethyl acetate. The combined organic phase was washed with brine, dried ($MgSO_4$), filtered through a pad of silica gel and the solvent removed under reduced pressure. Yield=0.42 g.

Example 42. Preparation of methyl methyl 5-(methyl-$d_3$)hex-5-enoate

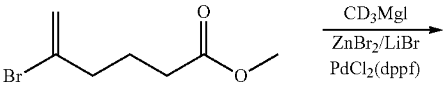

-continued

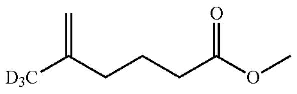

This was prepared as described in Example 40, using $CD_3MgI$ and methyl 5-bromohex-5-enoate.

Example 43. Preparation of 5-(methyl-$d_3$)hex-5-enoic acid

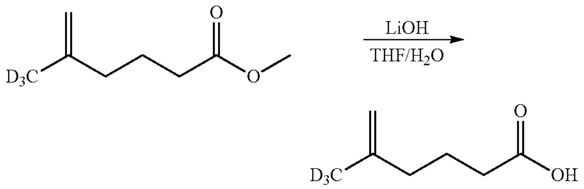

This was prepared as described in Example 41, using methyl 5-(methyl-$d_3$)hex-5-enoate.

Example 44. Preparation of methyl methyl 5-(methyl-$^{13}C$)hex-5-enoate

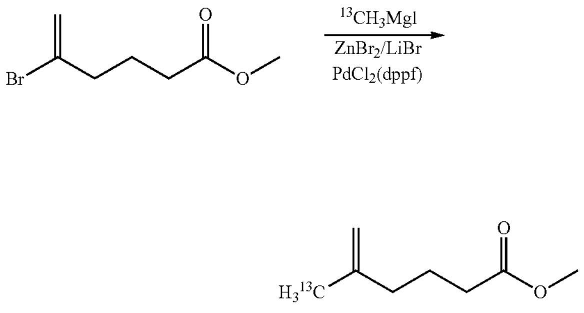

This was prepared as described in Example 40, using $^{13}C$-methylmagnesium iodide and methyl 5-bromohex-5-enoate.

Example 45. Preparation of 5-(methyl-$^{13}C$)hex-5-enoic acid

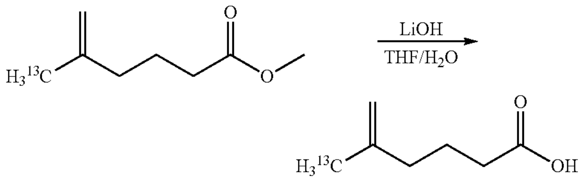

This was prepared as described in Example 41, using methyl 5-(methyl-$^{13}C$)hex-5-enoate.

Example 46. Preparation of methyl (1R,2R)-4'-bromo-2',6'-dimethoxy-5-(methyl-$d_3$)-1,2,3,4-tetrahydro-[1,1'-biphenyl]-2-carboxylate

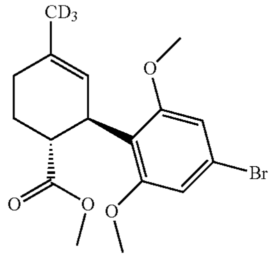 [SMILES: [2H]C([2H])([2H])C1=C[C@@H](c2c(OC)cc(Br)cc2OC)[C@H](C(=O)OC)CC1]

Methyl (1R,2R)-4'-bromo-2',6'-dimethoxy-5-(methyl-$d_3$)-1,2,3,4-tetrahydro-[1,1'-biphenyl]-2-carboxylate was prepared from 5-(methyl-$d_3$)hex-5-enoic acid and (S,E)-4-(4-bromo-2,6-dimethoxyphenyl)but-3-en-2-ol using the procedures described in Examples 4 to 7.

Example 47. Preparation of methyl (1R,2R)-4'-bromo-2',6'-dimethoxy-5-(methyl-$^{13}C$)-1,2,3,4-tetrahydro-[1,1'-biphenyl]-2-carboxylate

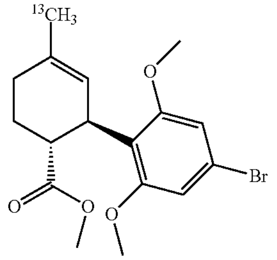 [SMILES: COC(=O)[C@@H]1CCC([13CH3])=C[C@H]1c1c(OC)cc(Br)cc1OC]

Methyl (1R,2R)-4'-bromo-2',6'-dimethoxy-5-(methyl-$^{13}C$)-1,2,3,4-tetrahydro-[1,1'-biphenyl]-2-carboxylate was prepared from 5-(methyl-$^{13}C$)hex-5-enoic acid and (S,E)-4-(4-bromo-2,6-dimethoxyphenyl)but-3-en-2-ol using the procedures described in Examples 4 to 7.

Example 48. Preparation of (E)-4-(2,4,6-trimethoxyphenyl)but-3-en-2-one

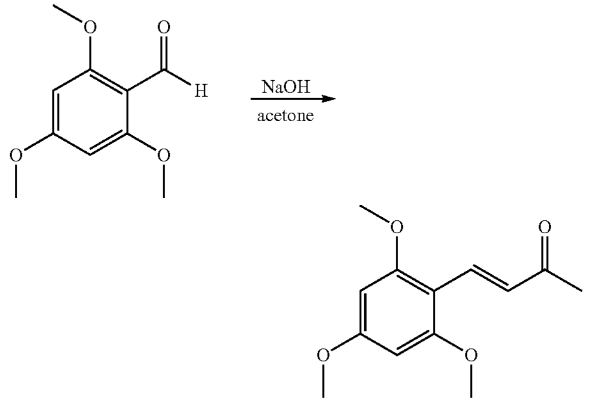

Water (200 ml) and 2,4,6-trimethoxybenzaldehyde (10.0 g, 51 mmol) was added to a 500 ml Schlenk flask. Acetone (16 g, 276 mmol) and NaOH (8.0 g, 200 mmol) in water (50 ml) were added and the reaction mixture was heated to 60° C. until all the aldehyde was converted (TLC, about 15 hours). The mixture was cooled to room temperature and extracted with diethyl ether (3×100 ml) and the combined organic layer was washed with 0.1 M $H_2SO_4$ (100 ml), brine (100 ml) and dried ($MgSO_4$). The mixture was concentrated to about 50 ml and filtered through a pad of silica gel. It was then evaporated to dryness to give a yellow solid. Yield=12.0 g.

Example 49. Preparation of (S,E)-4-(2,4,6-trimethoxyphenyl)but-3-en-2-ol

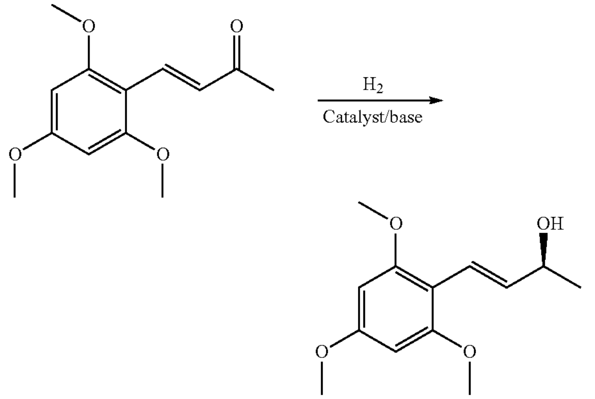

(E)-4-(2,4,6-trimethoxyphenyl)but-3-en-2-one (10.0 g, 42.3 mmol) was added to a mixture of $RuCl_2$(R-Xyl-Garphos)(R-Daipen) (25 mg, 0.02 mmol) and $K_2CO_3$ (1.0 g, 7.2 mmol) in a 100 ml Parr pressure reactor. The mixture was degassed with hydrogen and 2-propanol (50 ml) was added with stirring. A solution of $KO^tBu$ (5 mg, 0.045 mmol) in 2-propanol (5 ml) was then added. The pressure was set to 30 atm and the temperature was set to 30° C. and the mixture was stirred for 10 hours. The mixture was cooled to room temperature and the hydrogen vented. The solvent was removed, and the mixture dissolved in diethyl ether and filtered through a pad of silica gel. The solvent was removed under reduced pressure to give the product. Yield=10.62 g (97% e.e., S-isomer).

Example 50. Preparation of (S,E)-4-(2,4,6-trimethoxyphenyl)but-3-en-2-yl 5-methylhex-5-enoate

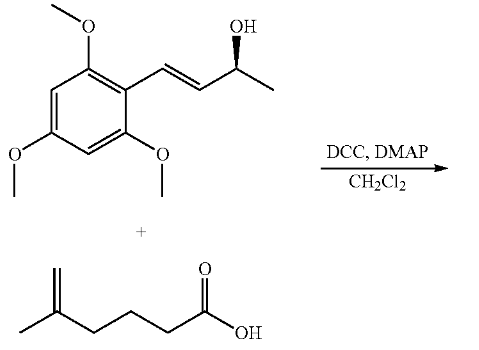

-continued

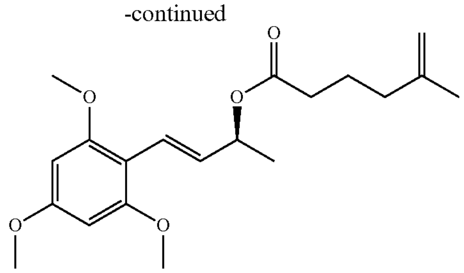

(S,E)-4-(2,4,6-trimethoxyphenyl)but-3-en-2-ol (10.0 g, 42.0 mmol) was added to a 500 ml Schlenk along with $CH_2Cl_2$ (250 ml) and the mixture cooled to 0° C. with stirring. DCC (10.4 g, 50 mmol) and DMAP (0.50 g, 4.1 mmol) were added along with 5-methylhex-5-enoic acid (5.38 g, 42.0 mmol). The mixture was stirred at 0° C. for 2 hours then warmed to room temperature and stirred overnight. On completion of the reaction (TLC) the mixture was filtered and the filtrate was washed with 0.5 M $H_2SO_4$ (200 ml), followed by saturated $NaHCO_3$ solution (200 ml) and brine. The mixture was dried ($MgSO_4$), then filtered and concentrated under vacuum. The crude material was purified by column chromatography using hexanes/ethyl acetate (10:1) to give the product as a pale-yellow oil. Yield=14.76 g.

While the foregoing disclosure has been described in some detail for purposes of clarity and understanding, it will be appreciated by one skilled in the art, from a reading of the disclosure that various changes in form and detail can be made without departing from the true scope of the disclosure in the appended claims.

All publications, patents, and patent applications are herein incorporated by reference in their entirety to the same extent as if each individual publication, patent or patent application was specifically and individually indicated to be incorporated by reference in its entirety.

The invention claimed is:

1. A compound of Formula (I):

(I)

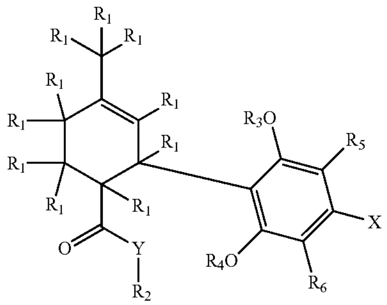

wherein, the $R_1$ groups are independently or simultaneously selected from the group consisting of hydrogen and deuterium;

$R_3$ to $R_4$ are selected from the group consisting of hydrogen, deuterium, an optionally substituted $C_1$-$C_{20}$-alkyl group, an optionally substituted $C_2$-$C_{20}$-alkenyl group, an optionally substituted $C_2$-$C_{20}$-alkynyl group, an optionally substituted $C_3$-$C_{20}$-cycloalkyl group, an optionally substituted $C_6$-$C_{14}$-aryl group, an optionally substituted $C_5$-$C_{14}$-heteroaryl, and an optionally substituted acyl group, and one or more of the carbon atoms in the alkyl, alkenyl, alkynyl, cycloalkyl, aryl, heteroaryl or acyl groups of $R_3$ and $R_4$ is optionally replaced with a heteroatom selected from the group consisting of O, S, N, P and Si, which, where possible, is optionally substituted, wherein the optional substituents are one or more groups selected from the group consisting of OH, halo and $C_1$-$C_6$-alkyl;

Y is selected from the group consisting of O and $NR^c$, in which $R^c$ is selected from the group consisting of hydrogen atom, $C_1$-$C_6$-alkyl, $C_3$-$C_6$-cycloalkyl, $C_6$-$C_{10}$-aryl and $C_2$-$C_6$-alkenyl group;

$R_2$ is selected from the group consisting of a hydrogen atom, $C_1$-$C_6$-alkyl, $C_3$-$C_6$-cycloalkyl, $C_6$-$C_{10}$-aryl, $C_2$-$C_6$-alkenyl group and $OR^c$;

$R_5$ and $R_6$ are selected from the group consisting of hydrogen, deuterium, halide, an optionally substituted $C_1$-$C_{20}$-alkyl group, an optionally substituted $C_2$-$C_{20}$-alkenyl group, an optionally substituted $C_2$-$C_{20}$-alkynyl group, an optionally substituted $C_3$-$C_{20}$-cycloalkyl group, an optionally substituted $C_6$-$C_{14}$-aryl group, an optionally substituted $C_5$-$C_{14}$-heteroaryl, an optionally substituted acyl group, or an optionally substituted carboxylate group, and one or more of the carbon atoms in the alkyl, alkenyl, alkynyl, cycloalkyl, aryl, heteroaryl, acyl or carboxylate groups of $R_5$ and/or $R_6$ is optionally replaced with a heteroatom selected from the group consisting of O, S, N, P and Si, which, where possible, is optionally substituted, wherein the optional substituents are one or more groups selected from the group consisting of OH, halo and $C_1$-$C_6$-alkyl; and X is selected from the group consisting of halide, sulfonate, carboxylate, carbonate and a group having the formula $MW_n$, wherein M is selected from the group consisting of Li, Mg, Zn, Sn, B, and Si, W is selected from the group consisting of halide, OH, and OR, and R is selected from the group consisting of $C_1$-$C_{10}$-alkyl group and $C_6$-$C_{10}$-aryl group.

2. The compound of Formula (I) according to claim 1, wherein at least one of the carbon-12 atoms in the cyclohexene ring and its substituents, is replaced with a carbon-13 or carbon-14 atom.

3. The compound of Formula (I) according to claim 1, wherein X is bromide.

4. The compound of Formula (I) according to claim 1, wherein $R_3$ and $R_4$ are selected from the group consisting of hydrogen, deuterium, or an optionally substituted $C_1$-$C_3$-alkyl group.

5. The compound of Formula (I) according to claim 1, wherein $R_5$ and $R_6$ are selected from the group consisting of hydrogen, deuterium, or an optionally substituted $C_1$-$C_3$-alkyl group.

6. The compound of Formula (I) according to claim 1, wherein Y is O.

7. A compound of Formula (IV):

(IV)

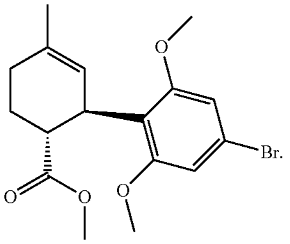

8. The compound according to claim 2, wherein the deuterium and carbon-13 enrichment is no less than 1% at the specified position.

9. The compound according to claim 2, wherein the deuterium and carbon-13 enrichment is no less than 100% at the specified position.

10. The compound according to claim 2, wherein the carbon-14 enrichment is no less than one part per million at the specified position.

* * * * *